(12) United States Patent
Willson et al.

(10) Patent No.: US 10,533,996 B2
(45) Date of Patent: Jan. 14, 2020

(54) PHOSPHORESCENT REPORTERS

(71) Applicant: University of Houston, Houston, TX (US)

(72) Inventors: Richard Willson, Houston, TX (US); Andrew Paterson, Houston, TX (US)

(73) Assignee: University of Houston, Houston, TX (US)

(*) Notice: Subject to any disclaimer, the term of this patent is extended or adjusted under 35 U.S.C. 154(b) by 684 days.

(21) Appl. No.: 14/461,118

(22) Filed: Aug. 15, 2014

(65) Prior Publication Data

US 2015/0105284 A1 Apr. 16, 2015

Related U.S. Application Data

(60) Provisional application No. 61/867,263, filed on Aug. 19, 2013.

(51) Int. Cl.
*C12Q 1/68* (2018.01)
*G01N 33/569* (2006.01)

(52) U.S. Cl.
CPC ... *G01N 33/56983* (2013.01); *G01N 2458/00* (2013.01)

(58) Field of Classification Search
USPC ......... 435/7.1, 6, 1, 6.11, 91.1; 436/94, 501; 536/23.1, 24.3, 24.33; 530/300, 350, 530/387.1
See application file for complete search history.

(56) References Cited

U.S. PATENT DOCUMENTS

| 3,634,558 A | 1/1972 | Stober |
| 4,795,588 A | 1/1989 | Pet et al. |
| 5,043,265 A | 8/1991 | Tanke et al. |
| 5,061,076 A | 10/1991 | Hurley |
| 5,650,094 A | 7/1997 | Royce et al. |

(Continued)

FOREIGN PATENT DOCUMENTS

| EP | 0723146 A1 | 7/1996 |
| EP | 1692508 B1 | 12/2010 |

OTHER PUBLICATIONS

J. Dekker, "Luminescence," in *Solid State Physics*, London: Macmillan & Co Ltd, 1962, pp. 398-417.

(Continued)

*Primary Examiner* — Frank W Lu
(74) *Attorney, Agent, or Firm* — Todd A. Lorenz; David H. Goetz

(57) ABSTRACT

In some embodiments, the present disclosure pertains to new compositions of matter that comprise phosphorescent reporters. In some embodiments, the phosphorescent reporters of the present disclosure comprise strontium aluminate. In some embodiments, the strontium aluminate is doped with europium and dysprosium ($SrAl_2O_4:Eu^{2+}, Dy^{3+}$). Additional embodiments of the present disclosure pertain to methods of making the aforementioned phosphorescent reporters. In some embodiments, the method includes size reduction of inorganic phosphorescent powders through a combination of wet milling and settling. In additional embodiments, the present disclosure pertains to methods of detecting the phosphorescent reporters in various settings, such as diagnostic settings.

6 Claims, 43 Drawing Sheets

(56) References Cited

U.S. PATENT DOCUMENTS

| | | | |
|---|---|---|---|
| 5,674,698 | A | 10/1997 | Zarling et al. |
| 5,854,008 | A | 12/1998 | Diamandis |
| 5,922,537 | A | 7/1999 | Ewart et al. |
| 6,039,894 | A | 3/2000 | Sanjurjo et al. |
| 6,242,043 | B1 | 6/2001 | Lipp |
| 6,372,516 | B1 | 4/2002 | Sun |
| 6,924,153 | B1 | 8/2005 | Boehringer et al. |
| 6,969,475 | B2 | 11/2005 | Hyland, Jr. et al. |
| 7,323,696 | B2 | 1/2008 | Vann et al. |
| 7,390,437 | B2 | 6/2008 | Dong et al. |
| 7,427,365 | B2 | 9/2008 | Hirata et al. |
| 7,713,746 | B2 | 5/2010 | Lee et al. |
| 7,803,322 | B2 | 9/2010 | Borich et al. |
| 7,914,701 | B2 | 3/2011 | Huang et al. |
| 8,101,415 | B2 | 1/2012 | Irvin |
| 8,298,677 | B2 | 10/2012 | Wiesner et al. |
| 8,557,604 | B2 | 10/2013 | Song |
| 8,709,383 | B2 | 4/2014 | Scherman et al. |
| 9,034,204 | B2 | 5/2015 | Kennedy et al. |
| 2002/0175314 | A1 | 11/2002 | Suzuki et al. |
| 2003/0173540 | A1* | 9/2003 | Mortz ............ C04B 14/36 252/301.36 |
| 2004/0014060 | A1 | 1/2004 | Hoheisel et al. |
| 2004/0106190 | A1 | 6/2004 | Yang et al. |
| 2005/0112703 | A1 | 5/2005 | Song |
| 2005/0266269 | A1* | 12/2005 | Imai ............ C08K 3/01 428/698 |
| 2008/0305489 | A1* | 12/2008 | Thomas ........ A61K 49/0021 435/6.12 |
| 2008/0312427 | A1 | 12/2008 | Kwok et al. |
| 2009/0098057 | A1 | 4/2009 | Zheng et al. |
| 2009/0155173 | A1 | 6/2009 | Scherman et al. |
| 2009/0181398 | A1 | 7/2009 | Bauer et al. |
| 2011/0038947 | A1 | 2/2011 | Maurer et al. |
| 2011/0140045 | A1* | 6/2011 | Rodrigues ........ E01C 7/085 252/301.36 |
| 2012/0045748 | A1 | 2/2012 | Willson et al. |
| 2012/0157160 | A1 | 6/2012 | Ozcan et al. |
| 2012/0252025 | A1 | 10/2012 | Kwok et al. |
| 2012/0286203 | A1 | 11/2012 | Kennedy et al. |
| 2013/0011484 | A1 | 1/2013 | Bevier |
| 2013/0087719 | A1 | 4/2013 | Yang |
| 2013/0102003 | A1 | 4/2013 | Gibbs |
| 2013/0203043 | A1 | 8/2013 | Ozcan et al. |

OTHER PUBLICATIONS

Hampl, M., et al., "Upconverting phosphor reporters in immunochromatographic assays.," Anal. Biochem., vol. 288, No. 2, pp. 176-187, 2001.

Ji, P. T. et al., "Encapsulating MAl2O4: Eu2+, Dy3+ (M=Sr, Ca, Ba) phosphors with triethanolamine to enhance water resistance," Appl. Surf. Sci., vol. 258, No. 5, pp. 1888-1893, 2011.

Juntunen, E., et al., "Performance of fluorescent europium(III) nanoparticles and colloidal gold reporters in lateral flow bioaffinity assay.," Anal. Biochem., vol. 428, No. 1, pp. 31-38, 2012.

Kingshott, P., et al., "Effects of cloud-point grafting, chain length, and density of PEG layers on competitive adsorption of ocular proteins," Biomaterials, vol. 23, No. 9, pp. 2043-2056, 2002.

C. F. Lane, "Sodium Cyanoborohydride—A Highly Selective Reducing Agent for Organic Functional Groups," Synthesis (Stuttg)., vol. 1975, No. 03, pp. 135-146, 1975.

Lee, L. et al., "A Low-Cost, High-Performance System for Fluorescence Lateral Flow Assays," Biosensors, vol. 3, No. 4, pp. 360-373, 2013.

X. Lü, "Silica encapsulation study on SrAl2O4:Eu2+, Dy3+ phosphors," Mater. Chem.Phys., vol. 93, No. 2-3, pp. 526-530, Oct. 2005.

Maldiney, T., et al., "Controlling electron trap depth to enhance optical properties of persistent luminescence nanoparticles for in vivo imaging.," J. Am. Chem. Soc., vol. 133, No. 30, pp. 11810-11815, 2011.

Malmsten, M.,"Effect of Chain Density on Inhibition of Protein Adsorption by Poly(ethylene glycol) Based Coatings," J. Colloid Interface Sci., vol. 202, No. 2, pp. 507-517, 1998.

Matsuzawa, T., "A New Long Phosphorescent Phosphor with High Brightness, SrAl2O4:Eu2+,Dy3+," J. Electrochem. Soc., vol. 143, No. 8, p. 2670, 1996.

Mine, E., "Direct coating of gold nanoparticles with silica by a seeded polymerization technique.," J. Colloid Interface Sci., vol. 264, No. 2, pp. 385-390, 2003.

Mudanyali, O., et al., "Integrated rapid-diagnostic-test reader platform on a cellphone.," Lab Chip, vol. 12, No. 15, pp. 2678-2686, 2012.

S. Prabakar and R. A. Assink, "Hydrolysis and condensation kinetics of two component organically modified silica sols," J. Non. Cryst. Solids, vol. 211, No. 1-2, pp. 39-48, 1997.

Ramachandran, S., et al., "A Rapid, Multiplexed, High-Throughput Flow-Through Membrane Immunoassay: A Convenient Alternative to ELISA," Diagnostics, vol. 3, No. 2, pp. 244-260, 2013.

J. S. Reed, "Comminution," in Introduction to the Principles of Ceramic Processing, New York: John Wiley & Sons, 1988, pp. 255-272.

Ryu, Y., et al., "Increase in the detection sensitivity of a lateral flow assay for a cardiac marker by oriented immobilization of antibody," BioChip J., vol. 5, No. 3, pp. 193-198, 2011.

J. Sanchez and A. McCormick, "Kinetic and Thermodynamic Study of the Hydrolysis of Silicon Alkoxides in Acidic Alcohol Solutions," J. Phys. Chem., vol. 96, No. 22, pp. 8973-8979, 1992.

Song, X., et al.,"Bright and Monodispersed Phosphorescent Particle and their Applications for Biological Assays," Anal. Chem., vol. 80, No. 14, pp. 5501-5507, 2008.

R. Wong and H. Y. Tse, Eds., Lateral Flow Immunoassay. Totowa, NJ: Humana Press, 2009.

Zhang, Z., et al., "Synthesis of poly(ethylene glycol) (PEG)—grafted colloidal silica particles with improved stability in aqueous solvents.," J.Colloid Interface Sci., vol. 310, No. 2, pp. 446-455, 2007.

Zhu, Y., et al.,"Encapsulation of strontium aluminate phosphors to enhance water resistance and luminescence," Appl. Surf. Sci., vol. 255, No. 17, pp. 7580-7585, 2009.

Zhu, Y., et al., "Luminescence enhancing encapsulation for strontium aluminate phosphors with phosphate," Mater. Chem. Phys., vol. 113, No. 2-3, pp. 721-726, 2009.

Etvi, Juntunen et al.: "Performance of florescent europium (III) nanoparticles and colloidal gold reporters in lateral flow bioaffinity assay", Analytical Biochemistry, Elsevier, Amsterdam, NL, vol. 428, No. 1, Jun. 5, 2012, pp. 31-38, XP028450444, ISSN: 0003-2697, DOI: 10.1016/J.AB.2012.06.005 [retrieved on Jun. 13, 2012].

Paterson, Andrew et al.: "Rare-earth strontiom aluminate particles as reporters in point-of-care diagnostics", Abstrats of Papers American Chemical Society, vol. 245, Apr. 2013, pp. 330-BIOT, & 245th National Meeting of the American-Chemical-Society (ACS); New Orleans, LA, USA; Apr. 7-11, 2013 ISSN: 0065-7727.

Paterson, Andrew S et al.: "Persistent luminescence strontium aluminate nanoparticles as reporters in diagnostics", Abstracts of Papers American Chemical Society, vol. 247, Mar. 2014, pp. 432-BIOT, & 247th National Spring Meeting of the American-Chemical-Society (ACS); Dallas, TX, USA; Mar. 16-20, 2014.

Song, X et al.: "Time-resolved luminescent lateral flow assay technology", Analytica Chimica ACTA, Elsevier, Amsterdam, NL, vol. 626, No. 2, Sep. 26, 2008, pp. 186-192, XP025408763, ISSN: 0003-2670, DOI: 10.1016/J.ACA.2008.08.006 [retrieved on Aug. 20, 2008].

Yuhong, Wang, et al.: "Development of florescent nanoparticle-labeled lateral flow assay for the detection of nucleic acids", Biomedical Microdevices, vol. 15, No. 5, Oct. 23, 2013, pp. 751-758,XP055344302, NL ISSN: 1387-2176, DOI: 10.1007/s10544-013-9760-1.

Zhu Y et al.: "Luminescence enhancing encapsulation for strontium aluminate phosphors with phosphate", Materials Chemistry and Physics, Elsevier SA,Switzerland, Taiwan, Republic of China, vol.

(56) References Cited

OTHER PUBLICATIONS

113, No. 2-3, Feb. 15, 2009, pp. 721-726, XP025865581, ISSN: 0254-0584, DOI: 10.1016/J.MATCHEMPHYS.2008.08.007 [retrieved on Sep. 25, 2008].

* cited by examiner

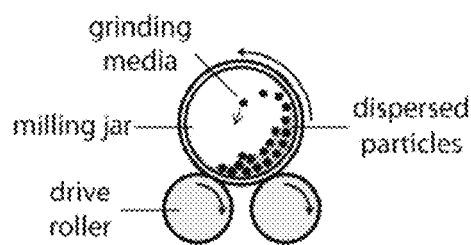 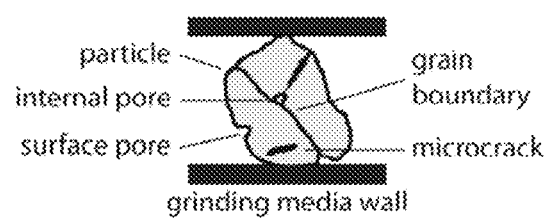
FIGURE 3A          FIGURE 3B

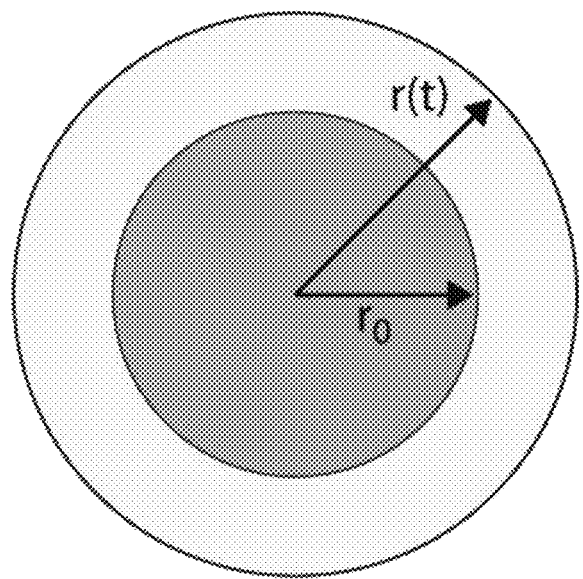
FIGURE 9

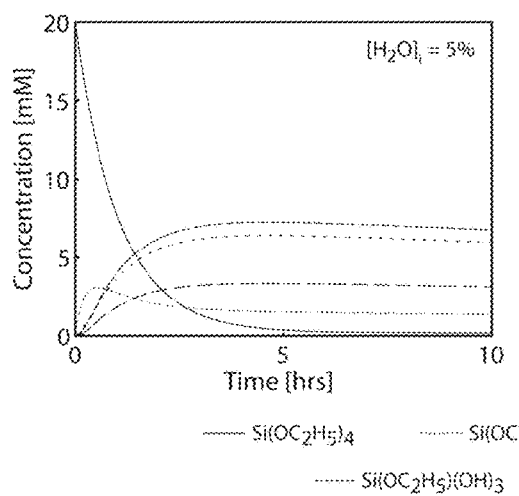
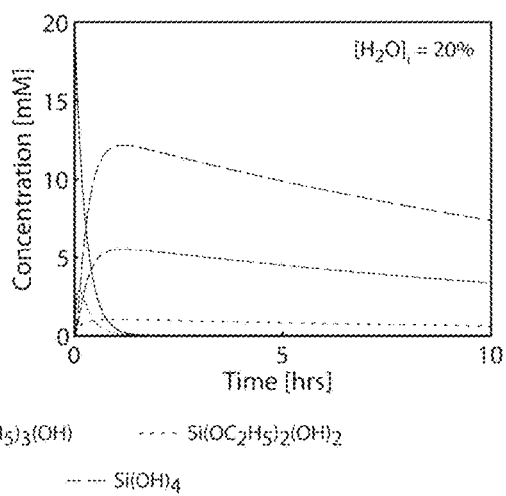
FIGURE 10A
FIGURE 10B

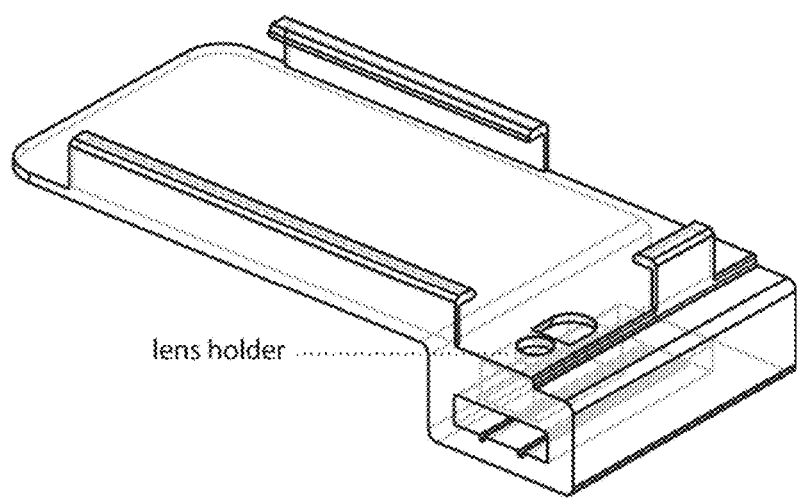
FIGURE 43A
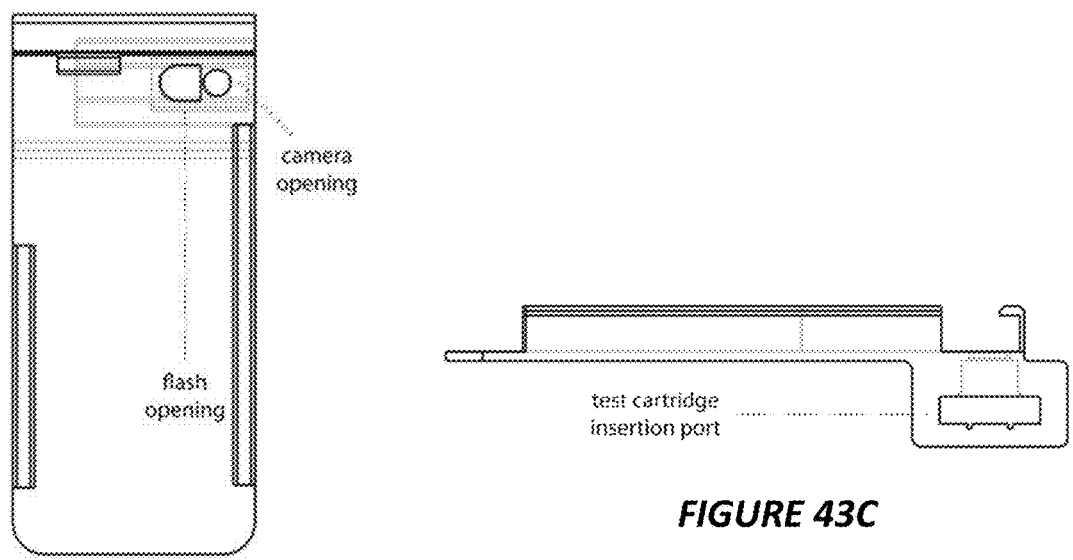
FIGURE 43C
FIGURE 43B

PHOSPHORESCENT REPORTERS

CROSS REFERENCE TO RELATED APPLICATIONS

This application claims priority to U.S. Provisional Patent Application No. 61/867,263, filed in the United States Patent and Trademark Office on Aug. 19, 2013, the entirety of which is hereby incorporated by reference.

STATEMENT REGARDING FEDERALLY SPONSORED RESEARCH

This invention was made with government support under Grant No. U54 AI057156, awarded by the National Institutes of Health. The government has certain rights in the invention.

BACKGROUND

Various tests and detection methodologies are used for specifically detecting numerous types of analytes in different application such as medical diagnostics, food safety and quality assurance, and environmental monitoring. Current methods and systems for utilizing analytical reporters have numerous limitations in terms of cost, efficiency, sensitivity, versatility and deployability in low-resource settings. Therefore, more effective technologies and sensing methods are desired to overcome these limitations.

SUMMARY

In some embodiments, the present disclosure pertains to new compositions of matter that comprise phosphorescent reporters. In some embodiments, the phosphorescent reporters are small phosphorescent particles, such as inorganic phosphors. In some embodiments, the inorganic phosphors have a luminescence lifetime greater than 10 microseconds, and preferably greater than a minute. In some embodiments, the inorganic phosphors have a lifetime long enough such that the particles can be briefly excited with a light source of suitable excitation wavelength, and then emit light at a longer wavelength than the excitation source at a high enough intensity and for a long enough period of time after excitation for time-resolved luminescence measurements or imaging.

In some embodiments, the phosphorescent reporters of the present disclosure comprise strontium aluminate. In some embodiments, the strontium aluminate is doped with europium and dysprosium ($SrAl_2O_4:Eu^{2+}, Dy^{3+}$) or combinations of one or more rare earth metals, preferably lanthanides. In some embodiments, the phosphorescent reporters of the present disclosure comprise inorganic phosphors created by suitable doping of rare earth or transition metals into an inorganic host material. In some embodiments, the inorganic host material may include, without limitation, zinc sulfide, calcium sulfide, alkaline earth silicates (e.g., beryllium, calcium, magnesium and barium silicates), alkaline earth aluminates (e.g., calcium aluminate, magnesium aluminate, beryllium aluminate, and barium magnesium aluminate), titanates (e.g., calcium, magnesium, and lead titanates), and combinations thereof. In some embodiments, the phosphorescent reporters of the present disclosure may include an inorganic metal oxide host material doped with a metal so as to alter the electronic structure, giving rise to phosphorescence.

In some embodiments, the phosphorescent reporters may be coated or encapsulated with a barrier or shell, such as a silicon-based shell (e.g., silicon oxide, silica, silicates, or organofunctional silanes), aluminum oxide, other inorganic metal-oxides, highly cross-linked polymer networks, and combinations thereof. In some embodiments, the coatings or encapsulations can help prevent loss or degradation of the luminescence properties of the phosphorescent core by reactions with water or chemicals, or compounds in the surrounding environment. In some embodiments, the coatings or encapsulations may be carried out by the Stöber process or modified variants of the Stöber process.

In some embodiments, the phosphorescent reporters of the present disclosure may be coated or functionalized with water soluble moieties like poly(ethylene glycol) or hydrophilic polymers in order for reporters to become easily dispersible in water or aqueous solutions. In some embodiments, the phosphorescent reporters may be coated or functionalized with moieties that reduce non-specific binding in analytical assays or tests.

In some embodiments the phosphorescent reporters of the present disclosure may be modified with molecular recognition elements, such as antibodies or aptamers. In some embodiments, the molecular recognition elements may be covalently attached to phosphorescent reporters. In some embodiments, the molecular recognition elements may be non-covalently attached to phosphorescent reporters, such as by physical adsorption.

In some embodiments, the phosphorescent reporters of the present disclosure may be associated with linkers, such as triethoxysilylbutyraldehyde (TESBA), poly (ethylene glycol) (PEG), (3-aminopropyl) triethoxysilane (APTES), alkanes, and the like. In some embodiments, reactive silane linkers that bond with a silica surface and also have functional groups for coupling to other molecules may be appended to the surface of phosphorescent reporters. In some embodiments, commercially available trialkoxysilane-polyethylene glycol molecules with reactive functional groups for coupling to proteins can be directly attached to an inorganic silica or alumina surface on a phosphorescent reporter. In some embodiments, linkers may be conjugated to a phosphorescent reporter before, during or after coating the phosphorescent reporter with water soluble moieties. For instance, in some embodiments, phosphorescent reporters may be coated with a reactive silane and subsequently conjugated with polyethylene glycols.

In some embodiments, the phosphorescent reporters may be functionalized with various functional groups on their surfaces. Exemplary functional groups include, without limitation, amine groups, carboxyl groups, aldehydes, ketones, hydroxyls, thiols, hydrazides, anhydrides, alkenes, alkynes, azides, and combinations thereof. In more specific embodiments, functionalized phosphorescent reporters can be directly coupled to aldehydes on antibodies created by oxidizing the polysaccharides on the $F_c$ portion of the antibody with periodate. In further embodiments, Protein A or other proteins that bind specifically to the $F_c$ portion of an antibody can be attached to the phosphorescent reporter surface, and then used to bind to an antibody in an oriented manner to improve the binding efficiency of the phosphorescent reporter.

In some embodiments, the phosphorescent reporters may be in the form of particles. In some embodiments, the particles may have sizes that range from about 1000 nm, 600 nm, 400 nm, 300 nm, 200 nm, 100 nm, or 50 nm.

Additional embodiments of the present disclosure pertain to methods of making the aforementioned phosphorescent reporters. In some embodiments, the method includes size reduction of inorganic phosphorescent powders through a combination of wet milling and settling. For instance, in some embodiments, wet milling is carried out with a ball mill or jar mill. A dry inorganic phosphorescent powder is then dispersed in a liquid and placed in a ceramic, metal, or plastic milling jar in the presence of grinding media (e.g., grinding media composed of a hard, dense material like zirconia) and milled.

In some embodiments, wet milling is carried out in the presence of organic solvents, such as ethyl acetate, toluene, cyclohexane, cyclopentane, decane, and combinations thereof. In some embodiments, the organic solvents are hydrophobic and have low hygroscopicity. In some embodiments, the organic solvents do not affect the luminescence of the inorganic materials. In some embodiments, wet milling is carried out in the presence of alcohols, such as ethanol, isopropanol, butanol, or combinations thereof.

In further embodiments, alternate milling techniques and instruments can be used to reduce the mean particle size of inorganic phosphorescent powders. In some embodiments, the techniques include, without limitation, cryo-milling, vibratory milling, bead milling, dry milling, attrition milling, jet milling, grinding, and combinations thereof. In some embodiments, fractionation techniques other than settling (e.g., sieving, field flow fractionation, tangential flow filtration) can be used to isolate narrower particle size distributions.

In some embodiments, the present disclosure pertains to a method for the detection of at least one analyte within a sample. Such a method comprises the step of providing a phosphorescent reporter. In some embodiments, the method further comprises contacting the phosphorescent reporter to the sample. In some embodiments the method comprises the step of detecting the luminescence signal of the phosphorescent reporter. In some embodiments the method comprises the step of determining the presence of an analyte and quantifying the analyte based on the detected luminescence signal.

In some embodiments, the present disclosure pertains to a method for the in vitro detection of at least one analyte within a sample. Such a method comprises the step of providing a phosphorescent reporter. In some embodiments the method further comprises loading the phosphorescent reporter into a porous material. In some embodiments, the method comprises contacting the sample with the porous material loaded with the phosphorescent reporter. In some embodiments, the method comprises allowing the sample and the phosphorescent reporter to flow through a porous membrane. In some embodiments, the method comprises detecting areas of luminescence or absence of luminescence on the membrane to indicate presence or absence of the at least one analyte.

In some embodiments the present disclosure pertains to a method for in vitro detection of at least one analyte within a sample. Such a method comprises the steps of providing a phosphorescent reporter; and providing at least one first molecular recognition element immobilized on a surface, where the immobilized molecular recognition element is capable of binding to the at least one analyte. In some embodiments, the method further comprises contacting the sample with the surface to allow binding of the at least one analyte to the molecular recognition element such that the analyte is immobilized. In some embodiments, the method comprises contacting the phosphorescent reporter with the surface to allow binding of the phosphorescent reporter to the at least one immobilized analyte; and measuring luminescence signal from the phosphorescent reporter to allow detection or quantification of the analyte.

In some embodiments, the surface comprises microfluidic chips, or paper microfluidics, or membranes, or microplates, or microbubbles for flotation, or transparent surfaces. In some embodiments, the phosphorescent reporter comprises at least one inorganic phosphorescent particle; a shell encapsulating the at least one phosphorescent particle; and a second molecular recognition moiety disposed on the shell. In some embodiments, the second molecular recognition moiety binds to the at least one immobilized analyte to generate the luminescent signal.

In some embodiments, the present disclosure relates to a magnetic phosphorescent reporter. In some embodiments, the magnetic phosphorescent reporter comprises at least one inorganic phosphorescent particle. In some embodiments, the magnetic phosphorescent reporter comprises a shell encapsulating the at least one inorganic phosphorescent particle and at least one magnetic moiety disposed on the shell. In some embodiments, the magnetic phosphorescent reporter comprises at least one molecular recognition moiety disposed on the shell. In some embodiments, the inorganic phosphorescent particle forms the core of the phosphorescent reporter.

In some embodiments, the magnetic phosphorescent reporter comprises least one inorganic phosphorescent particle and at least one magnetic particle or layer of magnetic material. In some embodiments, a shell encapsulates the at least one inorganic phosphorescent particle and the at least on magnetic particle or layer of magnetic material. In some embodiments, the magnetic phosphorescent reporter comprises at least one molecular recognition moiety disposed on the shell. In some embodiments, the inorganic phosphorescent particle and the at least one magnetic particle or magnetic layer form the core of the phosphorescent reporter.

In some embodiments, the present disclosure pertains to a method of detecting at least one analyte within a sample. Such a method comprises providing a magnetic phosphorescent reporter. In some embodiments, the magnetic phosphorescent reporter comprises at least one inorganic phosphorescent particle and at least one magnetic particle or layer of magnetic material. In some embodiments, the magnetic phosphorescent reporter further comprises a shell encapsulating the at least one inorganic phosphorescent particle and the at least one magnetic particle or layer of magnetic material. In some embodiments, the reporter comprises at least one first molecular recognition moiety specific to the analyte disposed on the shell.

In some embodiments, the method further comprises contacting the aforementioned magnetic phosphorescent reporter to the sample. In some embodiments, the method comprises concentrating the magnetic phosphorescent reporter by use of a magnetic field. In some embodiments, the method comprises contacting the concentrated magnetic phosphorescent reporter with a surface. In some embodiments, the surface is functionalized with at least one second molecular recognition moiety specific to the analyte. In some embodiments, the method further comprises detecting a luminescence signal of the magnetic phosphorescent reporter; and determining the presence of an analyte or quantifying the analyte based on the detected luminescence signal. In some embodiments, the first molecular recognition moiety binds to the at least one analyte to generate the luminescence signal In additional embodiments, the present disclosure pertains to methods of detecting the phosphorescent reporters in various settings, such as diagnostic settings (e.g., FIG. 31).

In some embodiments, the methods involve the detection of luminescence from the phosphorescent reporters. In some embodiments, luminescence from a phosphorescent reporter may be detected by excitation of the phosphorescent reporter. In various embodiments, the phosphorescent reporter may be excited by electrons, an electric field, photons, and combinations thereof. In some embodiments, luminescence may be detected simultaneously with excitation using wavelength-selective mechanisms. In some embodiments, the luminescence may be enhanced by the application of heat. In some embodiments, luminescence may be detected within 1, 10, 100, 1000, or 10,000,000 milliseconds of cessation of excitation. In some embodiments, luminescence may be detected by electronic mechanisms, optical mechanisms, optoelectronic mechanisms, mechanical shuttering, rotation, flow or repositioning mechanisms.

In some embodiments, luminescence is used to quantitatively or qualitatively obtain a signal in an assay by imaging with a film-based or digital camera (e.g., a digital camera with a CMOS, CCD or other type of sensor). In some embodiments, luminescence may be measured with a luminometer, fluorometer, spectrophotometer, or other similar instrument capable of measuring intensity of light.

In some embodiments, a cell phone, smart phone, or portable electronic device such as, but not limited to, a tablet, personal digital assistant, or laptop can be used to detect luminescence from the phosphorescent reporters for qualitative or quantitative assay readout. In some embodiments, a cell phone or portable electronic device may be coupled to an attachment to allow luminescence detection from phosphorescent reporters to test for the presence or absence of an analyte in a sample.

In some embodiments, the present disclosure pertains to methods for enhancing the detection of phosphorescent reporters. In some embodiments averaging techniques, such as those presented in FIGS. 36-40 are used to achieve a higher signal-to-noise ratio of the luminescence signal from phosphorescent reporters used in an assay for detecting the presence or absence of an analyte.

In some embodiments, the phosphorescent reporters of the present disclosure may be utilized in various assay settings. In some embodiments, the assay settings may include, without limitation, lateral flow, surface-bound assays, in flow through assays, assays associated with buoyant materials, or assays associated with magnetic materials for concentration or force stringency. In some embodiments, the present disclosure relates to compositions of matter comprising phosphorescent reporters and porous membranes such as, but not limited to, nitrocellulose, glass fibers, and cotton fibers. In some embodiments, the compositions of matter comprising phosphorescent reporters and porous membranes are used in assays for analyte detection.

BRIEF DESCRIPTION OF THE DRAWINGS

FIGS. 3A-3B shows various schemes. Schematic illustrating the milling process for size reduction of phosphorescent particles with a typical jar or ball mill (FIG. 3A). Drawing depicting the various defects of a particle that can lead to fracturing and size reduction during milling (FIG. 3B) (Adapted from Introduction the Principles of Ceramic Processing—J. Reed, 1988).

FIG. 9 shows the reaction of tetraethoxysilane (TEOS) and water to produce silica, and a schematic showing silica encapsulation of a phosphorescent particle of initial radius $r_0$ and a total radius $r(t)$ that increases with time as the silica layer grows.

FIGS. 10A-10B show model predictions of the transient concentrations of tetraethoxysilane and its hydrolysates during the silica encapsulation process. Two different initial conditions for the starting water concentration are shown. (Left) Initial water concentration of 5% by volume (FIG. 10A). (Right) Initial water concentration of 20% by volume (FIG. 10B).

FIG. 32A and FIG. 32B are independent trials.

In a single line scan, the test line is masked by noise, but the signal from the test line becomes readily distinguishable after reducing the noise by averaging multiple line scans.

Figure 39A:
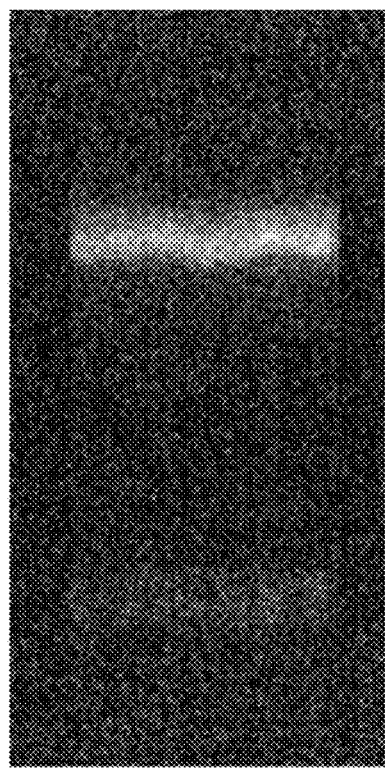
Figure 39B:
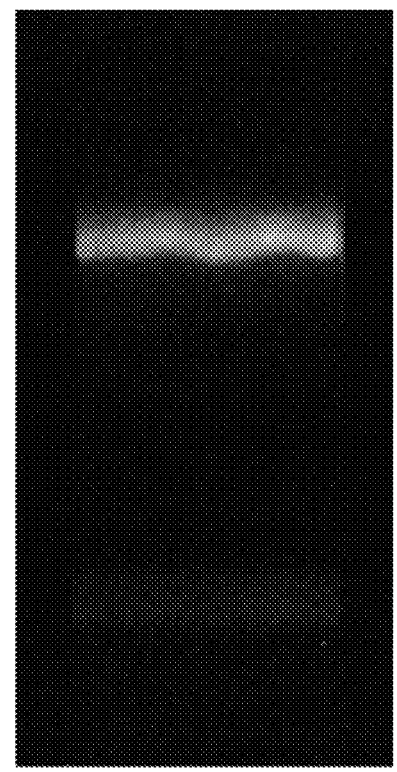

FIGS. 39A-39B shows grayscale images acquired with an iPhone 5s of an LFA strip run with 0.1 ng/mL biotinylated lysozyme and NeutrAvidin phosphorescent reporters. FIG. 39A shows a single image. FIG. 39B shows an average of 16 images.

Figure 40A:
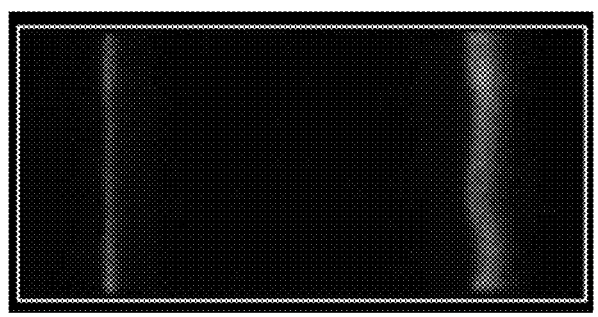
Figure 40B:
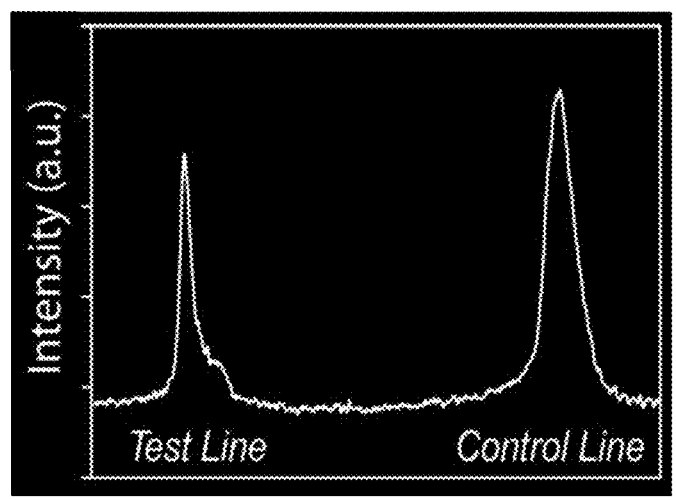

FIGS. 40A-40B show LFA results for NeutrAvidin phosphorescent reporters detecting 1 ng/mL biotinylated lysozyme. The average image of 40 RGB color images acquired with an iPhone 5s (FIG. 40A). Corresponding intensity profile (FIG. 40B).

Figure 41A:
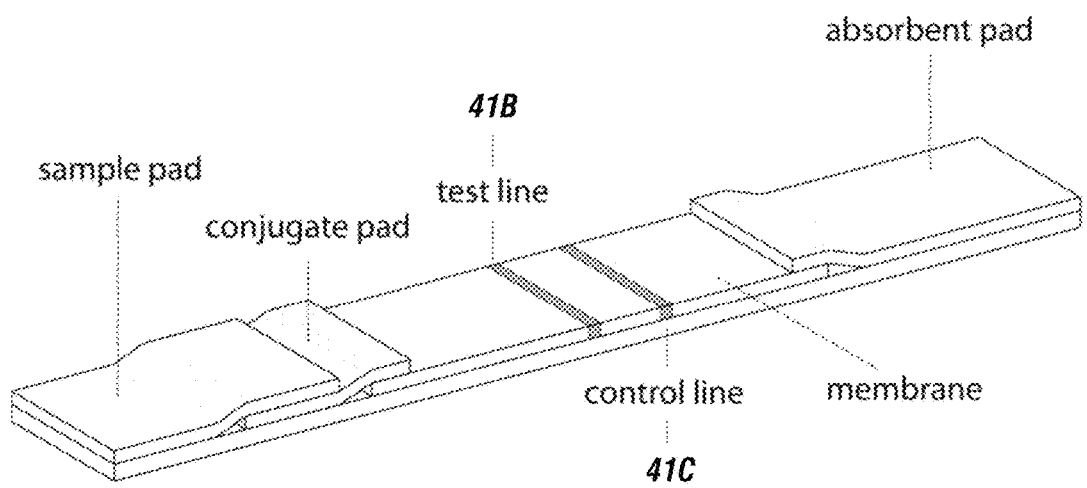
Figure 41B:
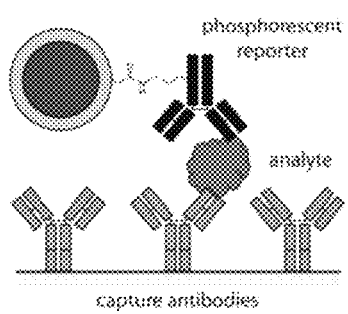
Figure 41C:
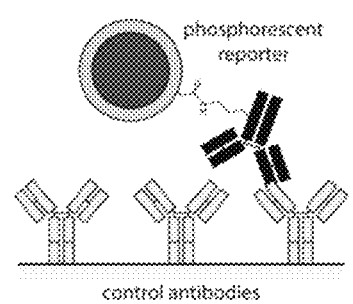

FIGS. 41A-41C show the preferred method and embodiment of the present invention for detecting analytes. Phosphorescent reporters are applied in a lateral flow assay, binding at the test line in the presence of an analyte. A control line ensures that the assay functioned properly. Phosphorescent reporters are loaded into a conjugate pad, which is connected to a sample pad. An absorbent pad acts as a sink to help wick liquid through the test strip.

Figure 42A:
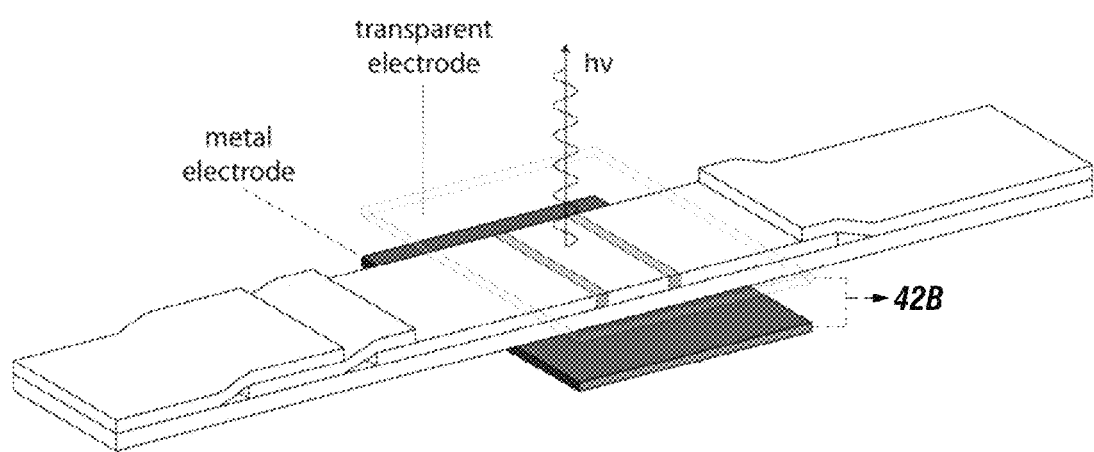
Figure 42B:
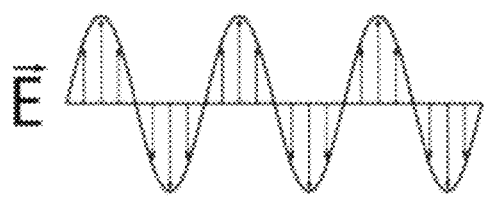

FIGS. 42A-42B show a lateral flow assay with electroluminescence readout. The lateral flow strip is sandwiched either partially or entirely between two electrodes, at least one of which is transparent to allow transmission of light. A constant or alternating electric field is applied between the electrodes, stimulating the phosphorescent reporters to emit luminescence.

FIGS. 43A-43C show an example of a cell phone attachment to allow time-gated luminescence imaging of assays or tests that incorporate phosphorescent reporters using the phone's native optical hardware. The attachment, in part, is similar to a protective phone case, and the phone simply slides into the attachment. A test cartridge is loaded into the insertion port of the attachment, and the region of interest within the test cartridge lines up with the camera of the phone. The flash from the light(s) built into the phone is used for photoexcitation of the phosphorescent reporters. The attachment can also incorporate one or more lenses that line up with the optics of the camera in the phone to allow magnification, increased sensitivity, or a decreased working distance. The attachment can also contain elements such as reflective surfaces that redirect the light from the phone in a manner that improves excitation of the phosphorescent reporters.

DETAILED DESCRIPTION

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise. Parameters disclosed herein (e.g., temperature, time, concentrations, etc.) may be approximate.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Many technologies and assay formats in biosensing and analytical chemistry involve the use of reporters or labels to transduce the specific binding of an analyte to a molecular recognition moiety into an observable signal. The analytical sensitivity or limit of detection of an assay, therefore, depends strongly on the detectability of the signal generated by the reporter. Reporter technologies vary broadly in composition and the mechanisms of signal generation, which affects sensitivity, linearity, and stability, making some classes of reporters better suited to particular applications than others.

Currently, some of the more robust and widely used point-of-care testing formats are membrane-based, such as the lateral flow assay (LFA) or the flow through assay. These tests use a membrane functionalized with molecular recognition elements to specifically bind to and capture one or more analytes, and colored submicron particles, such as gold nanoparticles or dyed latex particles, bind to the captured analyte allowing visual readout of the test results. These colorimetric reporters, however, limit the assay sensitivity, and tests using the same system of recognition moieties with different reporters, such as enzymes, are able to provide superior detection limits. Other reporters such as fluorescent nanoparticles can provide better linearity between the measured signal and analyte concentration in addition to an improved limit of detection.

Despite these advantages, high sensitivity reporter technologies possess multiple problems that prohibit their widespread adoption in point-of-care settings. Enzymes are prone to denaturation, leading to loss in activity over time. Furthermore, many enzymes use substrates that require refrigeration or storage conditions that are not amenable to field-use. Almost all fluorescent dyes are prone to photobleaching, and many are prone to chemical degradation.

Significant effort in industry and academia has been made toward improving analytical assays by developing various reporters including gold nanoparticles, fluorescent labels, quantum dots, up-converting phosphors, magnetic nanoparticles, and others. Reporters that use photoluminescence for the signal readout like fluorescent nanoparticles or quantum dots can enhance the sensitivity of assays compared to conventional labels like gold nanoparticles, and also tend to be more stable than enzymatic reporters. Most photoluminescence reporters require a continuous source of excitation light for imaging and quantitative measurements, as the excited state lifetime is usually short (e.g. 10 ns for organic fluorescent dyes). Optical emission filters are not perfectly efficient at blocking the excitation light from transmitting to the detector, and many materials used in assays, such as lateral flow or flow through membranes, in addition to biological sample matrices, exhibit some autofluorescence. Background autofluorescence reduces the signal-to-noise ratio, and as a result often hampers the sensitivity or limit of detection of assays. Time-resolved photoluminescence can further improve the sensitivity of assays by allowing background autofluorescence to decay after switching the excitation source off, and carrying out delayed imaging or quantitative measurements, thereby increasing the signal-to-noise ratio. Time-resolved measurements, however, require that the probe remain in an excited state longer than the decay time of the background autofluorescence.

Phosphorescent organic dyes, organometallic complexes, and metal chelates typically have longer excited state lifetimes than fluorescent probes and quantum dots, and have been used in time-resolved assays for detection of analytes. Phosphorescent organometallic dyes and metal chelates, however, are generally expensive and are prone to photobleaching, which can compromise reliability in diagnostic assays. Furthermore, these phosphorescent dyes have emission lifetimes that are still relatively short, on the order of 10 µs to 1 ms. Therefore, time-resolved photoluminescence assays with metal chelate or organometallic phosphorescent reporters requires carefully designed instrumentation with fast response times and precisely controlled time-delays between excitation and measurement.

Laboratory-based and point-of-care tests that utilize photoluminescence for analyte detection often have limited sensitivity with certain sample types due to autofluorescence from non-analyte molecules in the sample matrix. Up-converting phosphors that emit visible light upon infrared or near-infrared excitation overcome the problem of autofluorescence from the sample matrix. However, up-converting phosphors have low quantum yields, and therefore require intense light sources such as laser diodes for excitation, and typically require the use of complex systems with relatively expensive optical hardware to achieve desirable sensitivity. Virtually all photoluminescent reporters that have short emission lifetimes require continuous excitation for readout, and thus, optical filters are needed to reduce the intensity of the background signal from scattered excitation light.

Time-gated photoluminescence can overcome autofluorescence issues by using a reporter with a relatively long emission lifetime compared to fluorescence (e.g. 100 µs vs 10 ns), and introducing a time delay between excitation and measurement to allow the non-specific background signal to decay. Additionally, time-gated photoluminescence can allow one to construct a device without the requirement of optical filters, as the scattered excitation light also rapidly decays during the time delay. However, the existing reporters for time-gated photoluminescence require precisely defined and relatively short time delays from 10-50 µs for optimal sensitivity, as the emission lifetimes of the typical organometallic dyes or metal chelates in these reporters range from 100-500 µs. Therefore, it would be difficult to implement time-gated photoluminescence using these reporters and the optoelectronics systems built in to many consumer devices such as cameras in cell phones and tablet computers.

Inorganic phosphorescent materials such as alkaline earth aluminates doped with rare earth metals or transition metals have found use in luminescent displays and paints. Inorganic phosphors have significantly longer emission lifetimes and higher chemical and optical stability than many of the reporters used in biosensing and analytical chemistry. These properties make inorganic phosphors attractive candidates for overcoming the issues with reporters in the prior art. However, the prior art fails to teach methods for preparing reporters based on such materials for analyte detection applications, nor does it demonstrate how to utilize the optical properties of these materials for highly sensitive detection.

Inorganic, ceramic, or crystalline solid materials that emit light upon stimulation with an energy source such as, but not limited to, photons, electrons, electric fields, or heat are generally referred to as phosphors or phosphorescent materials. The term "phosphorescence," in the context of inorganic, ceramic, or crystalline solids, is not to be confused with the physical phenomenon of phosphorescence occurring in or associated with organic dyes or molecules, organometallic compounds or molecules, or metal chelate complexes. In the present disclosure, the terms "phosphorescence", "phosphorescent", and phosphor refer to inorganic, ceramic, or crystalline solid material, unless specifically stated otherwise. In the present disclosure, the terms "phosphorescence", "long-term phosphorescence", and "persistent luminescence", are all terms used interchangeably to describe the phenomenon in which an inorganic, ceramic, or crystalline solid material, emits light for long periods of time, in the order of microseconds to hours, after stimulation with an energy source as mentioned herein.

Persistent luminescence nanoparticles or microparticles that emit light for several milliseconds to several hours after excitation present a new and potentially vast improved way to design qualitative and quantitative assays with luminescence readout and enhanced sensitivity due to significantly lower background autofluorescence, and with minimal optical hardware. Additionally, inorganic persistent luminescence nanoparticles are typically much more resistant to photobleaching than fluorescent dyes, phosphorescent organic and organometallic dyes or compounds, and even quantum dots.

In an embodiment, the present disclosure pertains to a phosphorescent reporter comprising at least one inorganic phosphorescent particle. In some embodiments, the inorganic phosphorescent particle is encapsulated by a shell. In some embodiments, at least one molecular recognition moiety is disposed on the shell. In some embodiments, the inorganic phosphorescent particle forms the core of the phosphorescent reporter. In some embodiments, the phosphorescent reporter binds via the at least one molecular recognition moiety to a target analyte to generate a luminescence signal. In some embodiments, the luminescence signal is detected by excitation of the at least one inorganic phosphorescent particle. In some embodiments, the excitation of the at least one inorganic phosphorescent particle is achieved by UV light, or visible light, or other photons of the electromagnetic spectrum. In some embodiments, the at least one inorganic phosphorescent particle has a luminescence lifetime ranging from about 10 microseconds to about an hour. In some embodiments, the at least one inorganic phosphorescent particle has a luminescence lifetime of several hours.

In some embodiments, the at least one inorganic phosphorescent particle comprises an inorganic host material doped with at least one rare earth metal or at least one transition metal. In some embodiments, the at least one inorganic host material is zinc sulfide, or calcium sulfide, or alkaline earth silicates, or alkaline earth aluminates, or titanates. In some embodiments, the alkaline earth silicates are selected from a group consisting of beryllium silicate, calcium silicate, magnesium silicate, and barium silicate. In some embodiments, the alkaline earth aluminates are selected from a group consisting of strontium aluminate, calcium aluminate, magnesium aluminate, beryllium aluminate, and barium magnesium aluminate. In some embodiments, the titanates are selected from the group consisting of calcium titanate, magnesium titanate, and lead titanate. In some embodiments, the at least one inorganic phosphorescent particle comprises strontium aluminate doped with at least one rare earth metal. In some embodiments, the at least one rare earth metal comprises europium, or dysprosium, or lanthanides or a combination thereof. In some embodiments, the at least one inorganic phosphorescent particle comprises an inorganic metal oxide host material doped with a metal.

In some embodiments, the shell encapsulating the at least one inorganic phosphorescent particle comprises a silicon-based coating. In some embodiments, the silicon-based coating is selected from the group consisting of silicon oxide, silica, silicates, and organofunctional silanes. In some embodiments, the shell encapsulating the at least one inorganic phosphorescent particle comprises a hydrophilic polymer. In some embodiments, the hydrophilic polymer is polyethylene glycol.

In some embodiments, the molecular recognition moiety comprises an antibody, or an antibody fragment, or an antigen, or nucleic acid, or peptide, or an aptamer. In some embodiments, the molecular recognition moiety comprises linkers disposed on the shell encapsulating the at least one inorganic phosphorescent particle. In some embodiment, the linkers are selected from the group consisting of triethoxysilylbutyraldehyde (TESBA), polyethylene glycol (PEG), homobifuctional polyethylene glycol, heterobifunctional polyethylene glycol (3-aminopropyl) triethoxysilane (APTES), and trialkoxysilanes. In some embodiments, the linkers further comprise a functional group for coupling to a target molecule. In some embodiments, the molecular recognition moiety comprises functional groups disposed directly on the shell. In some embodiments, the functional groups are selected from the group consisting of amine groups, carboxyl groups, aldehydes, ketones, hydroxyls, thiols, and hydrazide, anhydrides, alkynes, and azides. In some embodiments, the at least one inorganic phosphorescent particle is a nanoparticle. In some embodiments, the size of the phosphorescent reporter is from about 10 nm to about 1000 nM.

In some embodiments, the present disclosure relates to a method of making a phosphorescent reporter comprising preparing inorganic phosphorescent particles. In some embodiments, the method involves encapsulating the inorganic phosphorescent particles in a shell. In some embodiment, the method relates to disposing at least one molecular recognition moiety on the shell. In some embodiments, the inorganic phosphorescent particles form the core of the phosphorescent reporter. In some embodiments, the step of preparing inorganic phosphorescent particles comprises size reduction of inorganic phosphorescent powders. In some embodiments, the size reduction comprises wet milling, or cryo-milling, or vibratory milling, or bead milling, or dry milling, or attrition milling, or jet milling, or grinding, or a combination thereof. In some embodiments, the size reduction is by wet milling and fractionation. In some embodiments, the wet milling is carried out in presence of organic solvents or alcohols. In some embodiments, the organic solvent is selected from the group consisting of ethyl acetate, toluene, cyclohexane, cyclopentane, and decane. In some embodiments, the alcohol is ethanol, or isopropanol, or butanol.

In some embodiments, the step of encapsulating the inorganic phosphorescent particles uses the Stöber process or modified variants of the Stöber process. In some embodiments, the step of disposing a molecular recognition moiety is performed before, during, or after the encapsulation step. In some embodiments, the step of disposing the at least one molecular recognition is by physical adsorption or by covalent linkage. In some embodiments, the step of disposing the at least one molecular recognition moiety comprises functionalization of the surface of the shell with at least one linker molecule. In some embodiments, the at least one linker molecule is selected from the group consisting of triethoxysilylbutyraldehyde (TESBA), polyethylene glycol (PEG), (3-aminopropyl)triethoxysilane (APTES), and trialkoxysilanes. In some embodiments, the at least one linker molecule has at least one functional group for coupling to the at least one molecular recognition moiety. In some embodiments, the at least one functional group is selected from the group consisting of amine groups, carboxyl groups, aldehydes, ketones, hydroxyls, thiols, hydrazides, anhydrides, azides, and alkynes. In some embodiments, the step of disposing at least one molecular recognition moiety further comprises conjugating the linker molecule with a molecular recognition moiety via the functional group. In some embodiments, the molecular recognition moiety comprises an antibody, an antibody fragment, an antigen, nucleic acid, peptide, protein, or an aptamer. In some embodiments, the step of disposing a molecular recognition moiety comprises at least one functional group disposed directly on the shell. In some embodiments, the functional group is coupled to one end of at least one polyethylene glycol chain. In some embodiments, the other end of the polyethylene glycol chain is coupled to the at least one molecular recognition moiety.

In some embodiments, the present disclosure pertains to a method for the detection of at least one analyte within a sample. Such a method comprises the step of providing a phosphorescent reporter. In some embodiments, the method further comprises contacting the phosphorescent reporter to the sample. In some embodiments the method comprises the step of detecting the luminescence signal of the phosphorescent reporter. In some embodiments the method comprises the step of determining the presence of an analyte and quantifying the analyte based on the detected luminescence signal.

In some embodiments, the present disclosure pertains to a method for the in vitro detection of at least one analyte within a sample. Such a method comprises the step of providing a phosphorescent reporter. In some embodiments the method further comprises loading the phosphorescent reporter into a porous material. In some embodiments, the method comprises contacting the sample with the porous material loaded with the phosphorescent reporter. In some embodiments, the method comprises allowing the sample and the phosphorescent reporter to flow through a porous membrane. In some embodiments, the method comprises detecting areas of luminescence or absence of luminescence on the membrane to indicate presence or absence of the at least one analyte. In some embodiments, the method further comprises quantification of the detected analyte.

In some embodiments the present disclosure pertains to a method for in vitro detection of at least one analyte within a sample. Such a method comprises the steps of providing a phosphorescent reporter; and providing at least one first molecular recognition element immobilized on a surface, where the immobilized molecular recognition element is capable of binding to the at least one analyte. In some embodiments, the method further comprises contacting the sample with the surface to allow binding of the at least one analyte to the molecular recognition element such that the analyte is immobilized. In some embodiments, the method comprises contacting the phosphorescent reporter with the surface to allow binding of the phosphorescent reporter to the at least one immobilized analyte; and measuring luminescence signal from the phosphorescent reporter to allow detection or quantification of the analyte. In some embodiments, the surface comprises microfluidic chips, or paper microfluidics, or membranes, or microplates, or microbubbles for flotation, or transparent surfaces. In some embodiments, the phosphorescent reporter comprises at least one inorganic phosphorescent particle; a shell encapsulating the at least one phosphorescent particle; and a second molecular recognition moiety disposed on the shell. In some embodiments, the second molecular recognition moiety binds to the at least one immobilized analyte to generate the luminescent signal. In some embodiments, the luminescence from the phosphorescent reporter is detected by providing a light source suitable for photoexcitation of the phosphorescent reporter; providing a sensor capable of detecting luminescence from the phosphorescent reporter; illuminating the phosphorescent reporter with the light source; turning off the light source; waiting for a defined period of time to allow decay of the background; and measuring emitted luminescence from the phosphorescent reporter.

In some embodiments, the present disclosure relates to a magnetic phosphorescent reporter. In some embodiments, the magnetic phosphorescent reporter comprises at least one inorganic phosphorescent particle. In some embodiments, the magnetic phosphorescent reporter comprises a shell encapsulating the at least one inorganic phosphorescent particle and at least one magnetic moiety disposed on the shell. In some embodiments, the magnetic phosphorescent reporter comprises at least one molecular recognition moiety disposed on the shell. In some embodiments, the inorganic phosphorescent particle forms the core of the phosphorescent reporter.

In some embodiments, the magnetic phosphorescent reporter comprises least one inorganic phosphorescent particle and at least one magnetic particle or layer of magnetic material. In some embodiments, a shell encapsulates the at least one inorganic phosphorescent particle and the at least on magnetic particle or layer of magnetic material. In some embodiments, the magnetic phosphorescent reporter comprises at least one molecular recognition moiety disposed on the shell. In some embodiments, the inorganic phosphorescent particle and the at least one magnetic particle or magnetic layer form the core of the phosphorescent reporter.

In some embodiments, the present disclosure pertains to a method of detecting at least one analyte within a sample. Such a method comprises providing a magnetic phosphorescent reporter. In some embodiments, the magnetic phosphorescent reporter comprises at least one inorganic phosphorescent particle and at least one magnetic particle or layer of magnetic material. In some embodiments, the magnetic phosphorescent reporter further comprises a shell encapsulating the at least one inorganic phosphorescent particle and the at least one magnetic particle or layer of magnetic material. In some embodiments, the reporter comprises at least one first molecular recognition moiety specific to the analyte disposed on the shell.

In some embodiments, the method further comprises contacting the aforementioned magnetic phosphorescent reporter to the sample. In some embodiments, the method comprises concentrating the magnetic phosphorescent reporter by use of a magnetic field. In some embodiments, the method comprises contacting the concentrated magnetic phosphorescent reporter with a surface. In some embodiments, the surface is functionalized with at least one second molecular recognition moiety specific to the analyte. In some embodiments, the method further comprises detecting a luminescence signal of the magnetic phosphorescent reporter; and determining the presence of an analyte or quantifying the analyte based on the detected luminescence signal. In some embodiments, the first molecular recognition moiety binds to the at least one analyte to generate the luminescence signal.

Strontium aluminate doped with europium and dysprosium ($SrAl_2O_4:Eu^{2+}$, $Dy^{3+}$) is a long-lifetime inorganic phosphor with observable luminescence for several hours after excitation. It has a higher emission intensity than the more common commercial phosphors like doped zinc sulfide phosphors, making it an ideal material for labels in in vitro diagnostics and other binding assays. Strontium aluminate has the additional advantage of being highly photostable, allowing test strips or other assays that use the phosphors to be re-imaged at later times without significant loss of luminescence and sensitivity, allowing reliable secondary confirmation of assay results. Photostability of the reporter also helps ensure consistency between assays, and can prolong the shelf-life of a diagnostic kit that uses luminescent labels.

In some embodiments, the present disclosure pertains to a process of making strontium aluminate phosphors for diagnostic assays, such as diagnostic immunoassays or nucleic acid hybridization assays.

Figure 1:
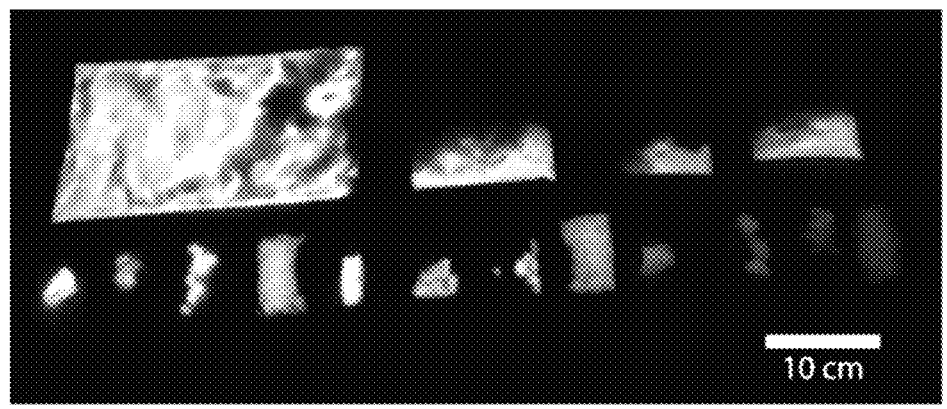
FIG. 1 shows different samples of strontium aluminate phosphorescent powder that emit at different wavelengths. The different colors of the material can allow for spectral-based multiplexed assays.

In some embodiments, the present disclosure pertains to phosphorescent strontium aluminate powders. FIG. 1 shows strontium aluminate phosphor samples of varying grain size and emission wavelength imaged in the dark. Solid state synthesis recipes for producing phosphors result in large chunks of the material that can be ground using equipment like crushers and rollers in combination with sieves of a specific mesh size in order to obtain finer material needed for typical applications like glow-in-the-dark paint.

Optical microscopy images (FIG. 5A) of the finest grade phosphors purchased revealed that most of the material was confined in particles with effective diameters much greater than 10 μm, which is too large for most assay formats as the Stokes settling velocities are too rapid (e.g. 150 μm/s in water for a 10 μm sphere of strontium aluminate). In order to use phosphorescent reporters in most assay formats, it is desirable for the particles to be substantially smaller than the finest grade commercial material, such that the particles are easily suspended in buffers or other liquids.

In some embodiments, a typical mortar and pestle may be used to reduce the bulk of the commercial powder to submicron dimensions. In some embodiments, a wet milling process may be used to reduce the mean particle size to submicron dimensions (FIG. 3). In some embodiments, the fine grade commercial powder can be suspended in an anhydrous or hydrophobic solvent with suitable grinding media in a milling jar and placed on a mill for an extended period of time (e.g., up to 9 days).

In some embodiments, wet milling is desirable for effective size reduction, as dry milling may result in densely packed agglomerates of powder on the sides of the milling jar which keeps a large fraction of the material isolated from the milling process. In some embodiments, keeping the particles suspended in solution helps ensure that almost all of the material are evenly milled. Many inorganic phosphors are prone to hydrolysis so an anhydrous or hydrophobic liquid is desirable in some embodiments to reduce particle size while preserving the luminescence properties of the particles.

Figure 4A:
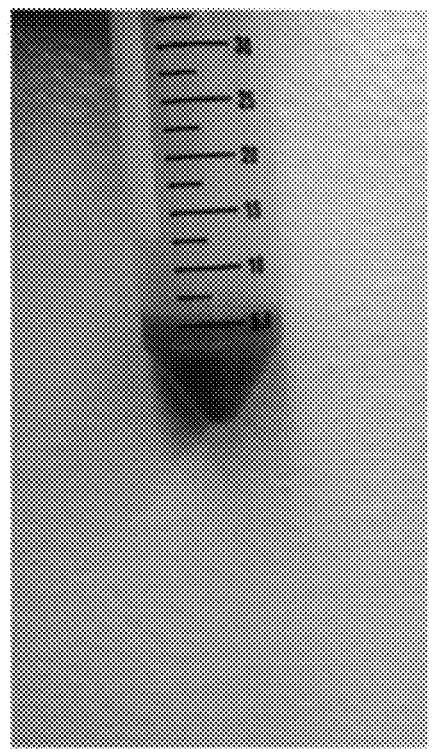
FIGS. 4A-4B show images of strontium aluminate phosphorescent powder after wet milling in ethanol in a stainless steel milling jar with a Retsch MM301 High Speed Mixer Mill. Strontium aluminate proved too abrasive to the steel milling ball and jar, resulting in significant contamination of the product with steel particles, giving rise to the grey color. Experiments were carried out with other milling fluids to ensure the contamination was a mechanical effect from physical abrasion to the steel, and not a chemical phenomenon.
Figure 4B:
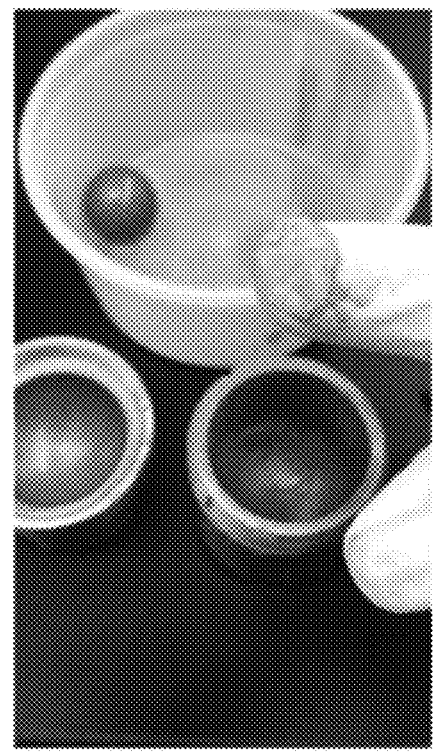

Applicants have discovered that the relative hardness of the material undergoing comminution through the milling jar and grinding media is an important factor that influences the performance of the milling process. In some embodiments, Applicants used two different mills, a U.S. Stoneware ball mill and a Retsch MM301 High Speed Mixer mill. The high speed mixer mill used a stainless steel milling jar and a 2 cm stainless steel milling ball as the grinding media, which proved ineffective at reducing the particle size as the strontium aluminate was highly abrasive to the steel and resulted in contamination (FIGS. 4A-4B). Additionally, even trace levels of some elements can effectively kill the luminescence of inorganic solids, as is the case with iron in zinc sulfide phosphors, which must be considered when selecting the grinding media and milling jar. An image of a colloidal dispersion of milled phosphors displaying bright photoluminescence and the corresponding emission spectrum is presented in FIG. 7.

Figure 5A:
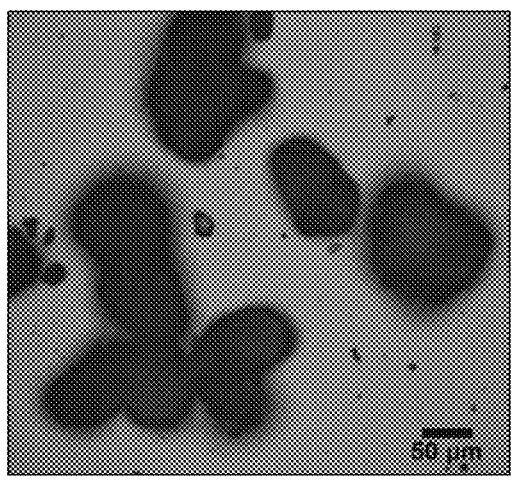
FIGS. 5A-5B show optical microscopy images of strontium aluminate phosphorescent particles. The finest grade commercial strontium aluminate powders, with effective particle diameters over 50 μm (FIG. 5A). Strontium aluminate phosphorescent particles after wet milling, yielding particles below 10 μm in diameter (FIG. 5B).
Figure 5B:
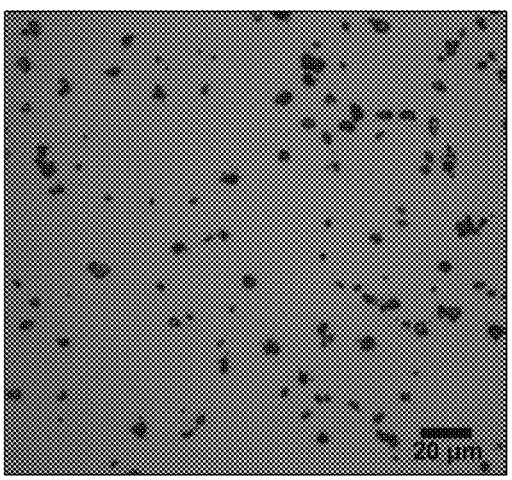

The U.S. Stoneware mill used a ceramic jar and zirconia grinding media, and proved much more effective at reducing the particle size without contamination when wet milling was carried out with roughly 5 grams of strontium aluminate powder suspended in 50 mL of ethyl acetate. FIGS. 5A-5B show optical microscopy images of as-purchased phosphorescent powder and extensive size reduction after 24 hours of wet milling.

Figure 6:
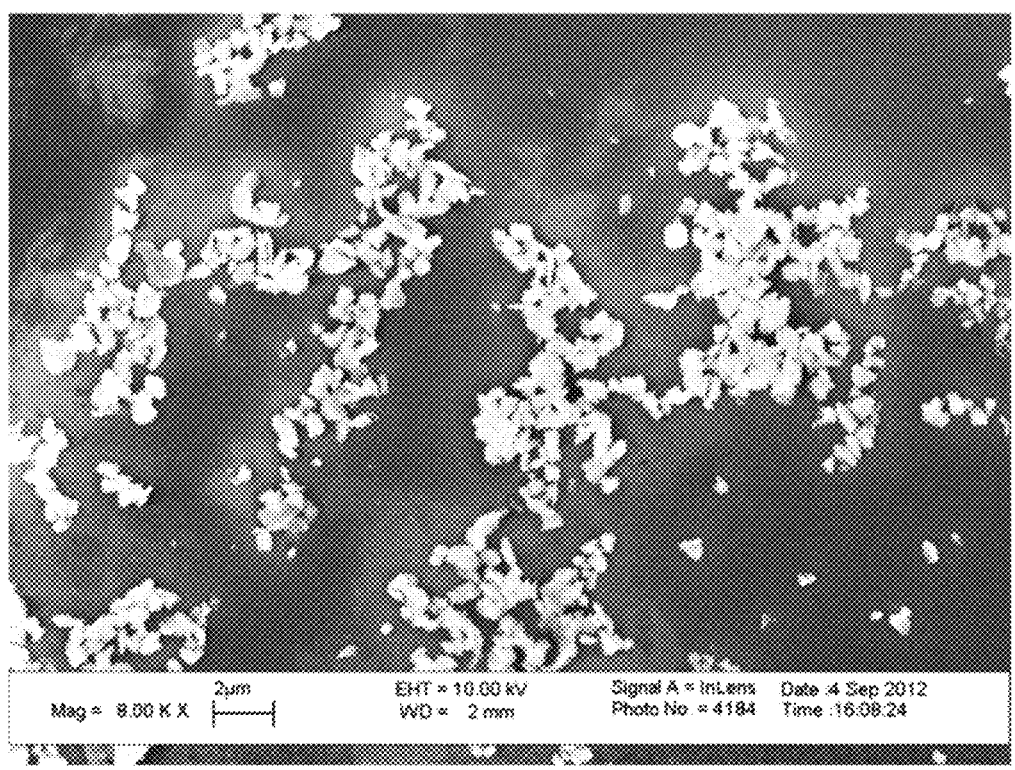
FIG. 6 shows a scanning electron microscopy (SEM) image of milled strontium aluminate phosphorescent particles. A sizeable fraction of the particles have submicron diameters.
Figure 7:
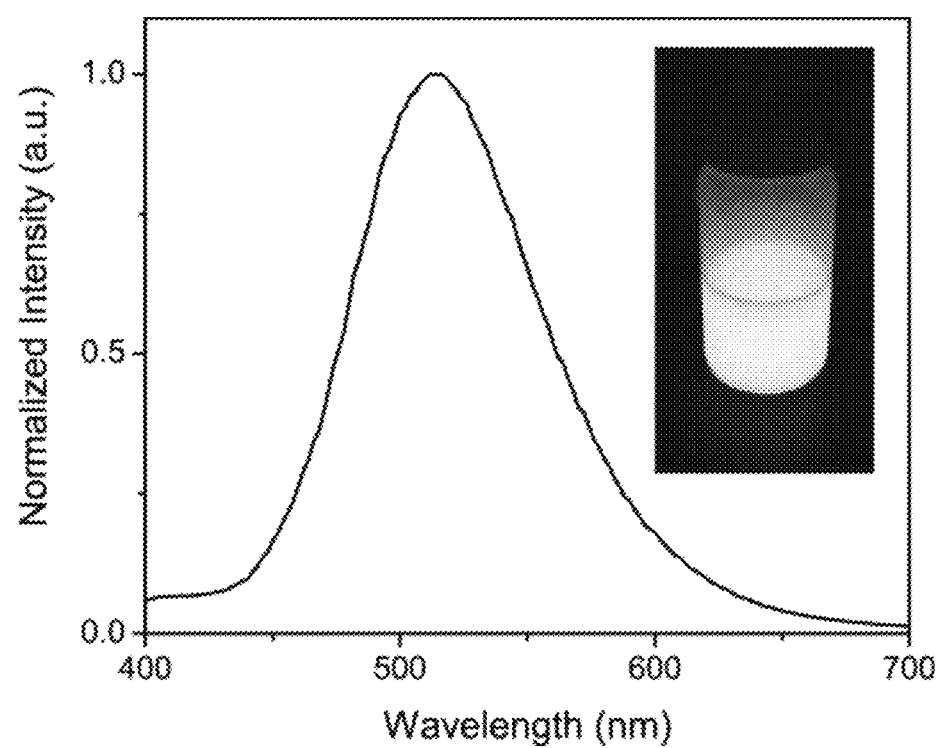
FIG. 7 shows the emission spectrum of green strontium aluminate phosphors, and a photograph of a colloidal dispersion of milled phosphorescent particles taken several seconds after excitation. The milled particles do not settle rapidly, and also retain a long luminescence lifetime.
Figure 8:
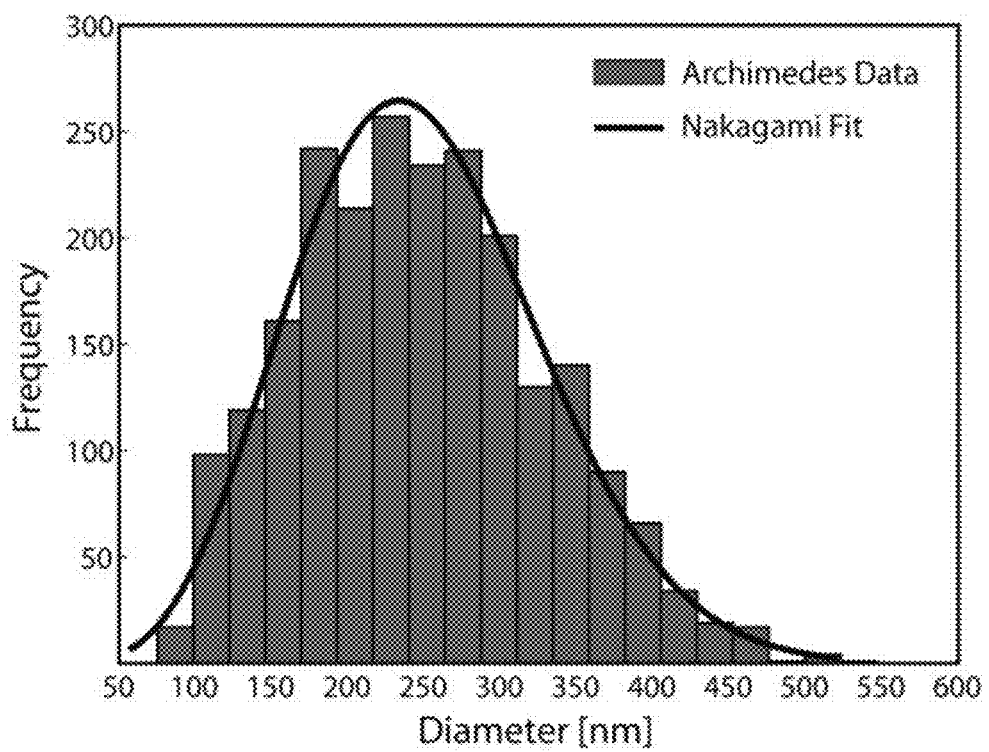
FIG. 8 shows a particle size distribution of milled and size-fractionated strontium aluminate phosphors. The data were acquired with a suspended microchannel resonator instrument.

Scanning electron microscopy (SEM) revealed many submicron particles after approximately a week of wet milling (FIG. 6). Differential settling with a centrifuge was used to remove the larger particles and isolate fractions with narrower size distributions. The milling and fractionation processes allow isolation of small particles that do not rapidly settle in liquids, and still retain their persistent luminescence properties (FIG. 7). A combination of milling and fractionation can achieve relatively narrow size distributions of nanometer-sized particles (FIG. 8).

Figure 11:
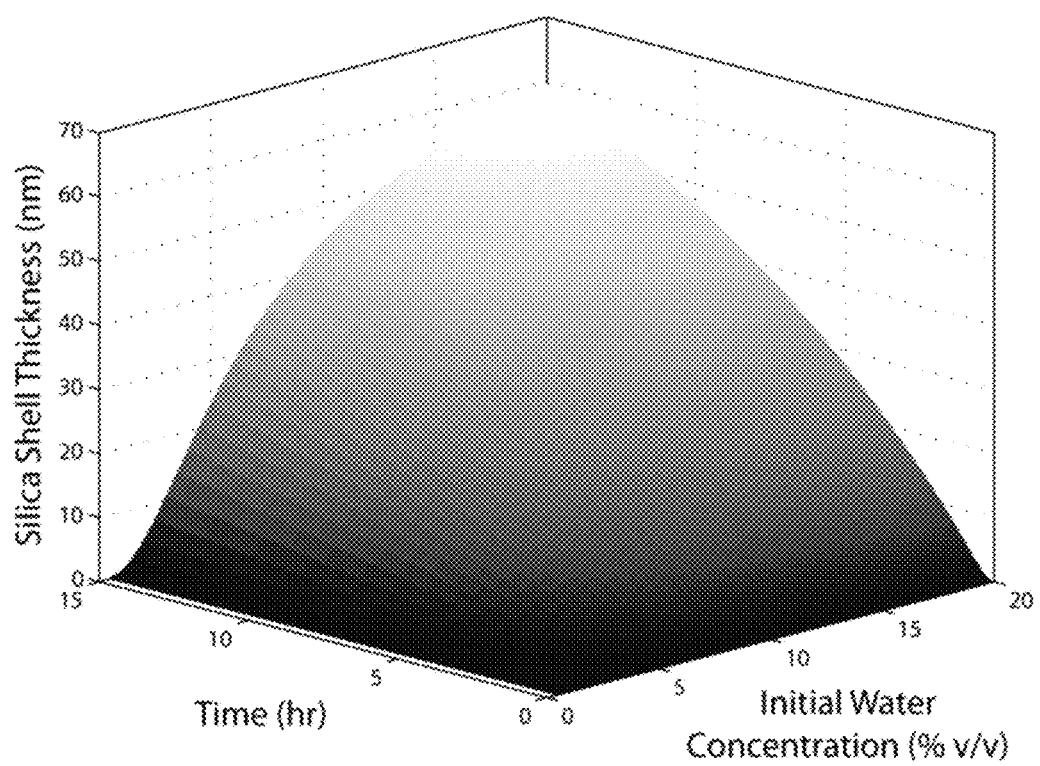
FIG. 11 shows the calculated silica shell thickness around a particle with a 500 nm initial diameter as a function of time and for different initial conditions for the starting water concentration.
Figure 12A:
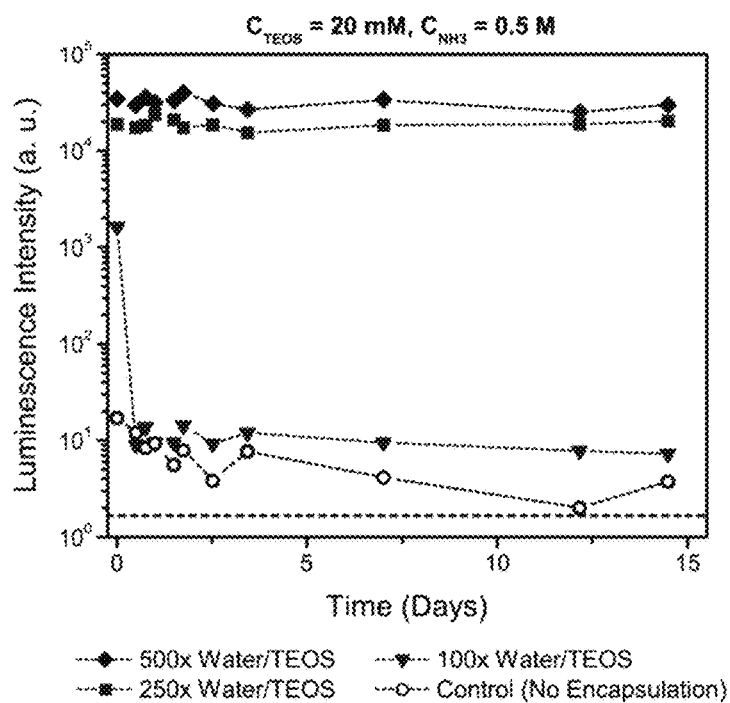
FIGS. 12A-12B show results of silica encapsulation experiments with different molar ratios of water to tetraethoxysilane. Particles subjected to different encapsulation protocols were resuspended in pure water to form colloids of the same concentration, and luminescence was measured as a function of time to observe the effectiveness of the silica shell on preventing hydrolysis. 20 mM tetraethoxysilane, 0.5 M ammonia (FIG. 12A), 40 mM tetraethoxysilane, 0.5 M ammonia (FIG. 12B).
Figure 12B:
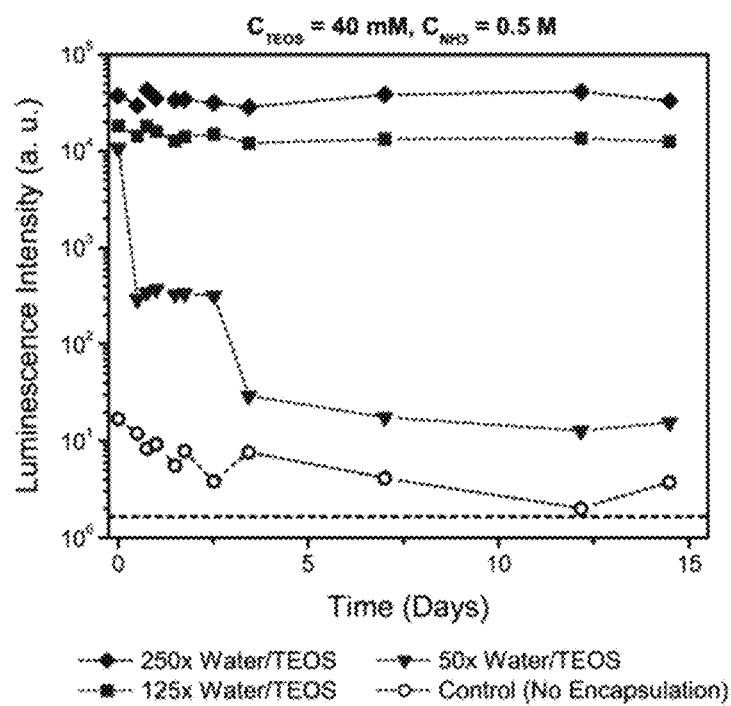

Strontium aluminate is not stable in water, and readily hydrolyzes, which greatly decreases or completely destroys the luminescent properties of the material. Encapsulation with silica using a modified Stöber process was carried out to make the particles water-stable, while preserving their luminescence properties. Silica encapsulation of strontium aluminate phosphors is non-trivial as water is an essential reactant in the Stöber process, but also hydrolytically degrades the phosphors. Extensive hydrolysis of the silicon precursor tetraethoxysilane (TEOS) is needed to form an effective water-resistant silica barrier encapsulating the particles, as illustrated in FIGS. 9-11. Running the Stöber process for too long or with a low concentration of phosphors can result in undesirable pure silica particles in the mixture without phosphorescent cores, and could potentially encapsulate particles in excessive silica such that it adversely affects luminescence. FIG. 12 show the results of Stöber process optimization experiments, which demonstrate that a high water concentration (≈18% v/v) is needed to make the particles water-stable, which is in agreement with model predictions of silica shell thickness as a function of initial water concentration (FIG. 11). The data show that encapsulated phosphors can be suspended in water for at least 2 weeks without significant loss of luminescence. In Applicants' experience, the encapsulated phosphors do not apparently experience hydrolytic degradation, even after a month in water.

Figure 2:
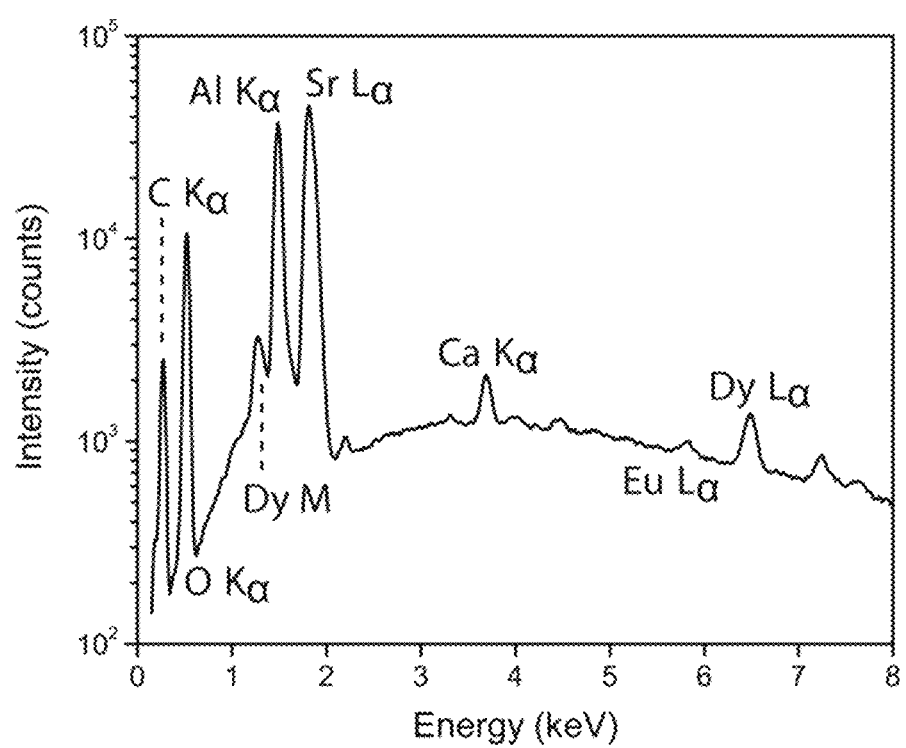
FIG. 2 shows energy dispersive x-ray spectroscopy (EDS) data of as-purchased strontium aluminate phosphorescent powder, with peaks for C, O, Al, Dy, Sr, Ca, Eu, and Dy denoted.
Figure 13:
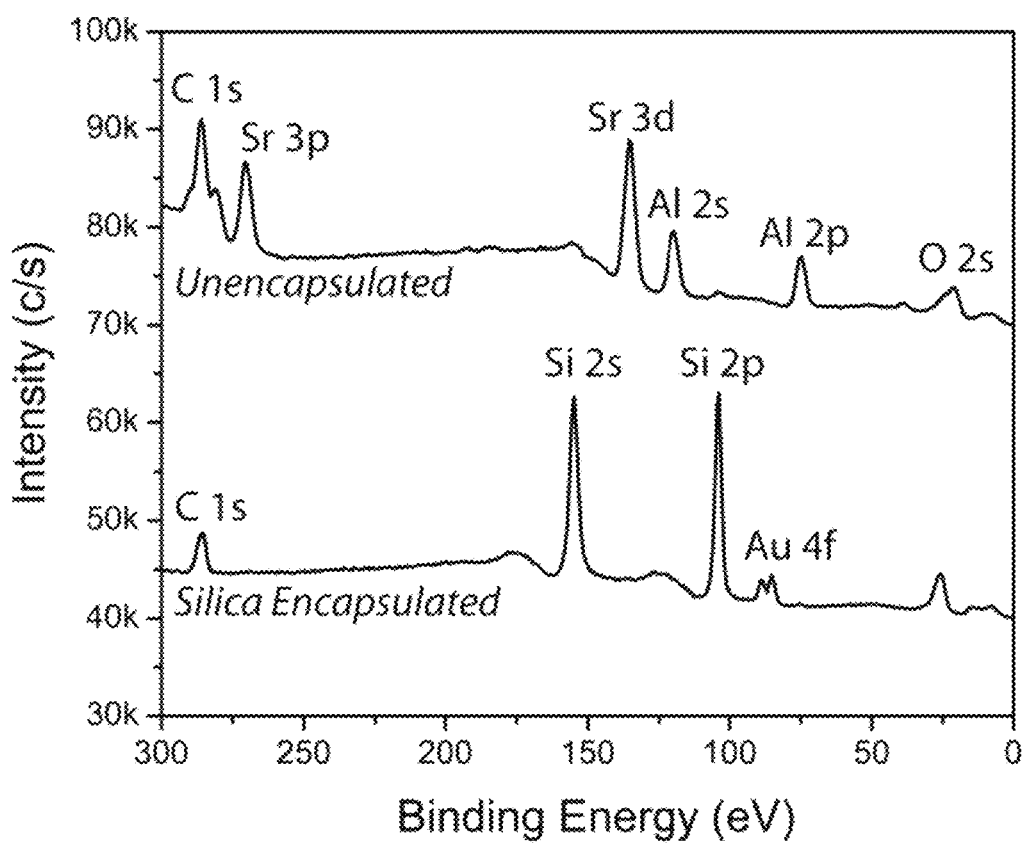
FIG. 13 shows XPS spectra of bare unencapsulated strontium aluminate phosphorescent particles, and silica encapsulated strontium aluminate phosphors.
Figure 14:
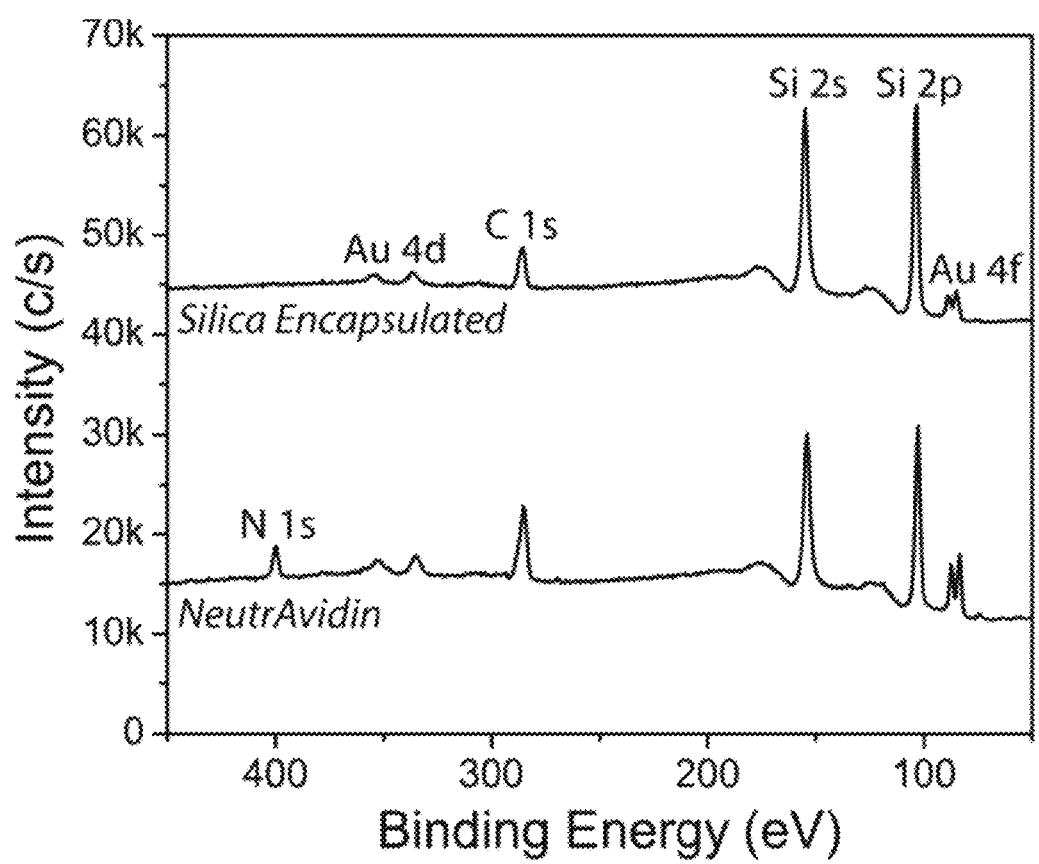
FIG. 14 shows XPS spectra of silica encapsulated strontium aluminate phosphors, and silica encapsulated phosphors functionalized with NeutrAvidin.

Energy dispersive x-ray spectroscopy (EDS) was used for basic elemental analysis of the as-purchased phosphors, to confirm the presence of Si peaks after the Stöber process, and look for zirconium contamination from milling. FIG. 2 shows the EDS spectrum of bare strontium aluminate phosphors. Applicants did not observe any zirconium EDS peaks from milled phosphors, indicating negligible contamination. The Si Kα and Sr Lα peaks overlap at around 1.7-1.8 keV, making it hard to verify successful silica encapsulation by EDS, therefore x-ray photoelectron spectroscopy (XPS) was used for surface characterization and analysis. XPS data in FIG. 13 confirms the presence of Si, and the suppression of Sr and Al peaks indicates that the particles are effectively encapsulated in silica, with the silica shell thickness of at least 20 nm.

Figure 15:
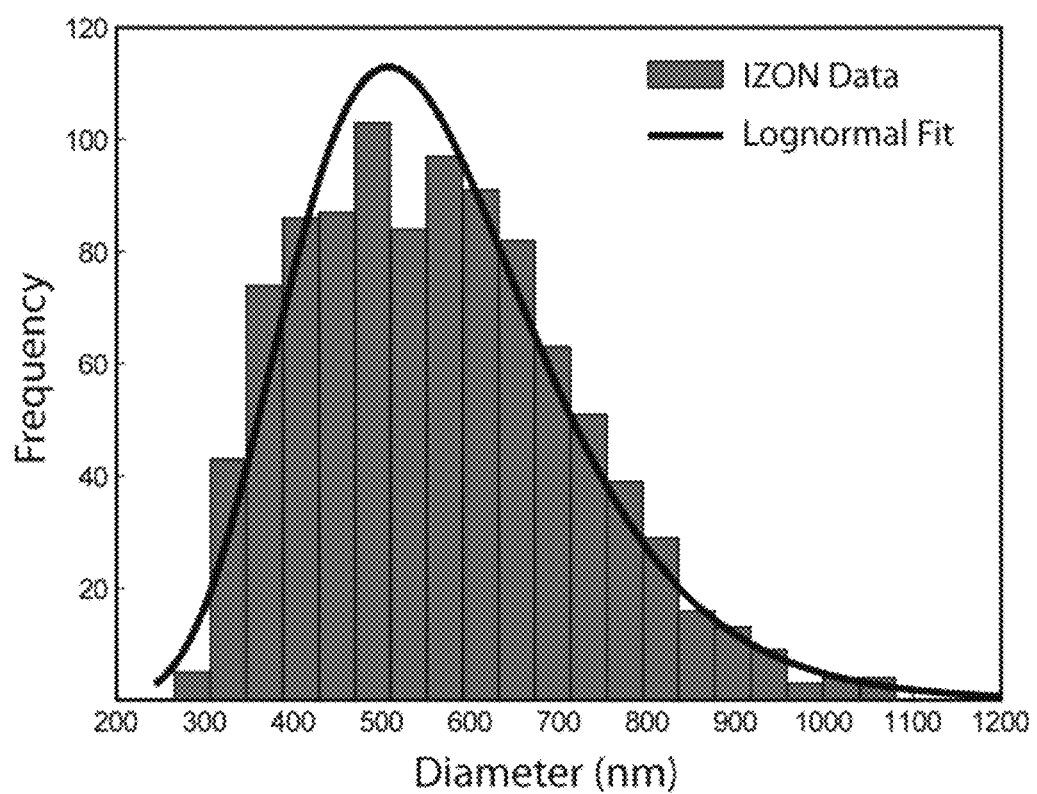
FIG. 15 shows a particle size distribution of silica encapsulated strontium aluminate phosphors functionalized with PEG. The data were acquired with a size tunable nanopore instrument (IZON).

Several particle sizing techniques were used to analyze the phosphors including dynamic light scattering (DLS), suspended microchannel resonator mass measurements with an Affinity Biosensors Archimedes Particle Metrology System (FIG. 8), and single particle volume-based measurements with an IZON size-tunable nanopore (FIG. 15). The data demonstrate that Applicants are able to isolate submicron phosphors by a combination of wet milling and fractionation. Removing the larger particles roughly a micron in diameter is essential for diagnostic formats like the lateral flow assay and the flow through assay to minimize blocking of pores in the membranes.

Figure 16:
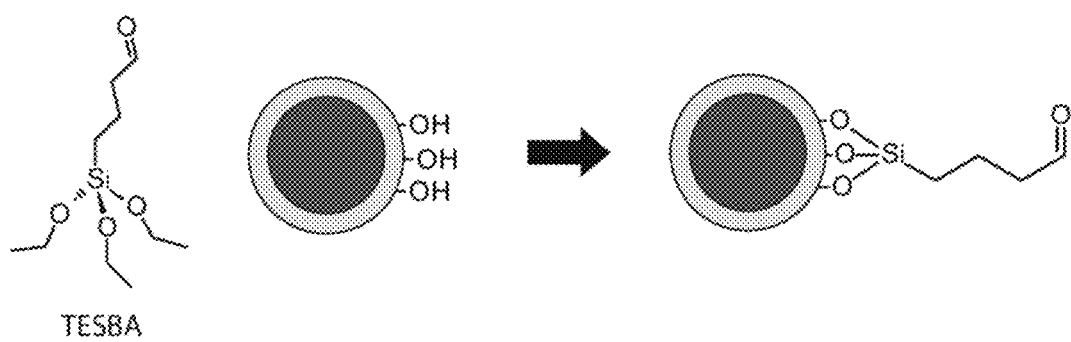
FIG. 16 is a schematic showing the reaction of a silica encapsulated phosphorescent particle reacting with triethoxysilylbutyraldehyde (TESBA) to introduce surface aldehydes for covalent attachment of moieties to the surface.
Figure 17:
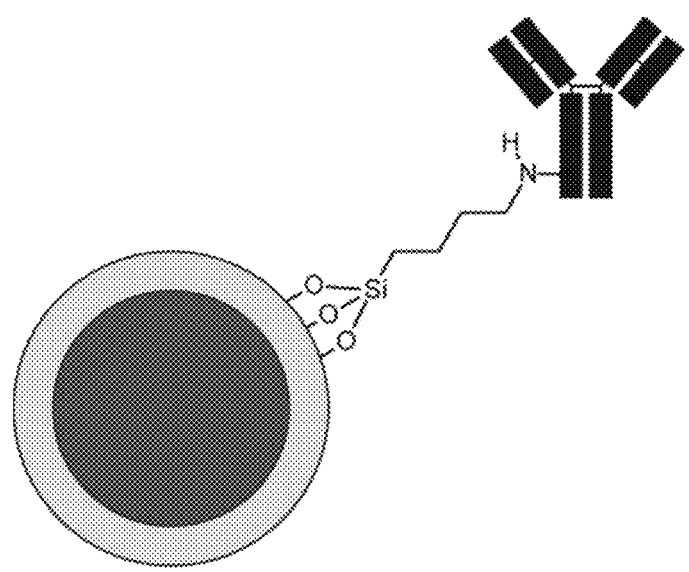
FIG. 17 shows a schematic of a silica encapsulated phosphorescent reporter with an antibody coupled to the surface by reductive amination between a surface aldehyde introduced by TESBA and an amine from the protein.
Figure 18A:
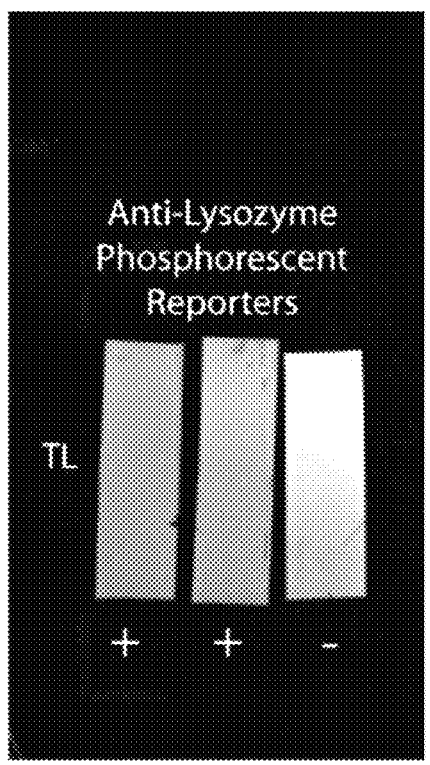
FIGS. 18A-18B show a phosphor LFA experiment with anti-lysozyme HyHEL-5 phosphorescent reporters functionalized as shown in FIG. 17. The two LFA strips marked "+" had a test line prepared by spotting hen egg lysozyme directly onto the nitrocellulose membrane. The strip marked "−" was a negative control with no lysozyme. The LFA strips under brightfield illumination (FIG. 18A). The LFA strips after photoexcitation and luminescence imaging mode (FIG. 18B).
Figure 18B:
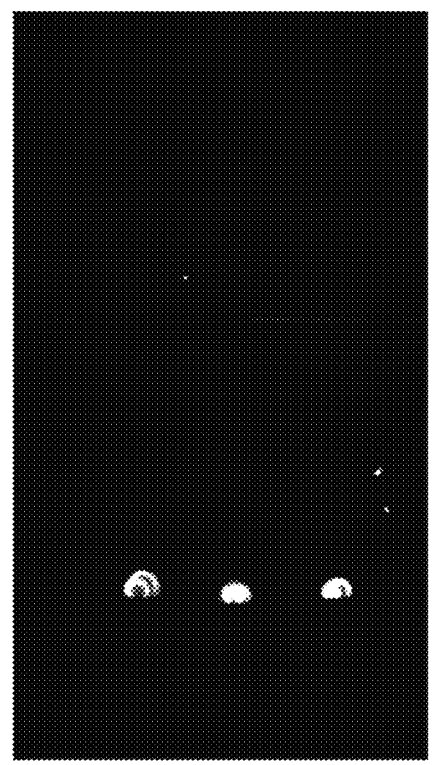
Figure 19:
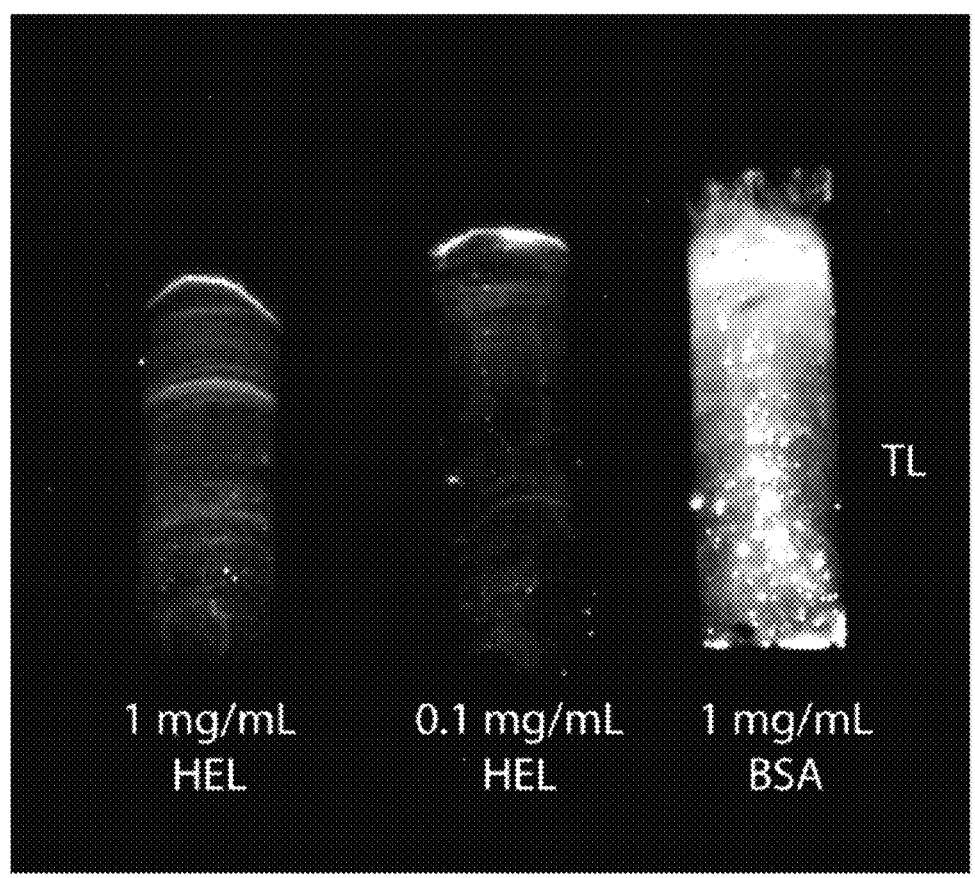
FIG. 19 shows a phosphor LFA experiment with anti-lysozyme D1.3 test lines. Hen egg lysozyme (HEL) and bovine serum albumin (BSA) were used as analytes at the specified concentrations. Anti-lysozyme HyHEL-5 phosphorescent particles functionalized as shown in FIG. 17 were used as reporters.
Figure 20:
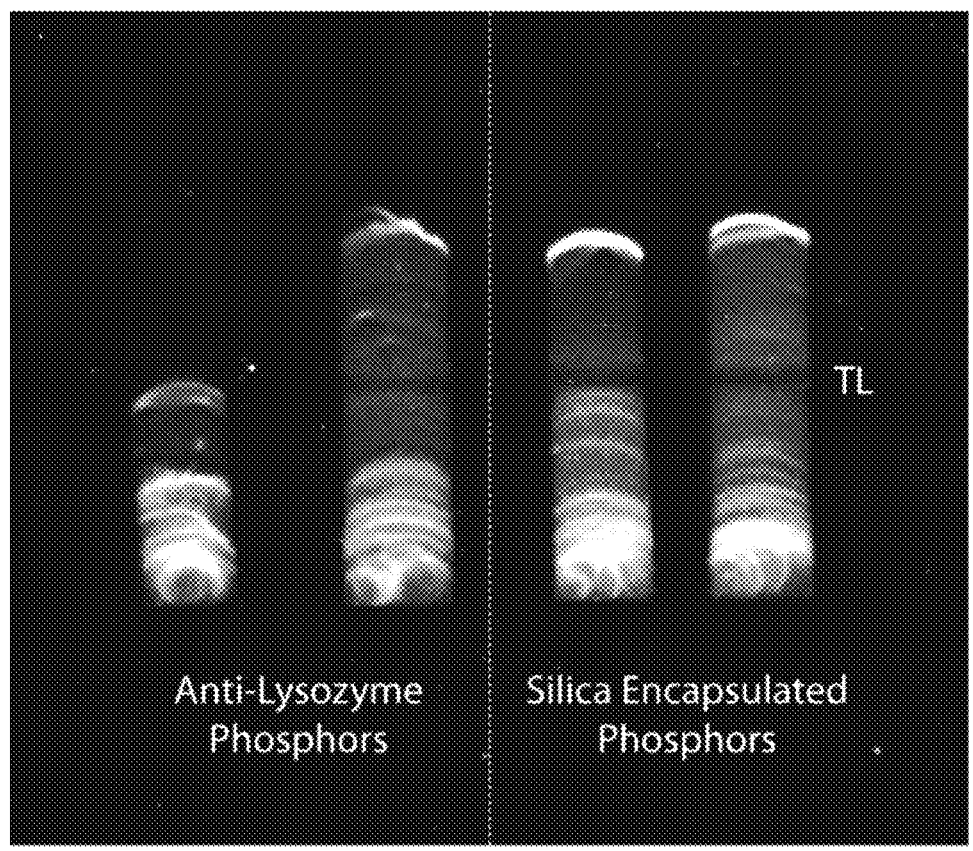
FIG. 20 shows a phosphor LFA experiment with hen egg lysozyme directly spotted on the membrane as the test line in all strips. (Left) Anti-lysozyme HyHEL-5 phosphors used as reporters (Right) Silica encapsulated phosphors were used as a control to assess the effect of surface moieties on transport of the phosphorescent reporters through the membranes.
Figure 21:
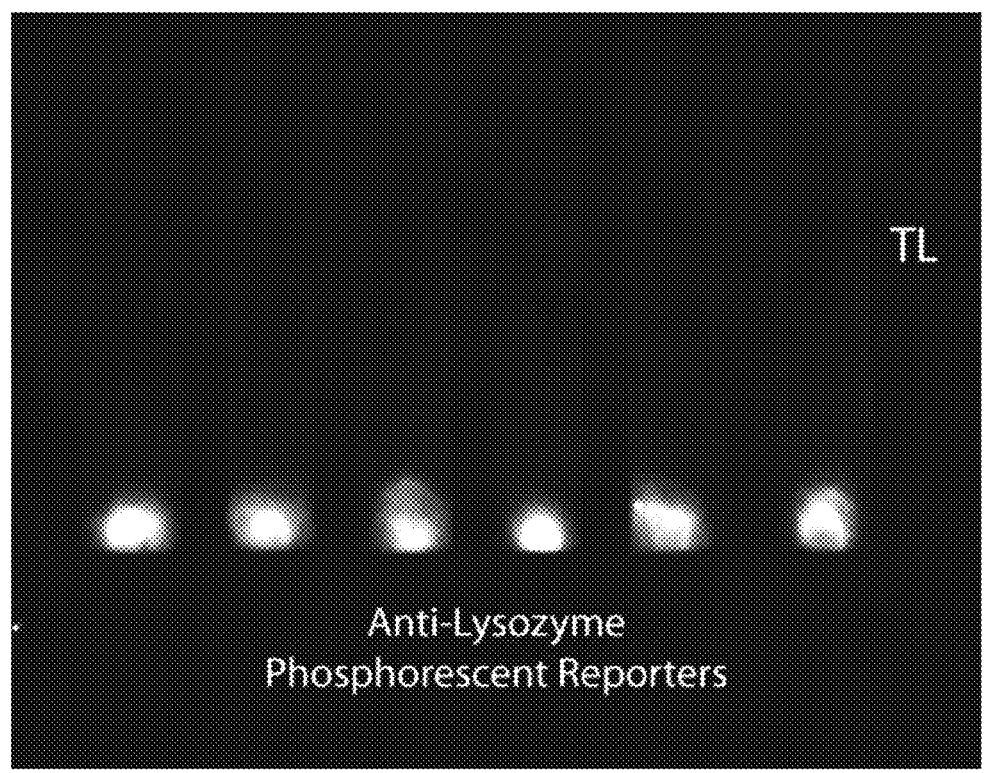
FIG. 21 shows a phosphor LFA experiment with a lysozyme test line spotted on a Fusion 5 glass fiber membrane, with six replicates. Anti-lysozyme HyHEL-5 phosphors were used as reporters.

The initial strategy for coupling antibodies to the surface of the particles involved the introduction of surface aldehydes by triethoxysilylbutyraldehyde (TESBA) as shown in FIG. 16, followed by direct reductive amination of surface aldehydes with proteins (FIG. 17).

In various embodiments, other trialkoxysilanes like (3-aminopropyl)triethoxysilane (APTES) and various chlorosilanes can be used as substitutes for TESBA with some slight modifications of the conjugate chemistry protocols. In various embodiments, crosslinkers like 1,2-bis(triethoxysilyl) ethane (BTEOSE) and bis[3-(trimethoxysilyl) propyl] amine (BTMOSPA) can also be used in combination with an alkoxysilane to improve the hydrolytic stability of the surface reactive groups when the particles are suspended in water or buffer.

The lateral flow assay (LFA) is one of the most common in vitro diagnostics formats for point-of-care applications. Many LFAs are conducted using a device like the one presented in FIG. 41, with a sample pad, a conjugate pad, a membrane, and an absorbent pad connected to make an immunochromatographic strip that is functionalized with some type of molecular recognition moieties for detecting an analyte. There are numerous variations of the device in FIG. 41, such as combining all of the components (e.g. the sample pad, conjugate pad, etc.) into a single membrane or pad for analyte detection. In the context of the present disclosure and application a LFA generally refers to any test in which a sample flows or wicks within or laterally through a porous material to enable the detection of at least one analyte or enable confirmation of the absence of at least one analyte. A LFA can be solely qualitative and provide a yes/no result, and can also be a quantitative test to determine total amount or concentration of an analyte. A LFA can be designed such that the presence of a signal and that signal's intensity, such as luminescence from a phosphorescent reporter, is proportional to the concentration of an analyte. A LFA can also be designed in a competitive format such that the presence of an analyte decreases the intensity of a specific signal, a technique that is commonly employed for detecting small molecules such as drugs of abuse.

Figure 22A:
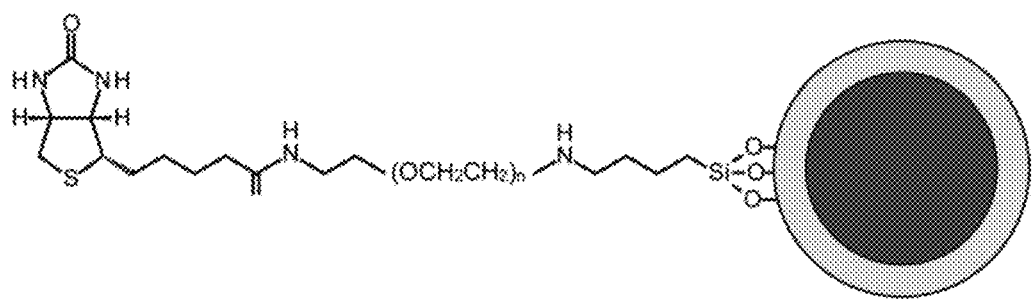
FIGS. 22A-22C show schematic depicting a phosphorescent reporter functionalized with biotin-PEG-amine by reductive amination with surface aldehydes on the phosphor from TESBA (FIG. 22A). Brightfield image of LFA strips functionalized with NeutrAvidin test lines and run with biotin-PEG phosphors as reporters (FIG. 22B). Darkfield image of the LFA strips showing luminescence from the test line from bound biotin-PEG phosphorescent reporters (FIG. 22C). The $2^{nd}$ and $4^{th}$ strips from the left were not spotted with phosphors to show that the light emanating from the test line in the $1^{st}$ and $3^{rd}$ strips is from phosphors and not from the proteins adsorbed at the test line.
Figure 22B:
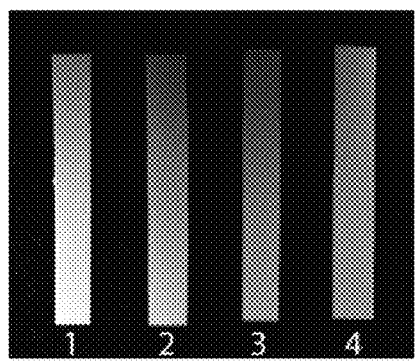
Figure 22C:
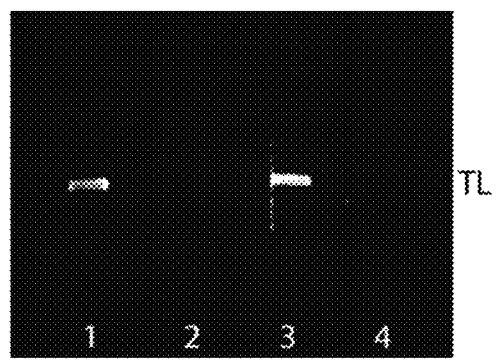

FIGS. 18-21 show results of attempted LFA experiments with phosphor reporters where antibodies were directly coupled to the phosphors through aldehydes as shown in FIG. 17. Aggregation was usually observed and it was difficult to get particles to flow through nitrocellulose and glass fiber membranes. A preliminary experiment to see if conjugating PEG to the particles could improve the transport of phosphors through lateral flow membranes was carried out by coupling the surface aldehydes of phosphorescent reporters to amine-PEG-biotin (FIG. 22A-22B). Test lines were spotted with NeutrAvidin on nitrocellulose membranes. Little background signal in the LFA strips were observed from phosphors in the membrane and a strong signal was observed at the test line. The Applicants have also observed that phosphorescent reporters are more easily resuspended in aqueous solutions after centrifugal settling when functionalized with PEG. Other hydrophilic or water soluble polymers could be used in combination with or in place of PEG for functionalizing phosphorescent reporters. In all subsequent experiments, phosphorescent reporters were functionalized with PEG before bioconjugation.

Figure 23:
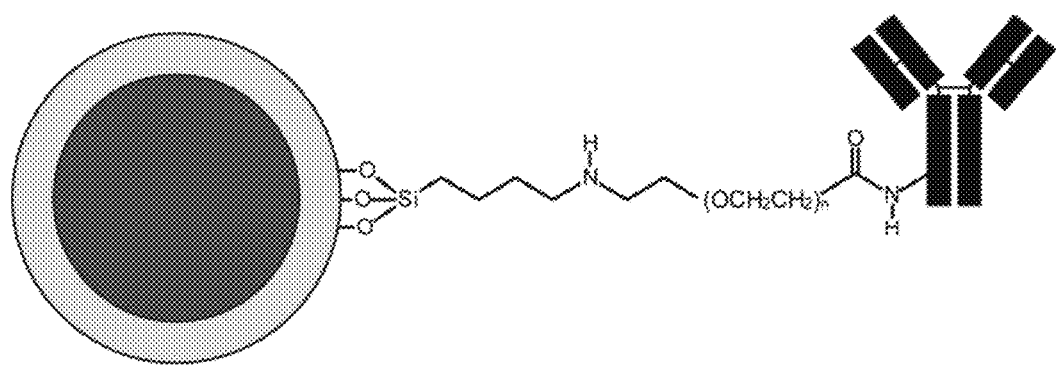
FIG. 23 depicts a phosphorescent reporter with an antibody covalently attached by an amide bond formed by carbodiimide chemistry between a grafted PEG moiety with a terminal carboxylic acid group and a primary amine on the antibody. The PEG was grafted to the phosphorescent reporter by reductive amination with aldehydes from TESBA.
Figure 24:
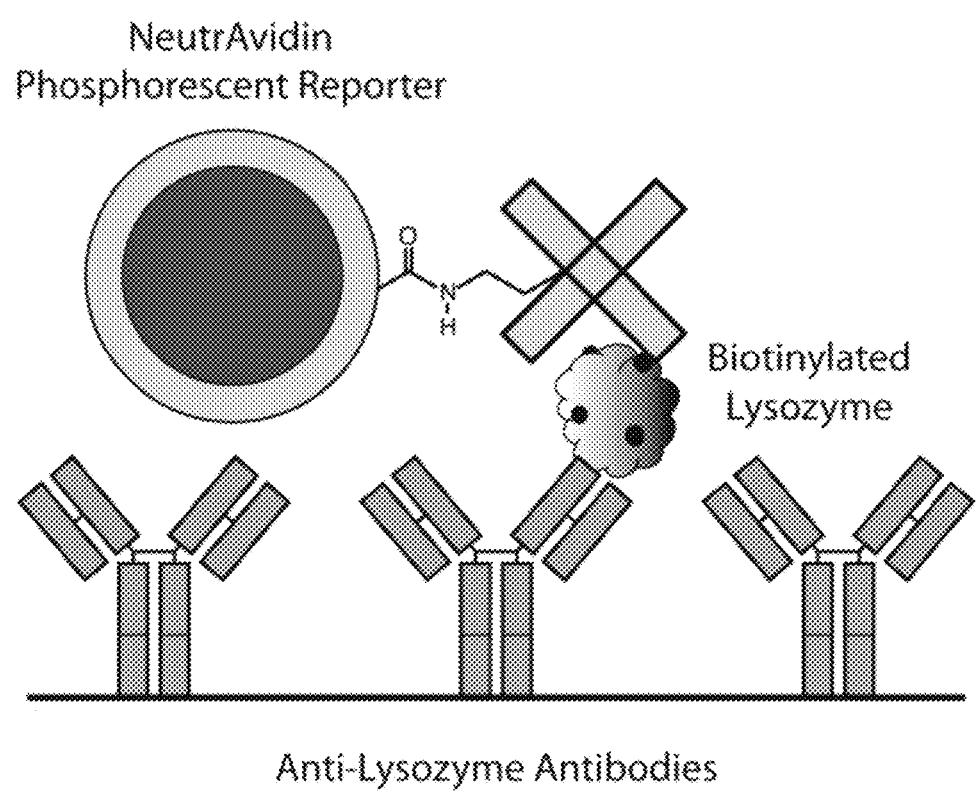
FIG. 24 is a schematic depicting the detection of biotinylated lysozyme by a sandwich between an anti-lysozyme antibody and a NeutrAvidin phosphorescent reporter.
Figure 25:
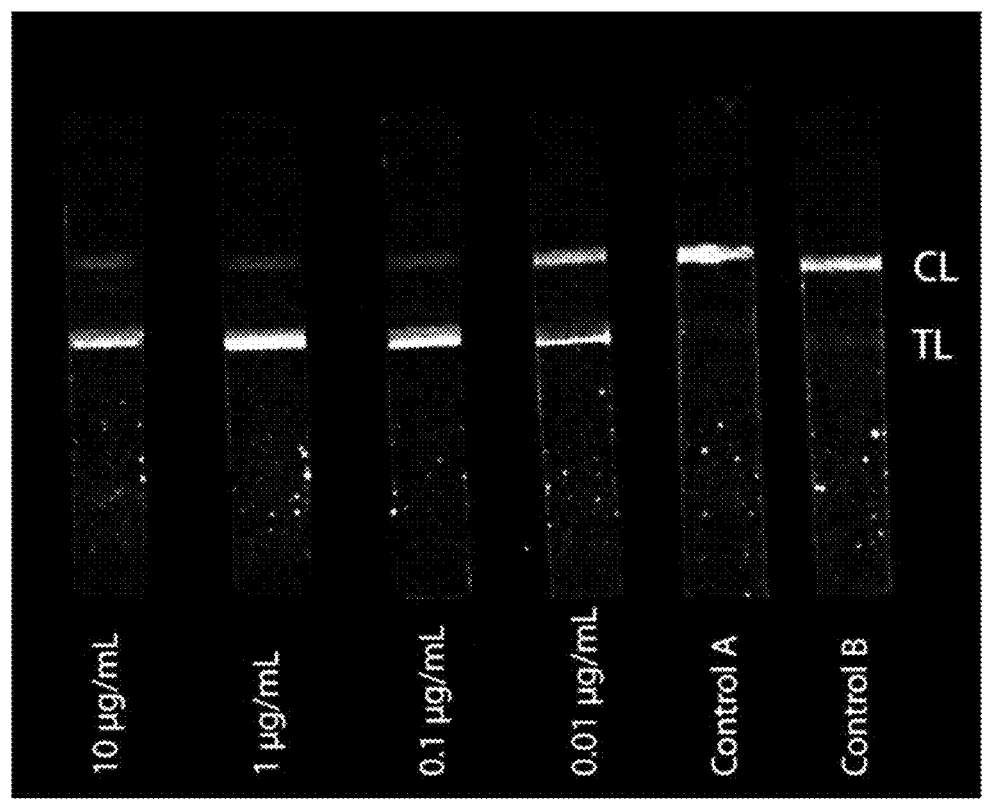
FIG. 25 shows an LFA experiment with biotinylated lysozyme analyte, HyHEL-5 test line, NeutrAvidin-PEG phosphorescent reporters, and biotinylated BSA control line.
Figure 26:
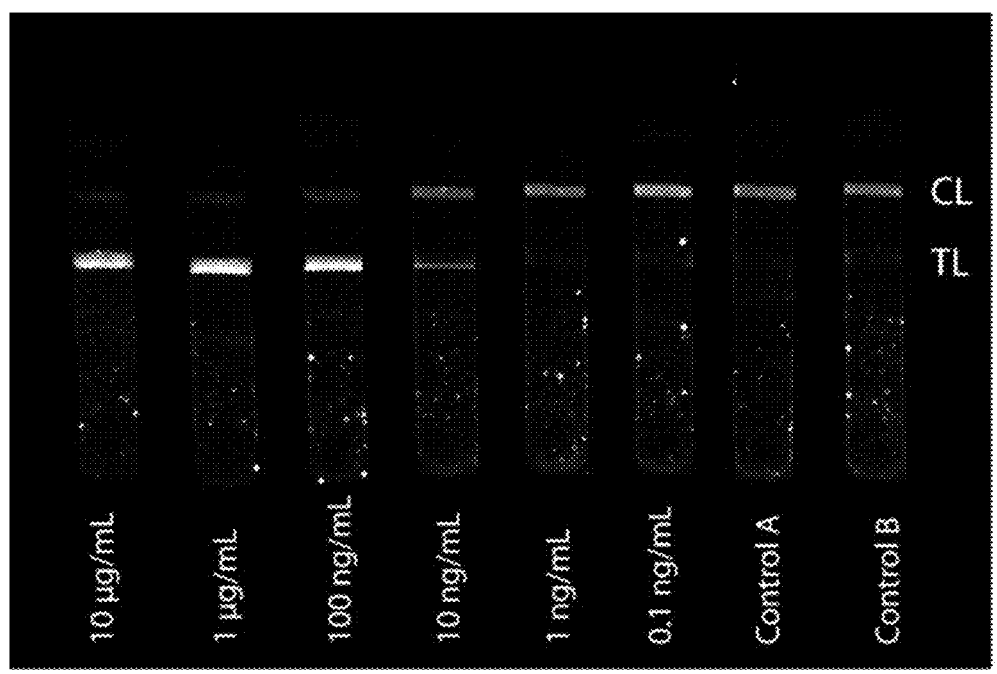
FIG. 26 shows a repetition of the LFA experiment in FIG. 25 with additional lower analyte concentrations tested.
Figure 27:
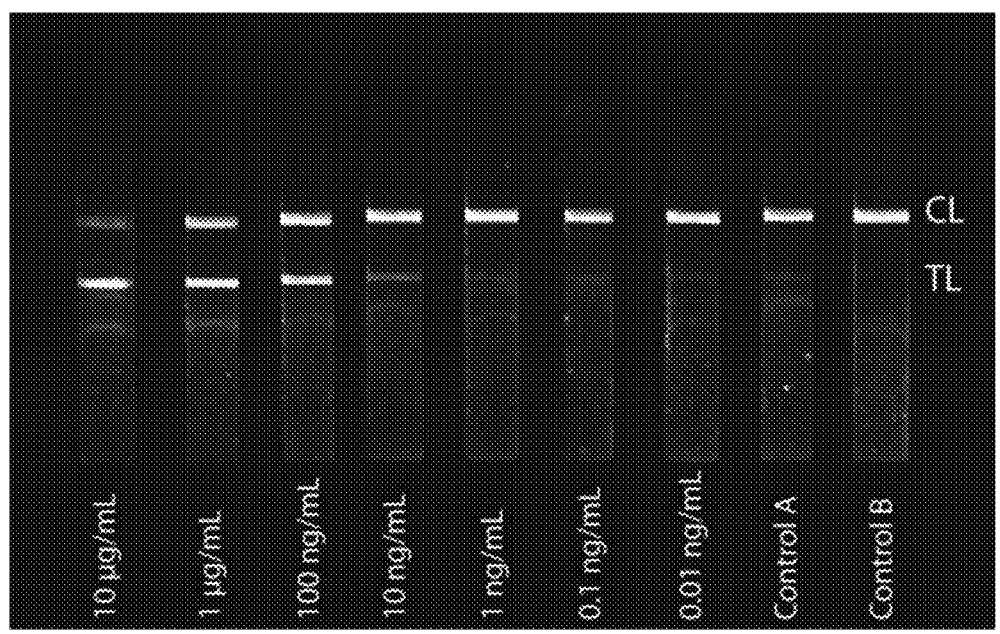
FIG. 27 shows an LFA experiment with biotinylated lysozyme as the analyte and NeutrAvidin phosphorescent reporters as in FIG. 25 and FIG. 26, but with a different monoclonal anti-lysozyme antibody at the test line, D1.3.
Figure 28:
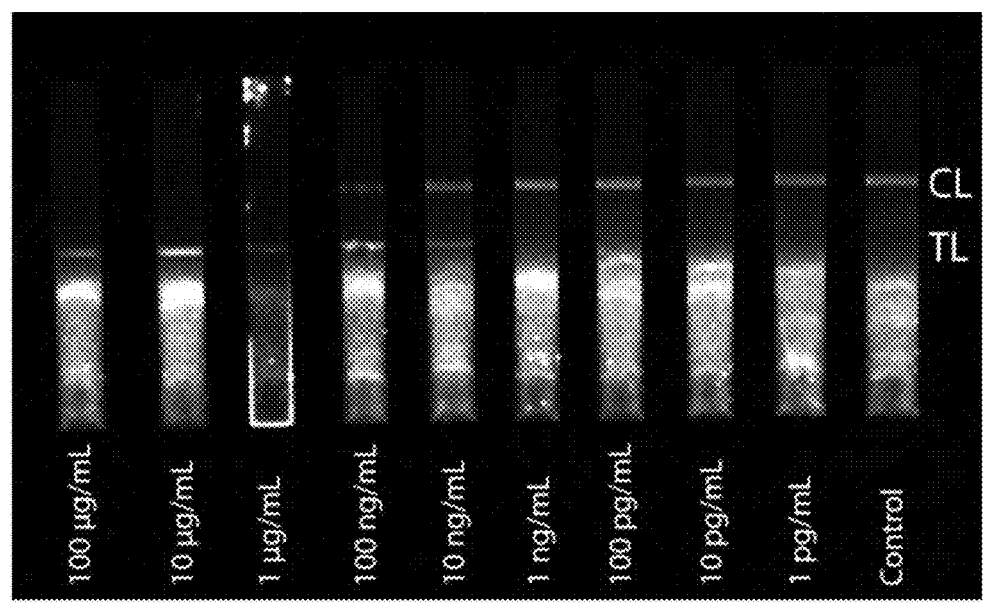
FIG. 28 shows an LFA experiment with NeutrAvidin phosphors, biotinylated lysozyme analyte, D1.3 test lines, and biotinylated BSA control lines as in FIG. 27, but with membranes that were passivized with non-fat dry milk.
Figure 31:
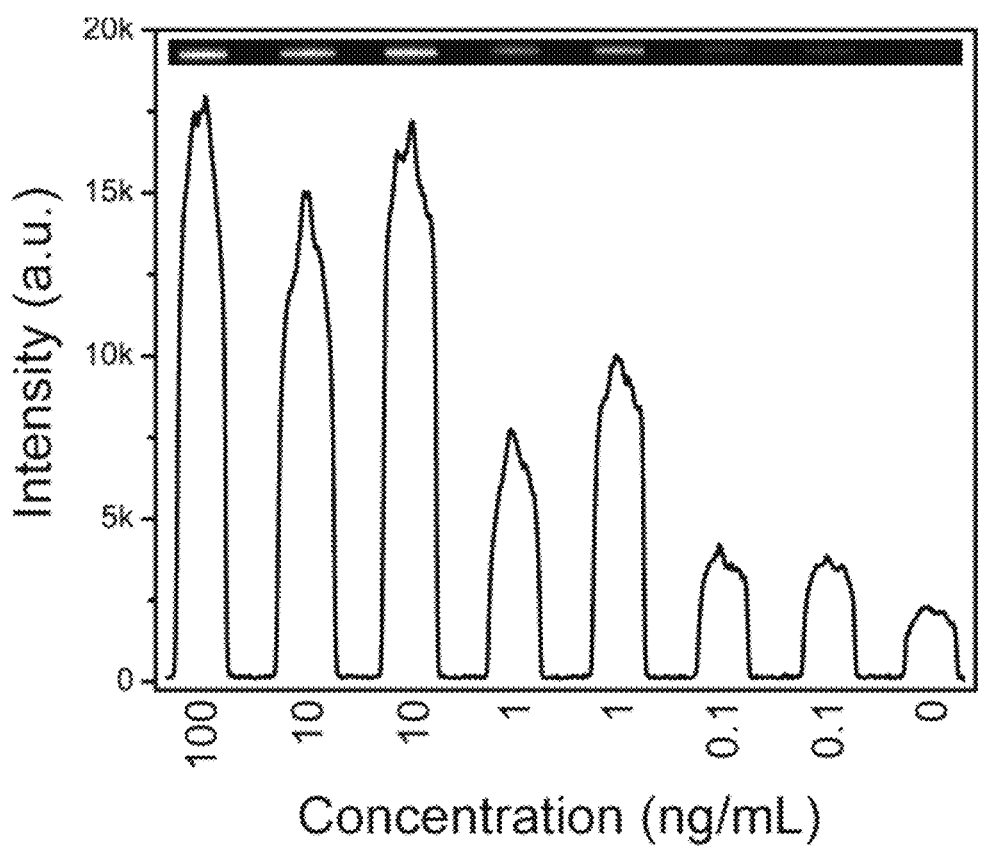
FIG. 31 shows test line intensity profiles across the width of the LFA strips from the experiment shown in FIG. 30. The figure illustrates the potential for quantitation of analyte concentration and helps demonstrate the low limit of detection.
Figure 32A:
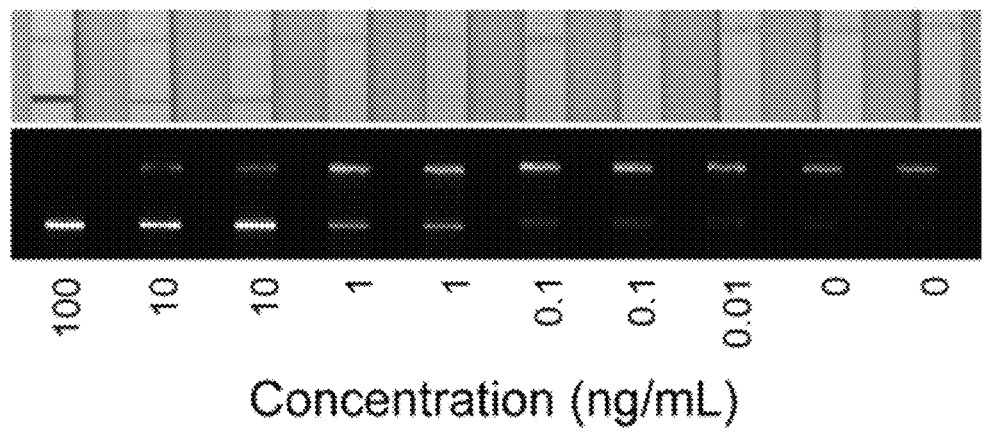
FIGS. 32A-32B show a comparison of gold nanoparticles and phosphorescent reporters in LFAs for detecting biotinylated lysozyme.
Figure 32B:
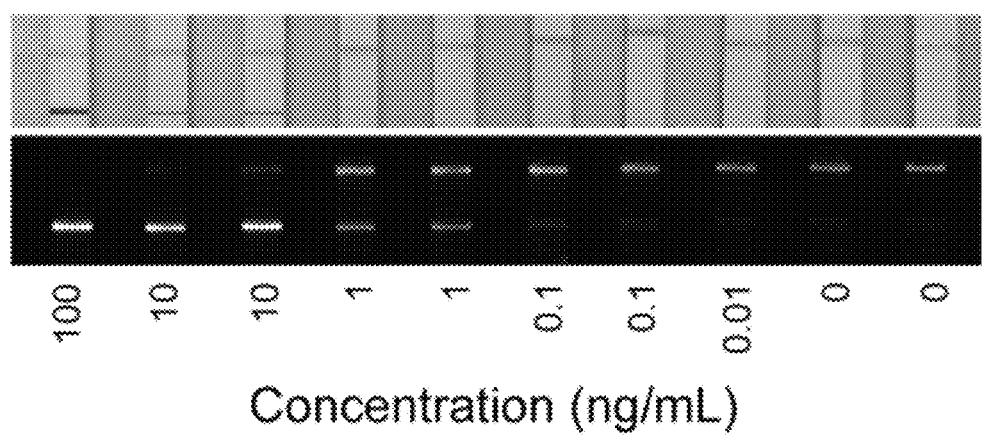
Figure 33:
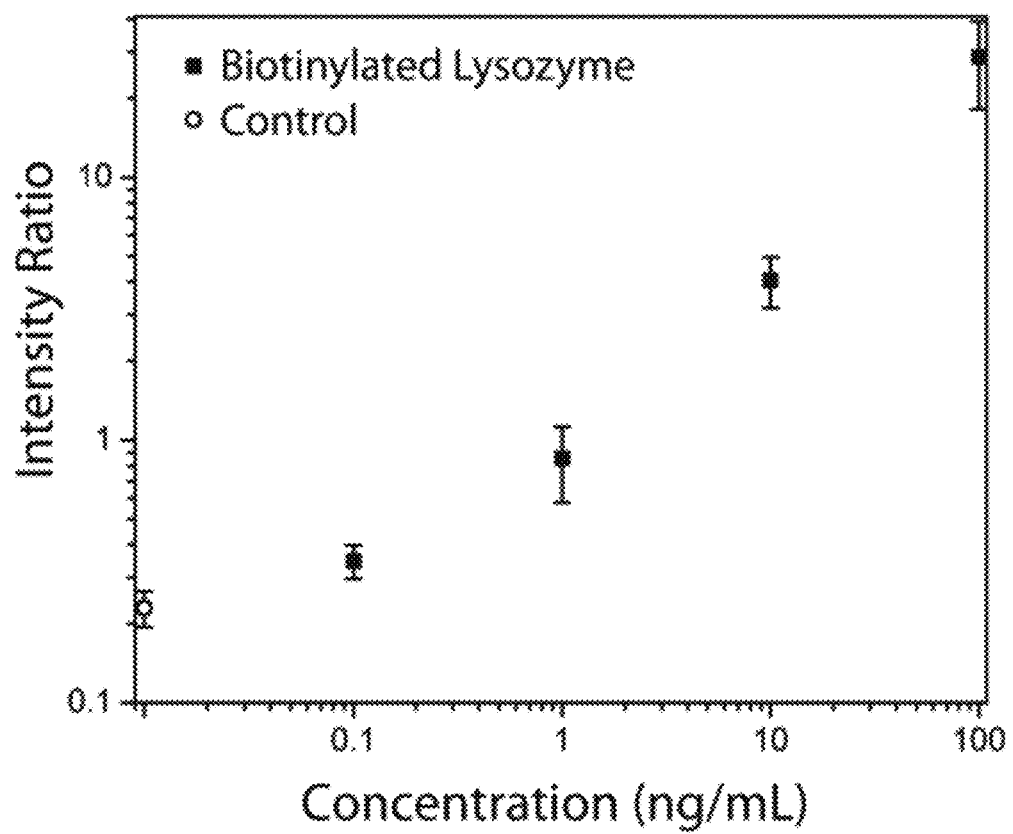
FIG. 33 shows a quantitative analysis of LFA experiments with biotinylated lysozyme analyte and phosphorescent reporters. The plot depicts the intensity ratio of the test line over the control line as a function of analyte concentration.

Heterobifunctional amine-PEG-carboxyl was coupled to surface aldehydes of phosphorescent reporters by reductive amination, and the terminal carboxyl groups were used for coupling to primary amines by carbodiimide chemistry using 1-ethyl-3-(3-dimethylaminopropyl)carbodiimide (EDC) and N-hydroxysuccinimide (NHS) (FIG. 23). FIGS. 25-28 and 30-33 show the results of various LFA experiments for detecting biotinylated lysozyme with phosphorescent reporters functionalized with amine-PEG-carboxyl and NeutrAvidin. A schematic illustrating the detection of biotinylated lysozyme with a NeutrAvidin phosphorescent reporter is shown in FIG. 24. The phosphorescent reporters resulted in highly sensitive detection of the analyte, with better performance than the commonly used gold nanoparticle in LFAs (FIG. 32), and potentially allow straightforward quantitation from the luminescence signal. FIG. 31 shows intensity profiles from the test line across the width of the LFA strips from the experiment in FIG. 30. The intensity of the signal at the test line is proportional to the analyte concentration, and could be related to a calibration curve to allow determination of the concentration or amount of an analyte from an unknown sample. FIG. 33 shows an example of one type of calibration curve that could be generated to allow analyte quantitation. In this case, the ratio of the test line intensity to the control line intensity is used as a quantitative metric for the signal. Other quantitation means could be employed, such as absolute photon counting.

In some embodiments an assay, such as a flow-through assay or LFA, is designed to test for multiple analytes using phosphorescent reporters. In some embodiments multiple analytes are tested for by using spectral-based multiplexing in which different phosphors with distinct emission spectra are functionalized to enable the detection of different analytes. In some embodiments, multiplexing is carried out by using different recognition entities that bind to different analytes, and functionalizing different locations of a surface used in an assay with distinct recognition entities.

Figure 29:
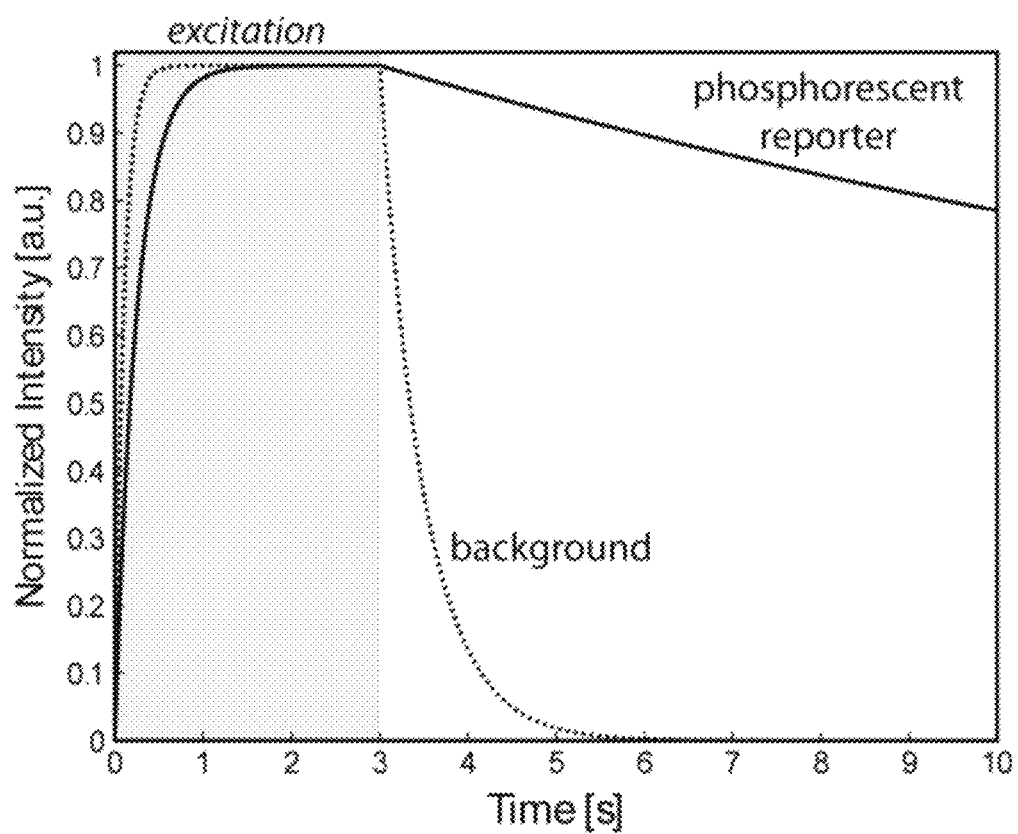
FIG. 29 illustrates the principle of time-gated or time-resolved luminescence assays with phosphorescent reporters. At some initial time the light intensity from the phosphorescent particles and the background is close to zero. Application of an excitation light source results in an increase in photoluminescence from the phosphorescent reporters, and background luminescence with contains both auto fluorescence and scattered excitation light. When the excitation light is switched off, the background decays rapidly, and the phosphorescent reporter signal decays slowly, leading to a higher signal-to-background ratio, and a lower limit of detection.
Figure 30:
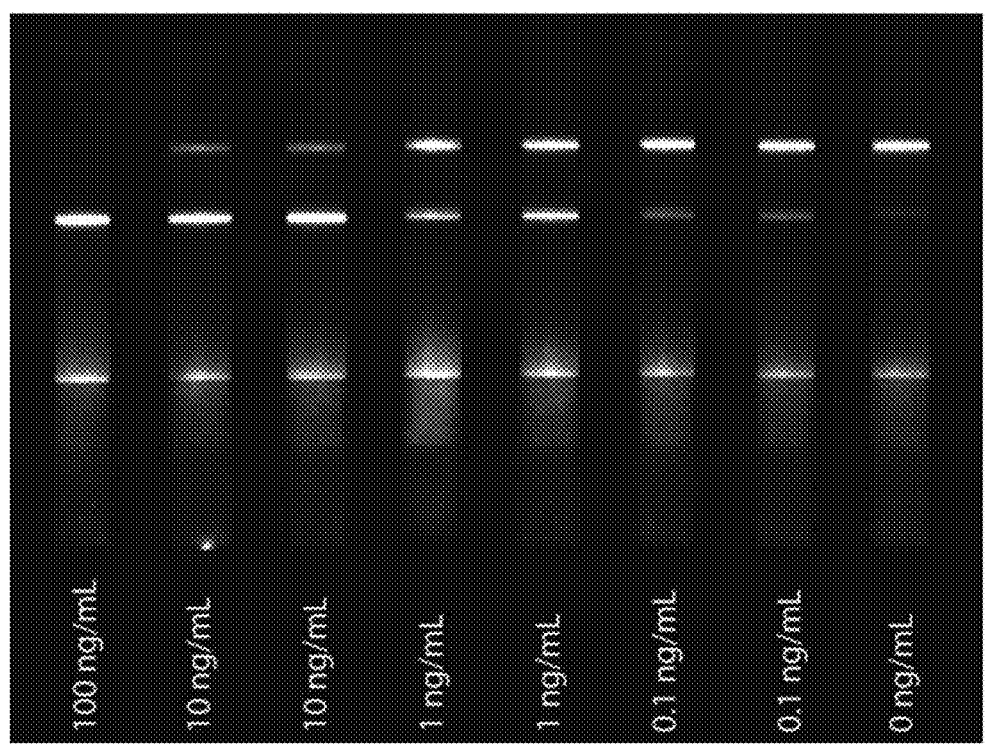
FIG. 30 shows an LFA experiment with NeutrAvidin phosphorescent reporters as in FIG. 25 and FIG. 26 after further optimization of the protocols. The detection limit is close to 100 pg/mL.

Detection of luminescence from the phosphorescent reporters in any arbitrary assay format is shown in FIG. 29. At some initial time, an excitation light source is switched on causing an increase in photoluminescence from the phosphorescent reporters, and causing an increase in the background signal from autofluorescence from the local environment including assay device materials and the sample matrix, in addition to background light from scattering from the excitation source. In this illustration, the relative intensity from the phosphorescent reporters and the background are equal. When the excitation light is switched off, the background signal rapidly decays while the phosphorescent reporter continuously emits luminescence, resulting in an increased signal-to-background ratio.

Figure 34:
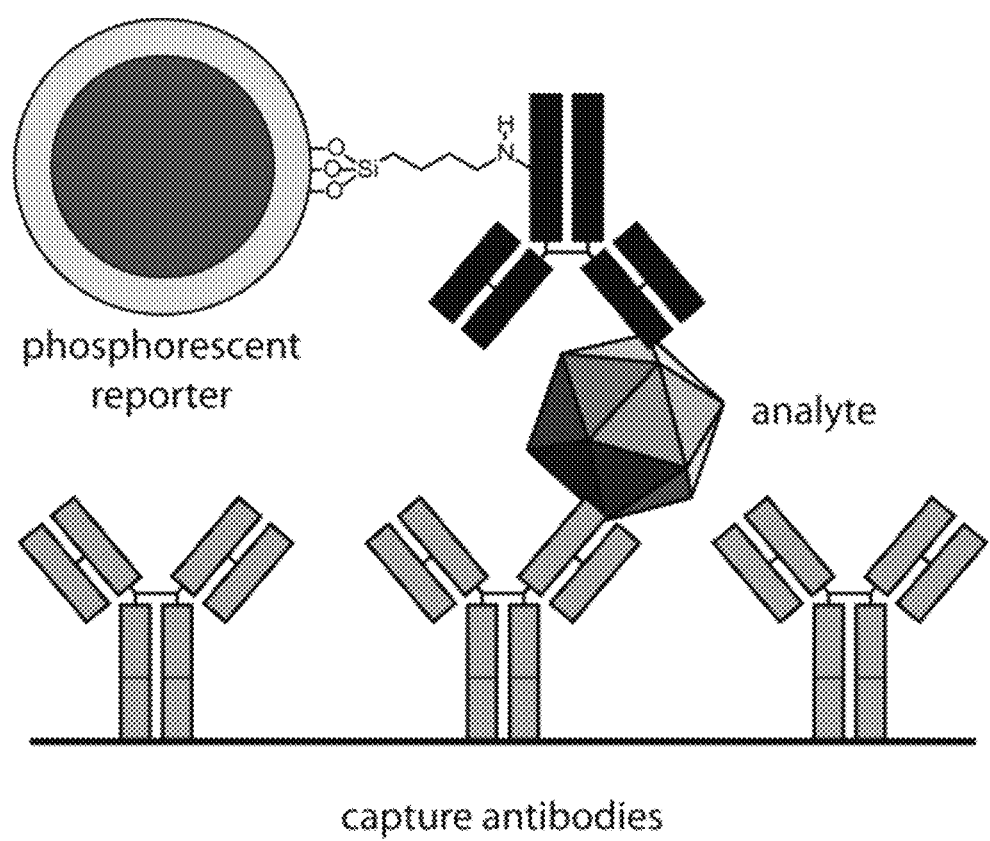
FIG. 34 is a general schematic showing the detection of an arbitrary analyte in a sandwich immunoassay with capture antibodies immobilized on a surface and a phosphorescent reporter.

Applicants have observed that the phosphors can serve as labels in LFAs for a variety of analytes after optimization including the detection of whole viruses, bacteria, and a variety of proteins. The phosphorescent reporters are useful in assay formats other than LFA, and generally can be used in any binding assay as shown by the schematic in FIG. 34. The schematic shows antibodies on the surface for capturing analyte and antibodies on the particles, but both the antibodies on the particles and the antibodies immobilized on the surface can be substituted with any other entity capable of molecular recognition such as a nucleic acid, lectin, aptamer, or other molecule.

One assay format that Applicants have run preliminary experiments with is the flow through assay (FTA). In a FTA, molecular recognition entities are adsorbed or immobilized on a membrane, and then a sample and phosphorescent reporters are flowed directly through the membrane rather than laterally. The sample and phosphorescent reporters can be added sequentially to the flow-through membrane, or pre-mixed and then added to the membrane. Imaging or quantitative measurements are then carried out to examine luminescence emanating from the membrane, which is typically, but not necessarily, proportional to the analyte concentration.

Figure 35A:
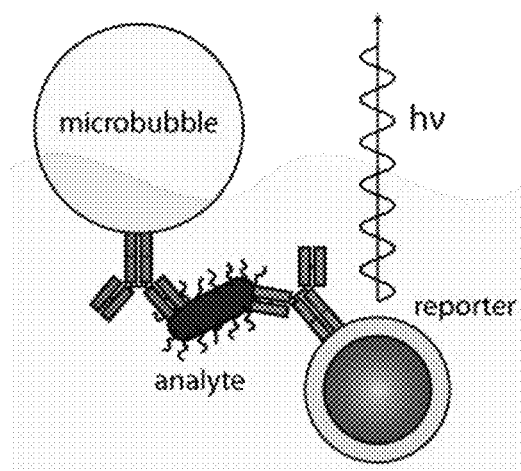
FIGS. 35A-35B shows a flotation assay with phosphorescent reporters for detecting an analyte. A buoyant object like a glass microbubble is functionalized with antibodies and binds to the analyte which is relocated to the top of the liquid due to flotation of the buoyant object (FIG. 35A). Luminescence is detected from the top of the liquid, and background luminescence from unbound phosphorescent reporters is blocked by absorption from dye within the liquid. SEM image showing phosphorescent reporters bound to glass microbubble in preliminary flotation assay experiment (FIG. 35B).
Figure 35B:
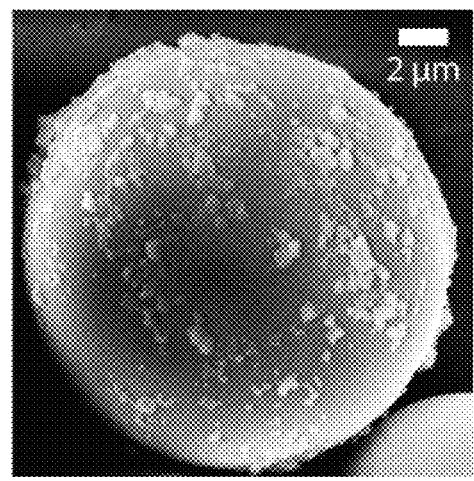

Applicants have also experimented with phosphors in flotation assays in which a buoyant object (a silica microbubble or thin polyethylene sheet) forms a sandwich complex with an analyte and a phosphor, and floats to the top of the sample solution, dragging the phosphor along. Adding dye to the mixture reduces the background signal from phosphorescent reporters suspended in solution and ensures that most of the luminescence signal comes from phosphors bound to analyte and the buoyant object at the top of the sample. A schematic of the flotation assay is shown in FIG. 35 along with a SEM image of phosphors bound to a microbubble from a past flotation assay experiment. In this experiment, phosphorescent reporters functionalized with anti-E. coli antibodies were added to a microcentrifuge tube containing a sample with E. coli and microbubbles functionalized with anti-E. coli antibodies. The contents of the tube were mixed, and then allowed to settle before measuring luminescence from the top arising from bubbles with bound phosphorescent reporters.

The data from LFA experiments shown up to FIG. 33 were acquired using a standard gel chemiluminescence and fluorescence imaging system. Readout of assays run with phosphorescent reporters can also be carried out with low cost devices in consumer electronics such as a cell phone camera. FIGS. 39-40 show images of LFA strips run with phosphorescent reporters, excited with a 2.5 mW UV/blue LED and imaged with an iPhone 5s. These images were acquired in a time-gated manner as depicted in FIG. 29, by illuminating the strips briefly for excitation, then turning off the LED and capturing an image. One could also use the native light on a phone or mobile device as the excitation source.

A typical interpretation of LFA results (i.e. whether the sample is positive or negative), can be carried out by looking for the presence or absence of a test line on the strip. For instance, the test line is clearly visible in FIG. 40A, indicating the presence of an analyte. It is also possible to interpret the results by looking at line scans that show the relative intensity down the length of a lateral flow strip and looking for a peak of sufficient magnitude or area at the test line to indicate the presence of an analyte (FIGS. 36-38, FIG. 40B).

Figure 36:
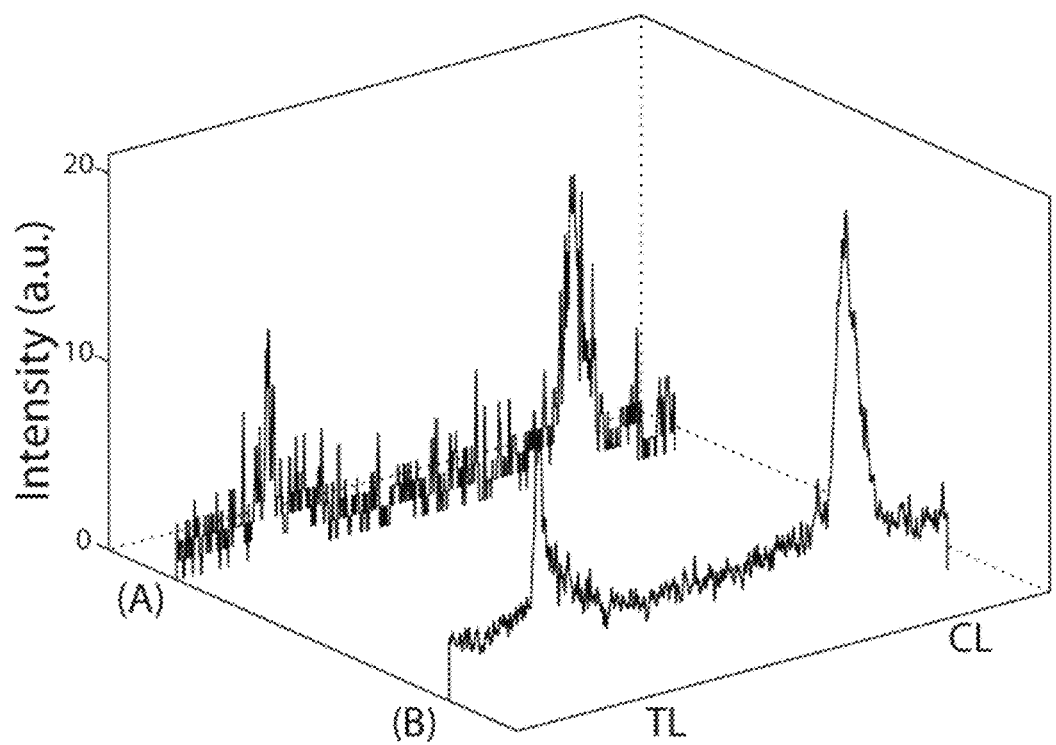
FIG. 36 shows line scans down the length of a lateral flow strip run with NeutrAvidin phosphorescent reporters with 1 ng/mL biotinylated lysozyme as the analyte. Images were acquired with an iPhone 5s. Line scan from the middle of the lateral flow strip from a single image, line (A). Line scan from the middle of the same lateral flow strip but from an average of 40 images, illustrating a decrease in the noise from image averaging, line (B).
Figure 37:
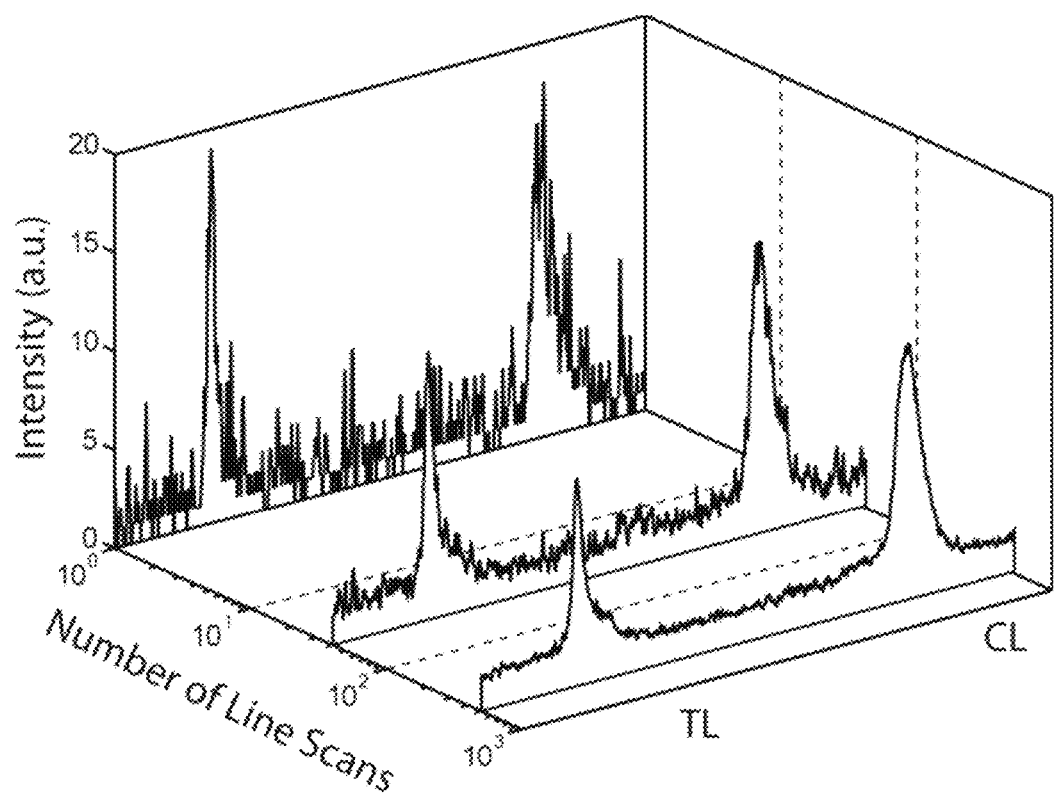
FIG. 37 illustrates an alternate method to image averaging for obtaining line scans of LFA strips with a high signal-to-noise ratio, using the same model system with biotinylated lysozyme analyte at 1 ng/mL and NeutrAvidin phosphorescent reporters as in FIG. 36. In this case, a single image is taken of a lateral flow strip and multiple line scans down the length of the strip from that single image are averaged.
Figure 38:
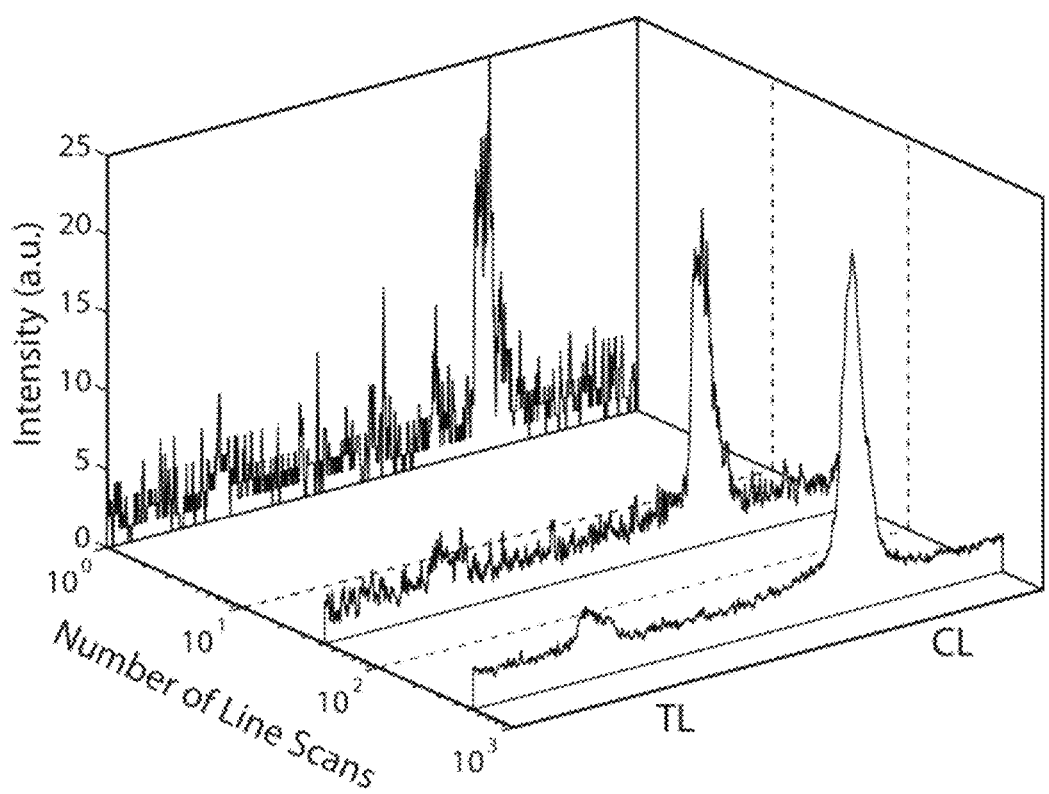
FIG. 38 shows the imaging averaging method presented in FIG. 37, but with an analyte concentration of 0.1 ng/mL.

The Applicants have shown that various averaging techniques can be used to enhance the detectability of phosphorescent reporters by noise reduction. FIG. 36 shows a line scan from a single image of a lateral flow strip run with NeutrAvidin phosphorescent reporters, and a line scan from the average of multiple images of the same strip, demonstrating the effectiveness of image averaging at reducing the noise level. This image averaging approach is also shown in FIG. 39 with a low analyte concentration at 0.1 ng/mL. FIG. 37 shows a single line scan and averages of multiple line scans obtained from a single image of a LFA strip. This line scan averaging approach can allow analyte detection from an individual relatively noisy image of luminescence from phosphorescent reporters. The effectiveness of line scan averaging is further demonstrated in FIG. 38 wherein the test line peak in the intensity profile becomes readily distinguishable from the noise after averaging multiple line scans. A combination of both imaging averaging and line scan averaging can be used to enhance the detectability of the signal from phosphorescent reporters.

In some embodiments, phosphorescent reporters may be incorporated into tests, such as, but not limited to, LFAs, flow-through assays, dip-stick assays, lab-on-a-chip assays, agglutination assays, microfluidics, paper microfluidics, microplate assays, multiphase systems, immuno-PCR, or other assay formats. In some embodiments, these tests may be read, interpreted, or analyzed using an electronic device with some type of light detector. In some embodiments the electronic device is a portable electronic device such as a cell phone, smart phone, personal digital assistant, smart watch, tablet computer, notebook computer, or laptop computer. In some embodiments, the portable electronic device may be connected to an attachment such as the one illustrated in FIGS. 43A-43C. In some embodiments, said attachment can serve several purposes which may include blocking out background and ambient light, holding a test cartridge or device in a position to enable detection of luminescence from phosphorescent reporters, providing a light source for photoexcitation of phosphorescent reporters, redirecting light arising from the portable electronic device to illuminate or photoexcite the phosphorescent reporters, providing other elements such as heating elements or electronic circuitry for signal enhancement or other functions or processes in an assay such as denaturation, hybridization, amplification, electrophoresis, and others.

In some embodiments the portable electronic device for assay readout of tests that use phosphorescent reporters can transmit results from the tests to other electronic devices, a network, cloud, database, or information system for further analysis, interpretation, or storage. In some embodiments, such as for epidemiological surveys and studies, the portable electronic device is capable of geotagging an individual test, such that the geographical location and time at which the test was performed are recorded.

It is often desirable to have a reporter that is also magnetic, as this can be useful in sample preparation, for pre-concentration of analyte before running an assay, or other procedures that result in general improvement of assay performance. The phosphorescent reporters can be made magnetic by binding them to magnetic nanoparticles, by simultaneous encapsulation of phosphors and magnetic nanoparticles, or by other means.

It is reported that inorganic phosphorescent particles can be effectively darkened or de-excited by photostimulation with long wavelength electromagnetic radiation like a red laser or infrared light. This optical property could be exploited in several analytical assay formats that use phosphorescent reporters. For instance, laser illumination could be used to reduce the emission brightness of all or a subset of phosphors, especially phosphors located specifically in a particular area, or which are unshaded.

In the present disclosure, excitation of the phosphorescent labels is preferably achieved using light, and therefore the measured luminescence is classified as photoluminescence, and the excitation by light of the phosphorescent labels is called photoexcitation. In the present disclosure, the phosphorescent labels are preferably excited with visible or UV light, but can also be excited by photons at other wavelengths of the electromagnetic spectrum. It should be noted that inorganic phosphors, such as the strontium aluminate phosphors discussed herein can also be excited or stimulated to emit luminescence by means other than photoexcitation, including but not limited to, bombardment with electrons or ions, application of an oscillating, alternating, or constant current, injection of charge carriers, heating, or the application of an electric field or electric potential difference across a region of space where the phosphorescent particles are located, giving rise to cathodoluminescence or electroluminescence. In some embodiments, the phosphorescent reporter can be detected by using a device or instrument that exploits the Destriau effect, in which a phosphor exhibits, sustained luminescence from the application of an oscillating electric field. For example, one can construct an analytical instrument where phosphorescent labels, in the presence of an analyte, bind in a region of interest located near or within a device like a capacitor that applies a direct or alternating electric field such that it gives rise to luminescence or electroluminescence.

An example of such a device for stimulating electroluminescence from phosphorescent reporters in a LFA is presented in FIGS. 42A-42B. In this device, the phosphorescent reporters are located in a region between two electrodes, and at least one of the electrodes is transparent to allow transmission of luminescence to a detector. The transparent electrode could be composed of both a transparent substrate with a transparent conducting film such as, but not limited to, indium tin oxide; fluorine doped tin oxide, doped zinc oxide, carbon nanotubes, graphene, or transparent conducting oxides. The transparent substrate could be composed of a variety of materials including, but not limited to, glass, transparent metal oxide, polymer, polymer blend, polymer composites, and others.

In some embodiments, the phosphorescent reporters can be detected using a device or an instrument that exploits the Gudden-Pohl effect, where a phosphor that was previously excited by visible or UV light emits luminescence or a momentary flash of light upon the application of an electric field, and the emitted light is detected, indicating the presence or absence of an analyte. In some embodiments, the phosphorescent reporters are excited by a combination of electromagnetic radiation and applied electric fields give rise to luminescence, which is detected, indicating the presence or absence of an analyte.

In some embodiments, the phosphorescent reporters are initially photoexcited then heated to elevated temperatures, giving rise to thermoluminescence which is detected, to indicate the presence or absence of an analyte. Heating the phosphorescent reporters may be carried out by various means, including but not limited to exothermic chemical reactions, phase changes of materials near the phosphorescent reporters, crystallization, condensation, electromagnetic radiation, corpuscular radiation, ion bombardment, induction, conductive heating, convective heating, frictional heating or a combination thereof.

The applications discussed in the preceding paragraphs mention assays in which detection of analyte involves direct binding of the reporter to the analyte at or in a specific region of interest and an increase in luminescence from the region of interest indicates a positive signal. In another embodiment, a readout method by which the analyte is detected is by determination of the presence or absence of the label in locations different from the locations expected in the absence of the analyte. Of particular interest are homogeneous assays, in which binding (or the suppression of binding, or competition) gives rise to the presence or absence of a signal. For instance, a phosphorescent label can be displaced from a pre-specified region by the presence of analyte, and then a decrease in luminescence from that region or an increase in luminescence elsewhere would indicate a positive signal.

Sample Preparation

In various embodiments, analytical processes can include one or more sample-preparation steps. In some embodiments, the sample preparation steps may utilize various sample preparation agents. In some embodiments, sample preparation may include, without limitation, concentrating, enriching, and/or partially purifying analytes of interest.

In some embodiments, sample preparation may include, without limitation, use of various concentrations of a dilute species from a liquid or gaseous environment using a filter, isolation of a subset of cells from a complex blood sample, breakage of cells to liberate analytes of interest, extraction of the analyte from a solid sample, or removal of lipids and particulates which could interfere with later analysis.

In some embodiments, sample preparation may involve amplification of the analyte to be detected. For instance, in some embodiments, amplification may include the use of the polymerase chain reaction to amplify nucleic acids or nucleation chain reaction to amplify prion proteins, or growth of an organism. Another way to amplify the detectability of a label is to grow an assembly of biomolecules, such as an actin filament or immune complex. Another method is to use a nucleating agent (e.g., of bubbles, crystals or polymerization) as an element of the label. Where available, these methods can greatly facilitate subsequent analysis.

Analytes of Interest

The methods and phosphorescent reporters of the present disclosure may be utilized to detect various analytes of interest from various specimens. For instance, in some embodiments, analytes of interest include, without limitation, genomic DNA, methylated DNA, specific methylated DNA sequences, messenger RNA, fragmented DNA, fragmented RNA, fragmented mRNA, mitochondrial DNA, viral RNA, microRNA, in situ polymerase chain reaction (PCR) product, polyA mRNA, RNA/DNA hybrid, pathogen DNA, pathogen RNA, replication protein A (RPA) amplification product, loop-mediated isothermal amplification product (LAMP), metabolite, metabolic intermediate, hormone, pathogen, virus, bacterium, fungus, organelle, biomarker, lipid, carbohydrate, protein, glycoprotein, lipoprotein, phosphoprotein, specific phosphorylated or acetylated variant of a protein, or viral coat proteins, cell surface receptor, protein, nucleic acid, mRNA, genomic DNA, PCR product, cDNA, peptide, hormone, drug, spore, virus, SSU RNAs, LSU-rRNAs, 5S rRNA, spacer region DNA from rRNA gene clusters, 5.8S rRNA, 4.5S rRNA, 10S RNA, RNAseP RNA, guide RNA, telomerase RNA, snRNAs—e.g. U1 RNA, scRNAs, Mitochondrial DNA, Virus DNA, virus RNA, PCR product, human DNA, human cDNA, artificial RNA, siRNA, enzyme substrate, enzyme, enzyme reaction product, Bacterium, virus, plant, animal, fungus, yeast, mold, Archaea; Eukaryotes; Spores; Fish; Human; Gram-Negative bacterium, *Y. pestis*, HIV1, *Bacillus anthracis*, Smallpox virus, *Cryptosporidium parvum*, Chromosomal DNA; rRNA; rDNA; cDNA; mt DNA, cpDNA, artificial RNA, plasmid DNA, oligonucleotides; PCR product; Viral RNA; Viral DNA; restriction fragment; YAC, BAC, cosmid, hormone, drug, pesticide, digoxin, insulin, HCG, atrazine, anthrax spore, teichoic acid, prion, chemical, toxin, chemical warfare agent, biological warfare agent, pollutant, Genomic DNA, methylated DNA, messenger RNA, fragmented DNA, fragmented RNA, fragmented mRNA, mitochondrial DNA, viral RNA, microRNA, in situ PCR product, polyA mRNA, RNA/DNA hybrid, protein, glycoprotein, lipoprotein, phosphoprotein, specific phosphorylated variant of protein, virus, or a chromosome.

Analyte Source

Analytes to be detected or quantified may be isolated from various sources. For instance, in some embodiments, analytes may be isolated from cells, body fluids, tissues, a biopsy specimen, blood, serum, plasma, stool, saliva, sweat, sputum, vomit, CSF, lavage fluid, tears, ocular fluids, transcellular fluid, urethral or genital secretions, exudate from lesions or areas of inflammation, nasal wash, nasal swab, throat swab, urine, hair, cell lysate, circulating tumor cells, FNAB cells, FACS fraction, immunomagnetic isolate, air filtrate, FFPE slices, fresh-frozen specimens, drinking water, natural water, sea water, soil water, soil leachate, fresh tissue, frozen tissue, neutral formalin-treated tissue, a formalin fixed paraffin embedded tissue block, an ethanol-fixed paraffin-embedded tissue block, a blood sample, air filtrate, tissue biopsy, fine needle aspirate, cancer cell, surgical site, soil sample, water sample, whole organism, spore, genetically-modified reporter cells, animal or human body fluids (blood, urine, saliva, sweat, sputum, vomit, sperm, biopsy sample, forensic samples, tumor cell, vascular plaques, transplant tissues, skin, urine; feces, cerebrospinal fluid); swabs from a human or animal, swabs from any of the aforementioned animal or human body fluids, agricultural products (grains, seeds, plants, meat, livestock, vegetables, rumen contents, milk, etc.); soil, air particulates; PCR products; purified nucleic acids, amplified nucleic acids, natural waters, contaminated liquids; surface scrapings or swabbings; biofilms, animal RNA, cell cultures, pharmaceutical production cultures, CHO cell cultures, bacterial cultures, virus-infected cultures, microbial colonies, FACS-sorted population, laser-capture microdissection fraction, magnetic separation subpopulation, FFPE extracts, and combinations thereof. In some embodiments, an entire sample source may be analyzed. In some embodiments, only a portion of a sample source may be analyzed.

In some embodiments the analyte to be detected may be obtained from surfaces or components of clothing, shoes, garments, personal protective gear and personal equipment, or other gear, equipment or objects in the vicinity of or near a facility for the production of agricultural or food products. In some embodiments the analyte to be detected may be obtained from any surfaces or components of objects suspected of contamination with illicit substances or hazardous materials or analytes associated with the production of illicit substances or hazardous materials.

Sample Pre-Treatment

The samples to be analyzed may be pre-treated in various manners. For instance, in some embodiments, the samples may be pre-treated by centrifugation, sedimentation, fractionation, field-flow fractionation, elutriation, monolithic separation, extraction, adsorption, protease, nuclease, dialysis, osmosis, buffer exchange, partitioning, washing, de-waxing, leaching, lysis, osmolysis, amplification, denature/renaturation, crystallization, freezing, thawing, cooling/heating, degasification, sonication, pressurization, drying, magnetophoresis, electrophoresis, dielectrophoresis, acoustophoresis, precipitation, microencapsulation, sterilization, autoclaving, germination, culturing, PCR, disintegration of tissue, extraction from FFPE, LAMP, NASBA, emulsion PCR, phenol extraction, silica adsorption, immobilized metal affinity chromatography (IMAC), filtration, affinity capture, capture from a large volume of a dilute liquid source, air filtration, surgical biopsy, FNA, flow cytometry, laser capture microdissection, and combinations thereof.

Analyte Modification

The analytes of the present disclosure can be modified in various manners. In some embodiments, the analytes can be modified by labeling, conjugation, methylation, esterification, dephosphorylation, phosphorylation, acetylation, deacetylation, methylation, demethylation, denaturation, conjugation, haloacetic acid modification, hatching, growth, excystation, passaging, culture, de-blocking, proteolysis, nuclease digestion, cDNA preparation, amplification, DNA ball preparation, PEGylation, clonal amplification, multiplication, charge enhancement, hybridization, antibody binding, adsorption, aptamer binding, photo-linking, reduction, oxidation, and combinations thereof.

Label Elements

In some embodiments, the analytes of the present disclosure may be labeled by various elements. In some embodiments, the label elements which can be part of, all of, associated with, or attached to labels include a nanoparticle, gold particle, silver particle, silver, copper, zinc, iron, iron oxide, or other metal coating or deposit, polymer, drag tag, magnetic particle, buoyant particle, microbubble, metal particle, charged moiety, silicon dioxide, with and without impurities (e.g., quartz, glass, etc.), poly(methylmethacrylate), polyimide, silicon nitride, gold, silver, quantum dot, CdS, carbon dot, a phosphor such as silver-activated zinc sulfide or doped strontium aluminate, a fluor, a quencher, polymer, PMMA, polystyrene, retroreflector, bar-coded or labeled particle, porous particle, pellicular particle, solid particle, nano shells, nanorods, IR absorbers, microwave absorbers, microspheres, liposomes, microspheres, polymerization initiators, photografting reagents, proteins, molecular recognition elements, linkers, self-assembled monolayers, PEG, dendrimers, charge modifiers, PEG, silane coupling agents, initiators of growth from polymer grafts from the label surface, stabilizing coatings, zwitterions, zwitterionic peptides, zwitterionic polymers, magnetic materials, magnetic materials of Curie temperature below 200° C., enzyme, microbial nanowires, DNA including aptamer sequences, phage modified for conductivity, fusions or conjugates of detectable elements with molecular recognition elements, Streptavidin, NeutrAvidin, Avidin, or biotin-binding proteins, biotin, biotinylated molecules, biotinylated polymers, biotinylated proteins, anti-antibody aptamer, aptamer directed to antibody-binding protein, an azide or terminal alkyne or other click chemistry participant, and combinations thereof.

Synthesis Methods

In some embodiments, the phosphorescent core of a phosphorescent reporter is prepared by a solid state synthesis method, wherein metal oxides or precursors of the elements of the desired final phosphorescent core are blended, and heated, calcined or calcinated, annealed, or sintered at high temperatures ranging from a few hundred degrees Celsius to two thousand degrees Celsius under reducing or inert conditions in a controlled atmosphere. In some embodiments a flux such as boric acid is added to improve the annealing process by allowing reduced temperatures, improved crystallinity, or leading to phosphorescent powders with better optical and luminescence properties. In some embodiments, the phosphorescent core is prepared by a combustion synthesis method, wherein the precursors are in the form of oxides or salts, typically nitrates, which are mixed in a solvent. A combustible fuel such as urea is added to the solution which is then mixed and heated to a few hundred degrees Celsius, triggering ignition, and forming a material, which may then be further reduced to improve the luminescence properties by annealing at high temperature in a controlled atmosphere. In some embodiments, the phosphorescent core is prepared by sol-gel synthesis techniques, which involve hydrolysis of the precursors in a liquid solution or colloidal dispersion, followed by drying and calcination or annealing. In some embodiments the phosphorescent core is prepared by microemulsion methods wherein immiscible components such as water and oil are combined in the presence of stabilizing components such as surfactants, alcohols, or small organic molecules. The precursors to the elements in the final phosphorescent material are added in addition to a fluxing agent, and the mixture is heated to elevated temperatures under a reducing atmosphere, and possibly annealed or calcined further to produce an inorganic phosphorescent material.

Surface Modification Methods

In some embodiments the phosphorescent core may be treated to reduce degradation of the phosphorescent core by water, chemicals, or other compounds which may come in contact with the core. In some embodiments the phosphorescent core is encapsulated or coated in a material to prevent degradation of the core. In the preferred embodiment, the material that encapsulates the core is composed of silica or silicon oxide. In some embodiments the phosphorescent core may be encapsulated by reactions with phosphoric acid. In some embodiments the phosphorescent core may be encapsulated using triethanolamine or similar compounds. In some embodiments the phosphorescent core may be encapsulated with iron oxide or magnetic materials. In some embodiments the phosphorescent core is encapsulated in a metal oxide such as alumina. In some embodiments the phosphorescent core may be encapsulated in a polymeric material such as, but not limited to, polystyrene, PEG, polyethylene, polyamides, polyurethanes, polyethers, polyesters, polymers of halogen-substituted olefins, acrylic or acrylate polymers, silicon-based polymers such as poly(dimethylsiloxane), polymers of alkenes, polycarbonates, electroactive polymers, ferroelectric polymers, liquid crystalline polymers, or others. In some embodiments the phosphorescent core is encapsulated in a polymer composite or polymer blend. In some embodiments the phosphorescent core may be encapsulated or coated with copolymers or blends of any of the aforementioned polymers. In some embodiments the material encapsulating the phosphorescent core may contain fluorescent dyes, preferably those with different emission wavelengths than the core. In some embodiments, the phosphorescent core is encapsulated with a combination of materials such as an inner layer of silica on the phosphorescent core and a polymer matrix layer on the silica layer.

In some embodiments the surface of the encapsulated particle is treated to have reactive groups for covalent coupling of molecules such as, but not limited to, polymers, ligands, molecular recognition elements, photoluminescent dyes, peptides, zwitterionic molecules, nucleic acids, or others. In some embodiments the surface of the encapsulated particle is treated for improved colloidal stability and reduced aggregation or non-specific binding in assays. In some embodiments, molecules with reactive groups for covalent coupling or enhanced adsorption of molecular recognition elements are introduced to the surface of the encapsulated particle. In some embodiments these molecules may include heterobifunctional polymers, homobifunctional polymers, and polymers with multiple side chains or reactive groups for coupling. In some embodiments the surface of the encapsulated polymer may be modified with activators for grafting polymers from the surface by radical polymerization, atom-transfer radical polymerization, living polymerization, step growth polymerization, or condensation polymerization. In some embodiments the surface of the encapsulated particle may be treated to have reactive groups to allow grafting of polymers to the surface from solution. In some embodiments the surface is modified by reactive silanes such as triethoxysilylbutyraldehyde or (3-aminopropyl) triethoxysilane. In some embodiments, other compounds are added during surface modification for improved stability, such as adding 1,2-bis-(triethoxysilyl) ethane or bis(3-(trimethoxysilyl) propylamine during silanization. In some embodiments, the surface of a phosphorescent reporter is modified by covalent attachment of molecular recognition elements. In some embodiments, the surface of a phosphorescent reporter is modified by adsorption of molecules for colloidal stability or molecular recognition.

Molecular Recognition Element

In some embodiments, the label elements of the present disclosure may also be associated with various molecular recognition elements. In some embodiments, the molecular recognition elements may be part of, associated with, or attached to labels. In some embodiments, molecular recognition elements can include, without limitation, antibody, antibody fragment, antibody analog, affibody, camelid or shark antibody analog, nucleic acid, carbohydrate, aptamer, ligand, chelators, peptide nucleic acid, locked nucleic acid, backbone-modified nucleic acid, DARPin, molecularly imprinted polymers, lectin, padlock probe, substrate, receptor, viral protein, mixed, cDNA, metal chelate, boronate, peptide, enzyme substrate, enzyme reaction product, lipid bilayer, cell, tissue, microorganism, yeast, bacterium, parasite, protozoan, virus, antigen, hapten, biotin, hormone, drug, anti-RNA/DNA hybrid antibody, mutS, anti-DNA antibody, anti-methylation antibody, or an anti-phosphorylation antibody.

Many analytical methods, including those of interest in the present invention, involve molecular recognition, and also transduction of the molecular recognition event into a usable signal. Molecular recognition refers to the high affinity and specific tendency of particular chemical species to associate with one another, or with organisms or viruses displaying target chemical species. Well-known examples of molecular recognition include the hybridization of complimentary DNA sequences into the famous double helix structure with very high affinity, and the recognition of foreign organisms or molecules in the blood stream by the antibodies produced by mammals, or selected analytes by deliberately selected monoclonal antibodies. There are many other examples of molecular recognition elements, including the recognition of carbohydrate molecules by lectins, nucleic acid recognition by proteins and nucleic acid analogs, the binding of analytes by antibody fragments, derivatives, and analogs, and a host of other examples.

Amplification or Signal Enhancement Methods

In some embodiments, the molecular recognition event may be read into a usable signal. In some embodiments, the signal may be amplified or enhanced by a signal enhancement method, which may act upon the analyte, a label, or a component of the label. In some embodiments, the signal amplification or enhancement method may include hatching, growth, PCR, solid-phase PCR, RPA, LATE, EATL, or hot-restart amplification, solid-phase RCA, silver staining, metal deposition or plating, nickel, copper or zinc deposition, gold particle growth, polymerization, particle binding, grafting, photografting, click chemistry, a copper(I)-catalyzed 1,2,3-triazole forming reaction between an azide and a terminal alkyne, and combinations thereof.

In some embodiments, the luminescence signal from the label elements may be read or detected by an optical sensor such as, but not limited to, a charge-coupled device (CCD) sensor, CCD image sensor, complementary metal-oxide-semiconductor (CMOS) sensor, CMOS image sensor, camera, cell phone camera, photodiode, avalanche photodiode, single-photon avalanche diode, superconducting nanowire single-photon detector, photoresistor, photomultiplier, photomultiplier tube, phototube, photoemissive cell, photo switch, phototransistor, photonic crystal, fiber optic sensor, electro-optical sensor, luminometer, or fluorometer. In some embodiments the luminescence signal from the label elements may be read, detected, or inferred from photochemical reactions, such as those that occur in photographic film, with the photochemical reactions stimulated or initiated by luminescence from the label elements. In some embodiments the luminescence signal from the label elements may be read or detected visually by the naked eye, or with the assistance of an optical amplifier or intensifier.

In some embodiments, the luminescence signal or the signal-to-noise ratio may be enhanced or amplified by cycling the process of photoexcitation and subsequent time-delayed detection of the resulting photoluminescence from the label elements, followed by averaging the data from the cycles. One specific example of this cycling process is the use of a cell phone as a luminescence detection system, wherein the cell phone camera flash is used as the photoexcitation source and the cell phone camera is use as a light detector for imaging luminescence emitted by the label elements. The cell phone camera flash is periodically switched on and off, such that while in the "on" state the label elements are subjected to photoexcitation, and when the light is in the "off" state the luminescence emitted by the label elements is detected by the cell phone camera. The resulting images from the cycling process are averaged or stacked, resulting in an amplified signal or higher signal-to-noise ratio. This cycling process is not limited to a cell phone camera and flash; the flash can be replaced with any source of light suitable for photoexcitation such as, but not limited to, a laser, laser diode, light emitting diode (LED), organic light emitting diode (OLED), incandescent bulb, fluorescent bulb, compact fluorescent lamp, xenon lamp, mercury lamp, halogen lamp, plasma display, liquid crystal display, candle, sunlight, or others. The cell phone camera can be replaced with any suitable detection system such as those described herein.

In some embodiments, the luminescence signal from the phosphorescent reporters can be enhanced by using index-matching techniques. Index matching, in this context, involves immersing a porous material such as a membrane used in lateral flow or paper microfluidics in a solvent with a similar index of refraction, thereby reducing light scattering and improving light transmission. Index matching can improve the detectability of the luminescence signal from phosphorescent reporters by both improving photoexcitation and reducing the loss of luminescence from a phosphorescent reporter by scattering.

In some embodiments, where luminescence detection from phosphorescent reporters is carried out using a device with more than one type of light detection element, such as the red, green, and blue pixels in a typical RGB color camera, the signal from phosphorescent reporters can be enhanced by calculating luminance values with weighting factors that account for the emission spectrum of the phosphorescent reporter and the respective quantum yields of the red, green, and blue channels. For instance, the calculated luminance from a given RGB image of green strontium aluminate phosphorescent reporters that have an intense emission peak near 520 nm would have a strong weighting towards the green channel and a lighter weighting towards the red channel.

Specificity Enhancement

In some embodiments, the specificity of detection of analytes may be enhanced through removal of non-specifically bound labels by chemical or physical means. In some embodiments, chemical means of removal include denaturants, temperature, acids, bases, osmolytes, surfactants, polymers, and solvents. In some embodiments, physical means of removal include force, vibration, buoyancy, centrifugation, sedimentation field-flow, magnetic force, electrophoretic force, dielectrophoretic force, sonication, and lateral force. In some embodiments, susceptibility to means of removal may be enhanced by incorporation of moieties particularly responsive to means of removal, such as charged or dense moieties for electrophoretic or sedimentation-based removal.

Location of Analysis

Various locations may be used for sample analysis. In some embodiments, the location of the steps of the analysis, which may be used singly or in combination, include microtiter plates, tubes, the surfaces of particles or beads, nanowell arrays, flow injection analysis apparatus, microfluidic chips, conductive surfaces, temperature-controlled environments, pressure chambers, ovens, irradiation chambers, electrophoretic, field-flow and chromatographic apparatus, microscope stages, luminometers, Coulter principle devices, cantilever and FET sensors, vacuum chambers, electron optical apparatus, single-molecule detection apparatus, single-molecule fluorescence detection apparatus, surfaces bearing electrodes or pillars, emulsions, lateral flow membranes, flow through membranes, lateral flow assay readers, flow through assay readers, gel documentation systems, robotic apparatus, and combinations thereof. Rotation and flow devices, or fast electronic or mechanical shutters, enhance sensitivity by allowing detection of luminescence before it decays very far. Flow injection analysis, "Lab on a chip" and "Lab on a CD" approaches can be desirable in some embodiments. In some embodiments, it may be advantageous to perform more than one type of analysis in series, either fractionating a sample using or based on the results of one method before performing an additional method, or by interpreting together the results of multiple methods.

ADDITIONAL EMBODIMENTS

Reference will now be made to various embodiments of the present disclosure and experimental results that provide support for such embodiments. Applicants note that the disclosure herein is for illustrative purposes only and is not intended to limit the scope of the claimed subject matter in any way.

Example 1

Preparation of Silica Encapsulated Phosphorescent Particles

Phosphorescent strontium aluminate powder prepared by a process such as solid state synthesis, combustion synthesis, sol-gel synthesis, or microemulsion synthesis is dispersed in anhydrous ethyl acetate at a concentration of about 0.1 g/mL in a zirconia milling jar containing cylindrical or spherical zirconia grinding media on a U.S. Stoneware ball mill for 6-9 days under continuous operation. After milling, the dispersion of phosphors is collected and the ethyl acetate is removed by evaporation. Colloidal suspensions of milled strontium aluminate phosphorescent particles are prepared at a concentration of 1-5 mg/mL in ethanol in 50 mL centrifuge tubes or larger containers suitable for centrifugation. Demarcation lines on the tubes mark the distance that a particle of larger than a specific size will settle over a defined period of time (e.g. 10 minutes) at a specific relative centrifugal force. After centrifugation, the supernatant (i.e. the liquid above the demarcation line) containing the small particles are collected and the particles are concentrated by further centrifugation. Fractionation may be carried out to remove particles smaller than the minimum desired size by centrifuging to induce settling, and removing the supernatant containing the small particles. The centrifugation process is repeated until a fraction with a desirable concentration and coefficient of variation is obtained. Silica encapsulation is carried out by preparing a solution with approximately 1 mg/mL of phosphorescent particles suspended in a 1:4 water/ethanol mixture containing 20 mM tetraethoxysilane and 0.25 M ammonia. Silica encapsulation is carried out for 7-8 hours, after which the reaction is stopped and the particles are washed in ethanol to remove excess reagent.

Example 2

Preparation of PEGylated Phosphorescent Reporters by a "Grafting to" Method

Surface aldehydes are introduced to silica encapsulated phosphorescent particles by reacting 1 mg/mL of phosphorescent particles in ethanol containing 5% v/v water and 50 mM TESBA for 30-60 minutes. 1-2-Bis-(triethoxysilyl) ethane (BTEOSE) at 10-100 mM may be added with the TESBA for improved hydrolytic stability of the grafted PEG, with the exact TESBA/BTEOSE ratio depending on the desired PEG coverage. The reaction is stopped, and the particles are washed in ethanol then cured under reduced pressure at elevated temperature (e.g. 36-50° C.). The aldehyde-functionalized particles are suspended in an aqueous buffer with 50-250 mM sodium cyanoborohydride reducing agent and approximately 0.5 mM $H_2N$-PEG-COOH until desired PEGylation is achieved. Washing can be carried out with aqueous solution. Bioconjugation is carried out by carbodiimide chemistry by used a combination of EDC and NHS to activate the carboxyl groups, followed by addition of proteins or molecular recognition elements containing amine groups, which react to form amide bonds with the activated carboxyls. Passivation may be carried out using one or more solutions containing a blocking protein, such as bovine serum albumin or casein, or small molecules that will react with the activated carboxyls like ethanolamine or hydroxylamine.

Example 3

Oriented Immobilization of Antibodies by Reductive Amination

Silica encapsulated phosphorescent particles are functionalized with aldehydes by TESBA as described previously. Homobifunctional amine-PEG-amine, preferably with a molecular weight from 3,400-10,000 g/mol is added to a phosphate buffer containing aldehyde functionalized phosphorescent particles with at least 50 mM sodium cyanoborohydride reducing agent. The molar concentration of amine-PEG-amine added during grafting should be at least 1-2 orders of magnitude in excess of the maximum amount of PEG chains needed to coat all of the particles in the colloid with a monolayer. The number of bifunctional PEG molecules needed for a monolayer on a single particle can be estimated by considering the average surface area of a particle, and typical values for the theoretical packing density of PEG (e.g. 5 chains/nm$^2$). An insufficient amount of amine-PEG-amine can result in covalent coupling of both amine groups of the molecule to the surface aldehydes. PEGylation may be carried out for as little as a few hours to 24 hours or more at room temperature. The reaction may be stopped by buffer exchange, and the particles should be washed in water or buffer. The antibodies to be coupled to the amine-PEGylated phosphorescent particles may be covalently bonded in an oriented manner that improves binding effectiveness compared to other immobilization methods. The polysaccharides on the antibodies, which are located near the Fc region, may be oxidized with 1 mM sodium periodate at room temperature for about 30 minutes or reduced temperature (e.g. 4° C.) for 2 hours in either phosphate buffer or sodium acetate buffer with the antibodies at a concentration around 1 mg/mL. The amine-PEGylated phosphorescent particles and the antibodies, now containing aldehydes from the periodate treatment, may be coupled by reductive amination with sodium cyanoborohydride as previously described.

Example 4

Oriented Immobilization of Antibodies by Click Chemistry

Silica encapsulated phosphorescent particles are modified with surface aldehydes from TESBA as previously described or with APTES followed by reductive amination with 10-100-fold excess glutaraldehyde. Amine-PEG-alkyne molecules, preferably with molecular weights from 3,400-10,000 g/mol are mixed in a phosphate buffer between pH 6 and 8 with the aldehyde functionalized phosphorescent particles in the presence of sodium cyanoborohydride until desired PEG coverage is achieved. The terminal alkyne group of the PEG chain can be coupled very specifically with fast kinetics to an azide group. The polysaccharides of the Fc of an antibody can be modified to contain azide groups. Mixture of the modified antibodies in the presence of alkyne-PEG phosphorescent particles in the presence of a copper catalyst at room temperature will result in covalent attachment of antibodies to the particles in an oriented manner with better functionality.

Example 5

Detection of Dengue NS1 from Whole Blood in Lateral Flow Assay

Water-stabilized phosphorescent particles are prepared and functionalized using a hydrophilic or zwitterionic polymer linker with functional groups for covalent coupling of anti-Dengue virus nonstructural protein 1 (NS1) antibodies. Anti-NS1 phosphorescent reporters are loaded into a conjugate release pad such as that shown in FIGS. 41A-41C by dispensing, spotting, or immersion with additives for improved stabilization, consistency and speed of conjugate release during the LFA test, and reduced non-specific binding of phosphorescent reporters within the LFA test strip. Additives may include various surfactants such as Tween or Triton, polymers such as PEG, poly (vinyl alcohol), and saccharides or polysaccharides such as trehalose. The conjugate release pad material is selected to minimize the nonspecific binding of analyte and phosphorescent reporters to the pad, and in the preferred embodiment is a glass fiber membrane. A porous material capable of separating whole blood for analysis without significant red blood cell hemolysis is selected; such materials may include cotton, glass fiber membranes, or other porous membranes. A membrane with an appropriate pore size to allow effective transport of phosphorescent reporters and control the flow rate for optimal sensitivity or analyte detectability is selected. In the preferred embodiment, the membrane is constructed from nitrocellulose on a polymer-based backing support material. The membrane is spotted with a test line for analyte detection comprising anti-NS1 antibodies that are either polyclonal or monoclonal and bind to a different epitope of the NS1 protein than the antibodies on the phosphorescent reporters. The membrane is also spotted with a control line which may consist of some type of molecular recognition moiety that binds specifically to the phosphorescent reporters. An absorbent pad is selected to effectively wick the liquid sample through the strip, and ideally prevent backflow, which can hamper sensitivity. The entire LFA strip is encased in a housing material, which could be designed to fit into a portable electronic device attachment like that presented in FIGS. 43A-43C. A blood sample from 10-100 μL is collected an applied to the sample pad, followed by the addition of a wash or chase buffer to help drive the sample and phosphorescent reporters through the LFA strip. After a specific period of time (e.g. 10 minutes), the LFA test cartridge is loaded into the insertion port of the attachment, and the portable electronic device is used to detect luminescence from the phosphorescent reporters. The portable electronic device may have pre-loaded calibration data that can be used to determine the amount or concentration of NS1 in the sample. The data may be geotagged or uploaded to a network or server for storage or further processing or analysis.

Example 6

Gastrointestinal Multiplex Assay in Flow-Through Assay

Noroviruses are highly contagious pathogens that are often responsible for epidemics of gastroenteritis. However, a number of other pathogens such as *E. coli* and *Salmonella* can cause illness with similar symptoms. A rapid, sensitive point-of-care test that can allow multiplexing for gastrointestinal pathogens, and can work with relatively complex samples such as diluted stool would be an invaluable tool. In one embodiment of the present invention, a flow-through assay with phosphorescent reporters could be designed in which different sets of phosphorescent reporters functionalized with molecular recognition elements that bind to different analytes would be prepared. A membrane is functionalized with complementary molecular recognition entities in discrete spots, with each spot corresponding to a different pathogen. A sample is collected and mixed with phosphorescent reporters, allowing binding of the phosphorescent reporters to antigens in the sample. The sample is flown directly through the membrane, and the antigen-phosphorescent reporter complexes are captured specifically at the pre-defined spots on the membrane, allowing determination of which pathogen is the cause of illness.

Example 7

Detection of Nucleic Acids

In some embodiments, phosphorescent reporters may be used to detect specific sequences of nucleic acids. Nucleic acids may be detected from a variety of sample types depending on the application, such as tumor cell lysates for cancer diagnostics. Many nucleic acid tests may involve an amplification step by polymerase chain reaction (PCR), isothermal PCR, loop-mediated isothermal amplification (LAMP), or replication protein A (RPA) amplification. Phosphorescent reporters may be functionalized with single stranded DNA or RNA that hybridizes with part of a complementary strand from a sample that is specific to an analyte. In some embodiments the target complementary nucleic acid strand has a specific tag which is introduced during amplification or by other means, and allows the tagged strand to be captured by a surface that recognizes the tag. For example, an amplification product may be biotinylated so that it binds to surfaces coated with avidin. In other embodiments, the surface is functionalized with a nucleic acid strand that specifically hybridizes with a small segment of the target nucleic acid strand, which is long enough to also allow hybridization with a phosphorescent reporter containing a complementary sequence to a different part of the target nucleic acid strand.

Example 8

Spectral Multiplexing in a Lateral Flow Assay

Multiplexed lateral flow assays can be readily designed by adding multiple test lines to a strip and using reporters functionalized with different molecular recognition elements to bind specifically at each test line in the presence of an analyte. An alternate multiplexing method is to use different colored or spectrally distinct reporters that bind to different analytes. In one embodiment, phosphorescent reporters of the present invention can be used to distinguish infections caused by Chikungunya and West Nile virus, debilitating mosquito-borne illnesses. A test line is prepared with anti-human antibodies that bind specifically to human IgG antibodies. Phosphorescent reporters with distinct emission spectra, such as green- and red-emitting particles, are functionalized with antigens such as envelope proteins or non-structural proteins involved in viral replication that are specific to the different viruses. For illustration, red-emitting particles could be functionalized with antigens specific to Chikungunya, and green-emitting particles with antigens specific to West Nile. A patient infected with either virus for enough time to illicit an immune response will be seropositive for IgG antibodies that recognize those antigens. Therefore, Chikungunya infection will give a red test line and West Nile infection a green test line.

Example 9

Luminescence Detection with a Cell Phone

In some embodiments it is desirable to be able to carry out highly sensitive detection of analytes in point-of-care settings, and have the ability to link that data to information systems. This ability can be achieved readily using phosphorescent reporters and a number of different light detection systems, but of particular interest is the incorporation of phosphorescent reporter-based tests with portable electronic devices such as cell phones and tablet computers. Using the camera native to the portable electronic device to detect luminescence from the phosphorescent reporters can allow immediate automated analysis of the test by software in the device, and then display the results to the user. Robust quantification of analyte levels with the portable electronic device can be achieved using cycling of the time-gate phosphorescence detection method illustrated in FIG. 29 with image averaging methods presented in FIG. 36 and FIG. 39 for reduced noise. Line scan averaging methods shown in FIG. 37-38 and FIG. 40 can also be used to obtain sharp peaks or signals corresponding to analyte levels. The phosphorescent reporters of the present invention are likely the only photoluminescent reporters currently capable of sensitive time-gated phosphorescence imaging with cell phones and similar hardware. The organometallic dyes and metal chelates currently used in time-resolved detection schemes generally have lifetimes that are too short for the response times of a typical cell phone's optoelectronics system. The quantitative ability combined with the abilities of a cell phone, such as geotagging and network connectivity could be particularly useful in environmental monitoring applications where levels of pollutants could be quantified at specific locations, and the data then geotagged and sent to an institution or third party for decision making and management.

Example 10

Influenza Detection and Epidemiological Monitoring

Multiplexing methods disclosed herein could be used to distinguish between influenza A and influenza B infections, and could also identify infections caused by recent particularly virulent or threatening strains of the virus. Assay formats could use nasal swabs for sample collection with lateral flow cartridges for analyte detection. Combining the test with the information technology capabilities of a cell phone or tablet computer could be particularly useful in real-time monitoring of infectious disease incidence and geographic distribution. For example, during the outbreak of an epidemic of influenza, healthcare workers or people administering self-testing could use the test in combination with a cell phone and attachment like that shown in FIGS. 43A-43C for automated readout and analysis of the test. Information on the test results such as type of influenza strain and location could be encrypted with anonymous patient data, and updated to an information system that could inform the general population and healthcare workers on the current number of outbreaks of influenza in a particular region.

Example 10

Quantitative Drugs of Abuse Testing from Saliva

Small molecules such as drugs of abuse or metabolites of drugs of abuse can be detected using phosphorescent reporters. In some embodiments, a capture antibody that binds to the small molecule of interest is immobilized on a surface. When the small molecule binds to the antibody, the resulting complex has a different conformational structure that is specifically recognized by moieties on the phosphorescent reporters. In other embodiments, a competitive assay format is used in which a phosphorescent reporter and molecule analyte compete for binding sites. At high analyte concentrations, more of the phosphorescent reporters are displaced, resulting in decreased luminescence. When no analyte is present, the phosphorescent reporters completely occupy the binding sites, resulting in high luminescence intensity.

Example 11

Electroluminescence for Sensitive Analyte Detection

The phosphorescent reporters on the present invention can be stimulated to emit luminescence by the application of electric fields. Electroluminescence offers the potential for high sensitivity analyte detection by greatly reducing the background signal, as most materials used in a diagnostic test or in the sample matrix do not emit electromagnetic radiation under the electric fields needed to excite the phosphorescent reporters. Continuous light emission from the phosphorescent reporters by applying an alternating electric field over a certain period of time coupled with integrated light detection could improve sensitivity. Various systems for electroluminescence readout can be constructed, such as the one illustrated in FIGS. 42A-42B. Thin membranes or microfluidic chips can be engineered to contain electrodes that produce an electric field across a relatively small distance (e.g. 100 µm-2 mm) and allow detection of the resulting electroluminescence from the phosphorescent reporters. A combination of photostimulation and the application of electric fields could be used as well.

Example 12

Assay Readout by Eye

In some embodiments, tests that incorporate phosphorescent reporters may be interpreted visually by observing the presence or absence of luminescence in predefined locations. One could construct a device that blocks out ambient light and allows the user to see light specifically emanating from phosphorescent reporters. The device could incorporate a light source for photoexcitation, or hardware to induce electroluminescence or stimulate thermoluminescence. Lenses, such as plano convex lenses, bioconvex lenses, aspheric lenses, concave lenses, or combinations thereof could be added to the devise for increased magnification and visibility. In another embodiment, a device such as a handheld image intensifier may be used to assist in visual readout. Some image intensifiers are better suited for enhancing the signal from photons in the red to infrared region of the electromagnetic spectrum. Red zinc sulfide phosphors or phosphorescent strontium aluminate that emits red light as the result of doping with rare earth metals and transition metals such as chromium or manganese could be used directly in such an image intensifier readout application. In some embodiments, coupling red, near-IR, or IR fluorophores to the surface of a phosphor with an emission spectrum that overlaps with the excitation spectrum of the fluorophore could enhance the detectability by an image intensifier.

Example 13

Thermoluminescence Signal Amplification

The mechanism of persistent luminescence in inorganic phosphorescent solids is somewhat analogous to thermoluminescence, and involves trapping of charge carriers in metastable excited states, followed by gradual thermal release. The resulting luminescence is a function of temperature, and higher temperature can increase the electron-hole recombination rate, and therefore the luminescence intensity. The phosphorescent reporters in the present invention can be stimulated to have higher luminescence intensity by elevating the local temperature. In some embodiments, an assay could be designed to incorporate heating elements or use exothermic reactions to supply heat to increase the luminescence intensity from phosphorescent reporters, leading to more sensitive analyte detection.

Example 14

Self-Calibration and Assay Reliability Improvement Methods

In some embodiments, inorganic phosphorescent particles may be embedded or immobilized at some defined location in an assay or on a test cartridge surface to provide a known luminescence signal that can be used as a reference to calibrate the intensity of phosphorescent reporters used in the test. In some embodiments, at least two sets of phosphorescent particles that have different recognition moieties or emission spectra may be used in parallel in an assay as a means of calibrating the luminescence signal that results from analyte binding. In some embodiments, detection of the same analyte with different sets of phosphorescent reporters, such as particles with different emission wavelengths, may be used to improve the confidence in the test results and reduce the rate of false negatives and false positives.

Example 15

Flotation Assay

The flotation assay format as depicted in FIG. 35 offers a simple way to detect analytes with minimal user intervention and low risk of contamination of the local environment with a potentially dangerous analyte. A tube containing glass microbubbles functionalized with molecular recognition moieties for a specific analyte, phosphorescent reporters, and light absorbing dye such as food coloring are provided in a small closeable tube such as a PCR tube. A sample, such as whole blood or diluted stool, is added directly to the tube, which is then closed to minimize the risk of environmental contamination. The contents of the tube are mixed then allowed to settle, and any bubble-analyte-phosphorescent reporter complexes formed float to the top of the liquid. The light absorbing dye reduces background luminescence from the unbound phosphorescent reporters, and luminescence is detected specifically from reporters floating at the top of the liquid.

Example 16

Magnetic Phosphorescent Reporters

In some embodiments, it is particularly advantageous to have a reporter that has magnetic properties. For instance, magnetic phosphorescent reporters may be mixed with a sample and allowed to bind to at least one or more analytes, after which the magnetic reporters may be concentrated by applying a magnetic field, to enable the removal of unlabeled analyte. The removal of unlabeled analyte could greatly reduce or eliminate the high dose hook effect, which could extend the dynamic range of an assay. Additionally, applying the concentrated solution of magnetic phosphorescent reporters after removal of unlabeled analyte in a diagnostic test, such as a flow-through test or LFA, could improve the sensitivity or limit of detection of the assay. In other embodiments, magnetic properties can improve assay performance by applying magnetic fields to enhance mass transport of the reporters to a surface for detection. For instance, in a microplate or microfluidics format, the surface at the bottom of a well or channel is functionalized with molecular recognition moieties specific to an analyte. Allowing phosphorescent reporters to come in contact with the surface for binding is relatively slow when settling, sedimentation, and diffusion by Brownian motion are the primary driving forces for mass transport. However, the application of a magnetic field to drive magnetic reporters to the surface could reduce the total assay time and improve sensitivity. There are various strategies for preparing magnetic phosphorescent reporters. Iron oxide co-precipitation methods could be used to add a layer of superparamagnetic iron oxide directly on a shell encapsulating a phosphorescent core. Magnetic nanoparticles and phosphorescent cores may be encapsulated simultaneously using the methods described herein to produce hybrid particles with both phosphorescent and magnetic properties. In other embodiments, the surface of encapsulated phosphorescent particles may be functionalized with magnetic moieties or nanoparticles.

Applications and Advantages

An advantage of utilizing phosphorescent reporters of the present disclosure is that phosphorescence is sensitively detectable using simple or no instrumentation. Furthermore, the phosphorescent reporters of the present disclosure (e.g., strontium aluminate doped with rare earth metals) are relatively inexpensive and display higher quantum efficiencies, longer luminescence lifetimes, and higher relative intensities than many typical inorganic phosphors. In addition, the phosphorescent reporters of the present disclosure (e.g., strontium aluminate phosphors) are not prone to significant photodegradation or photobleaching, which is a significant problem with many photoluminescent labels. The lack of photobleaching means that tests using the phosphorescent reporters of the present disclosure can be excited and re-imaged or re-measured numerous times without significant loss of luminescence activity.

Due to their long emission lifetime, the phosphorescent reporters of the present disclosure can also be used in readout systems without continuous excitation. The primary advantages of time-resolved photoluminescence detection are reduced background autofluorescence from the sample matrix or assay materials, and the potential for designing a simpler assay readout device by eliminating the need for costly optical hardware such as filters. Virtually every type of photoluminescent label, aside from a select number of organometallic dyes or metal chelates, has short lifetimes and requires optical filters to reduce the background intensity from scattered excitation light and autofluorescence. Organic fluorescent dyes such as fluorescein that have a relatively narrow gap or Stokes shift between the peak of the excitation spectrum and the peak of the emission spectrum require the use high quality optical filters in assay readout devices for sensitive detection of the fluorophore and the analyte. In theory, photoluminescent labels that have excitation bands with a large Stokes shift from the emission band could be used in assays without optical filters by selecting a highly monochromatic excitation source. In practice, however, finding such an excitation source that is also cost effective is infeasible, as most excitation sources have an emission peak broad enough to cause a background signal that overlaps with the photoluminescent reporter's emission wavelengths, interfering with the detectability of the reporter and reducing the assay sensitivity. The phosphorescent reporters of the present invention can allow the construction of readout devices for highly sensitive photoluminescence assays with minimal optical hardware. In some embodiments, a simple device such as a cell phone camera and flash or LED are sufficient for photoluminescence readout of assays that use phosphorescent reporters of the present disclosure. As such, the phosphorescent reporters of the present disclosure can find numerous applications in various diagnostic and analytical methods. Furthermore, the phosphorescent reporters of the present disclosure can be used in qualitative and quantitative manners.

In some embodiments, the phosphorescent reporters of the present disclosure may be utilized in assay settings, such as lateral flow. In some embodiments, the phosphorescent reporters of the present disclosure may be bound to surfaces in flow-through assays. In some embodiments, the phosphorescent reporters of the present disclosure may be utilized in diagnostic immunoassays, assays for detecting nucleic acids, proteins, whole viruses, bacteria or small molecules. In some embodiments, the phosphorescent reporters of the present disclosure can serve as labels in assays used for diagnosing disease, monitoring levels of biologically or clinically relevant molecules, detecting narcotic substances, detecting pathogens in water, food, or other samples, in vivo imaging, flow cytometry applications, monitoring levels of chemicals in the environment, and additional applications. In some embodiments, phosphorescent reporters of the present disclosure could be utilized in devices designed to detect biomarkers for monitoring health or diagnosing disease at the point-of-care. In some embodiments, devices designed to readout luminescence for lateral flow, flow through, flotation, and other formats can incorporate the phosphorescent reporters of the present disclosure as labels.

In some embodiments, the phosphorescent reporters of the present disclosure can be used to improve point-of-care diagnostics. Point-of-care diagnostics have the potential to improve the quality of healthcare by providing simple, low-cost systems for the detection of infectious pathogens and biomarkers of disease. Numerous point-of-care diagnostic platforms have been developed that incorporate fluorescent labels as the readout signal. However, the organic dyes used in these labels are prone to photobleaching, and fluorescence imaging requires a complex optical system with expensive excitation and emission filters due to the short lifetime of the excited state.

In some embodiments, the phosphorescent reporters of the present disclosure are used in lateral flow devices. In some embodiments, the phosphorescent reporter of the present disclosure are contacted with an analyte, and flow through a membrane to a test line where antibodies or other recognition elements immobilized on the membrane bind to the analyte. Luminescence is measured by imaging with a camera or by taking quantitative measurements with a luminometer or other light detection device. The intensity of the light from the phosphorescent reporters is used in the diagnostic analysis.

In some embodiments, the phosphorescent reporters of the present disclosure are used as components of settling, magnetic relocation, or flotation devices. For instance, in some embodiments, phosphorescent reporters of the present disclosure are immobilized on a flotation object like a micro-bubble or thin polymer sheet to form an immunosandwich with the analyte and biofunctionalized phosphors. Buoyant forces can then relocate the flotation module with the attached phosphors to the top of the solution where luminescence is measured or imaged. A dye may be used to reduce the background signal from phosphors in solution not attached to the flotation object.

In some embodiments, the phosphorescent reporters of the present disclosure are used as components of flow through devices. For instance, in some embodiments, antibodies or biorecognition elements are immobilized on a membrane. A sample containing a phosphorescent reporter (e.g., biofunctionalized phosphors) in contact with an analyte are then applied to the top of the membrane. Immunosandwiches then form between biorecognition elements on the membrane, the analyte, and the phosphorescent reporters. Unbound phosphorescent reporters pass through the membrane. Luminescence from the membrane is then imaged or measured.

In some embodiments, the phosphorescent reporters of the present disclosure may be used in surface binding. For instance, in some embodiments, antibodies or other molecular recognition elements are immobilized on a surface. A sample containing phosphorescent reporters that are in contact with an analyte is then applied to the surface. Immunosandwiches form between biorecognition elements on the surface, the analyte, and phosphorescent reporters. Unbound phosphors are removed, optionally by flow force stringency. Luminescence from the surface is then imaged or measured.

In some embodiments, the phosphorescent reporters of the present invention may be excited or stimulated to produce luminescence by means other than with light. In some embodiments, the phosphorescent reporters may be stimulated by the application of heat, current, or electric fields. These excitation methods allow more flexibility in assay format design, and can potentially lead to enhanced sensitivity.

REFERENCES

[1] Bauer, C. Bieniarz, and A. L. Hartman, "Nanoparticle Conjugates," US 2009/0181398 A1 2009.
[2] Benjamin R. Irvin, "Calibration System for use with Lateral Flow Assay Test Strips," U.S. Pat. No. 8,101,415 B2 2012.
[3] H. Boehringer, G. Rowley, and A. Pronovost, "Quantitative Lateral Flow Assays and Devices," U.S. Pat. No. 6,924,153 B12005.
[4] D. V. Borich, S. Savoy, M. McAleer, A. Milder, and D. Mitchell, "Universal Optical Imaging and Processing System," U.S. Pat. No. 7,803,322 B2 2010.
[5] E. P. Diamandis, "Europium and Terbium Chelators for the Time-Resolved Fluorometric Assays," U.S. Pat. No. 5,854,008 1998.
[6] Y. Dong, N. Wang, S. Cheng, and Y. Li, "Aluminate-Based Blue Phosphors," U.S. Pat. No. 7,390,437 B2 2008.
[7] P. Gibbs, "Point-of-Care Immunoassay for Quantitative Small Analyte Detection," US 2013/0102003 A1 2013.
[8] Y. Hirata, T. Sakaguchi, and N. Takeuchi, "Phosphorescent Phosphor and Method of Manufacturing Thereof," U.S. Pat. No. 7,427,365 B2 2008.
[9] W. Hoheisel, C. Petry, M. Haase, K. Riwotzki, and K. Bohmann, "Doped Nanoparticles as Biolabels," US2004/0014060 A12004.
[10] I. Hurley, "Time-Resolved Fluorometer," U.S. Pat. No. 5,061,076 1991.
[11] H. Lee and M. A. Dineva, "Dipstick Assay," U.S. Pat. No. 7,713,746 B2 2010.
[12] S. Lipp, "Method of Improving Moisture Resistance for Inorganic Materials that are Sensitive to Moisture," U.S. Pat. No. 6,242,043 B1 2001.
[13] M. Maurer, N. Raetzo, and R. Fischer, "Inorganic Phosphor, Obtainable by Wet Milling," US 2011/0038947 A1 2011.
[14] A. Ozcan, H. Zhu, and S. Mavandadi, "Compact Wide-Field Fluorescent Imaging on a Mobile Device," US 2012/0157160 A1 2012.
[15] A. Ozcan, O. Mudanyali, S. Dimitrov, U. Sikora, S. Padmanabhan, and I. Navrus, "Portable Rapid Diagnostic Test Reader," US 2013/0203043 A1 2013.
[16] R. J. Pet, M. M. C. I. van den Nieuwenhof, and J. P. H. M. Duisters, "Method of Preparing a Luminescent Eu2+ Activated Strontium Aluminate," U.S. Pat. No. 4,795,588 1989.
[17] J. Robert W. Hyland, J. P. Quintenz, B. T. Dunville, and G. Subrahmanyam, "Photoluminescent Alkaline Earth Aluminate and Method for Making the Same," U.S. Pat. No. 6,969,475 B2 2005.
[18] A. Sanjurjo, K.-H. Lau, D. Lowe, A. Canizales, J. Naixiong, V. Wong, L. Jiang, L. V. Schneider, N. Mufti, R. T. Rewick, M. Johansson, and K. Kardos, "Production of Substantially Monodisperse Phosphor Particles," U.S. Pat. No. 6,039,894 2000.
[19] D. Scherman, M. Bessodes, C. Chaneac, D. L. Gourier, J.-P. Jolivet, Q. L. M. De Chermont, S. Maitrejean, and F. S. Pelle, "Persistent Luminescence Nanoparticles used in the form of a Diagnosis Agent for in vivo Optical Imaging," U.S. Pat. No. 8,709,383 B2 2014.
[20] X. Song, "Membrane-Based Lateral Flow Assay Devices that Utilize Phosphorescent Detection," U.S. Pat. No. 8,557,604 B2 2013.
[21] W. Stober, "Method of Producing Monodisperse Silica Spheres Having a Dispersed Radioactive Tracer," U.S. Pat. No. 3,634,558 1972.
[22] M. Sun, "Lateral Flow Test Device," U.S. Pat. No. 6,372,516 B1 2002.
[23] H. J. Tanke, J. C. Slats, and J. S. Ploem, "Inorganic Phosphor Labelled Macromolecules; a process for their preparation and their use for immunological or immunocytochemical assays," U.S. Pat. No. 5,043,265 1991.
[24] U. Wiesner, H. Ow, D. R. Larson, and W. W. Webb, "Fluorescent Silica-Based Nanoparticles," U.S. Pat. No. 8,298,677 B2 2012.
[25] C.-Y. Yang, "Light Source Device for Time-Delayed Detection of Fluorescence, and Image Pick-up System and Method," US 2013/0087719 A1 2013.
[26] K. Yang, X. Song, K. P. McGrath, R. Boga, S. R. Feaster, and D. Cohen, "Flow-Through Assay Devices," US 2004/0106190 A1 2004.
[27] D. A. Zarling, M. J. Rossi, N. A. Peppers, J. Kane, G. W. Faris, M. J. Dyer, S. Y. Ng, and L. V Schneider, "Up-Converting Reporters for Biological and Other Assays Using Laser Excitation Techniques," U.S. Pat. No. 5,674,698 1997.
[28] A. J. Dekker, "Luminescence," in *Solid State Physics*, London: Macmillan & Co Ltd, 1962, pp. 398-417.
[29] J. Hampl, M. Hall, N. a Mufti, Y. M. Yao, D. B. MacQueen, W. H. Wright, and D. E. Cooper, "Upconverting phosphor reporters in immunochromatographic assays.," *Anal. Biochem.*, vol. 288, no. 2, pp. 176-87, January 2001.
[30] P. T. Ji, X. Y. Chen, and Y. Q. Wu, "Encapsulating MAl2O4: Eu2+, Dy3+ (M=Sr, Ca, Ba) phosphors with triethanolamine to enhance water resistance," *Appl. Surf Sci.*, vol. 258, no. 5, pp. 1888-1893, December 2011.

[31] E. Juntunen, T. Myyrylainen, T. Salminen, T. Soukka, and K. Pettersson, "Performance of fluorescent europium (III) nanoparticles and colloidal gold reporters in lateral flow bioaffinity assay.," *Anal. Biochem.*, vol. 428, no. 1, pp. 31-8, September 2012.

[32] P. Kingshott, H. Thissen, and H. J. Griesser, "Effects of cloud-point grafting, chain length, and density of PEG layers on competitive adsorption of ocular proteins.," *Biomaterials*, vol. 23, no. 9, pp. 2043-56, May 2002.

[33] C. F. Lane, "Sodium Cyanoborohydride—A Highly Selective Reducing Agent for Organic Functional Groups," *Synthesis (Stuttg).*, vol. 1975, no. 03, pp. 135-146, 1975.

[34] L. Lee, E. Nordman, M. Johnson, and M. Oldham, "A Low-Cost, High-Performance System for Fluorescence Lateral Flow Assays," *Biosensors*, vol. 3, no. 4, pp. 360-373, October 2013.

[35] X. Lü, "Silica encapsulation study on SrAl2O4:Eu2+, Dy3+ phosphors," *Mater. Chem. Phys.*, vol. 93, no. 2-3, pp. 526-530, October 2005.

[36] T. Maldiney, A. Lecointre, B. Viana, A. Bessière, M. Bessodes, D. Gourier, C. Richard, and D. Scherman, "Controlling electron trap depth to enhance optical properties of persistent luminescence nanoparticles for in vivo imaging.," *J. Am. Chem. Soc.*, vol. 133, no. 30, pp. 11810-5, August 2011.

[37] M. Malmsten, K. Emoto, and J. M. Van Alstine, "Effect of Chain Density on Inhibition of Protein Adsorption by Poly(ethylene glycol) Based Coatings," *J. Colloid Interface Sci.*, vol. 202, no. 2, pp. 507-517, June 1998.

[38] T. Matsuzawa, "A New Long Phosphorescent Phosphor with High Brightness, SrAl2O4:Eu2+,Dy3+," *J. Electrochem. Soc.*, vol. 143, no. 8, p. 2670, 1996.

[39] E. Mine, A. Yamada, Y. Kobayashi, M. Konno, and L. M. Liz-Marzán, "Direct coating of gold nanoparticles with silica by a seeded polymerization technique.," *J. Colloid Interface Sci.*, vol. 264, no. 2, pp. 385-90, August 2003.

[40] O. Mudanyali, S. Dimitrov, U. Sikora, S. Padmanabhan, I. Navruz, and A. Ozcan, "Integrated rapid-diagnostic-test reader platform on a cellphone.," *Lab Chip*, vol. 12, no. 15, pp. 2678-86, August 2012.

[41] S. Prabakar and R. a. Assink, "Hydrolysis and condensation kinetics of two component organically modified silica sols," *J. Non. Cryst. Solids*, vol. 211, no. 1-2, pp. 39-48, April 1997.

[42] S. Ramachandran, M. Singhal, K. McKenzie, J. Osborn, A. Arjyal, S. Dongol, S. Baker, B. Basnyat, J. Farrar, C. Dolecek, G. Domingo, P. Yager, and B. Lutz, "A Rapid, Multiplexed, High-Throughput Flow-Through Membrane Immunoassay: A Convenient Alternative to ELISA," *Diagnostics*, vol. 3, no. 2, pp. 244-260, April 2013.

[43] J. S. Reed, "Comminution," in *Introduction to the Principles of Ceramic Processing*, New York: John Wiley & Sons, 1988, pp. 255-272.

[44] Y. Ryu, Z. Jin, M. S. Kang, and H.-S. Kim, "Increase in the detection sensitivity of a lateral flow assay for a cardiac marker by oriented immobilization of antibody," *BioChip J.*, vol. 5, no. 3, pp. 193-198, September 2011.

[45] J. Sanchez and A. McCormick, "Kinetic and Thermodynamic Study of the Hydrolysis of Silicon Alkoxides in Acidic Alcohol Solutions," *J. Phys. Chem.*, vol. 96, no. 22, pp. 8973-8979, October 1992.

[46] X. Song, L. Huang, and B. Wu, "Bright and Monodispersed Phosphorescent Particles and their Applications for Biological Assays," *Anal. Chem.*, vol. 80, no. 14, pp. 5501-7, July 2008.

[47] R. Wong and H. Y. Tse, Eds., *Lateral Flow Immunoassay*. Totowa, N.J.: Humana Press, 2009.

[48] Z. Zhang, A. E. Berns, S. Willbold, and J. Buitenhuis, "Synthesis of poly(ethylene glycol) (PEG)-grafted colloidal silica particles with improved stability in aqueous solvents.," *J. Colloid Interface Sci.*, vol. 310, no. 2, pp. 446-55, June 2007.

[49] Y. Zhu, J. Zeng, W. Li, L. Xu, Q. Guan, and Y. Liu, "Encapsulation of strontium aluminate phosphors to enhance water resistance and luminescence," *Appl. Surf Sci.*, vol. 255, no. 17, pp. 7580-7585, June 2009.

[50] Y. Zhu, M. Zheng, J. Zeng, Y. Xiao, and Y. Liu, "Luminescence enhancing encapsulation for strontium aluminate phosphors with phosphate," *Mater. Chem. Phys.*, vol. 113, no. 2-3, pp. 721-726, February 2009.

What is claimed is:

1. A method for determining a presence or absence of an analyte in a sample comprising steps of:

providing a phosphorescent reporter, wherein the phosphorescent reporter comprises an inorganic phosphorescent particle core comprising strontium aluminate, a shell encapsulating the inorganic phosphorescent particle core, and at least one molecular recognition moiety disposed on the shell, wherein the at least one molecular recognition moiety specifically binds to the target analyte, and wherein the phosphorescent reporter particle has a diameter from 10 nm to 1000 nm;

contacting the phosphorescent reporter to the sample or a portion thereof;

after the contacting step, specifically detecting a luminescence signal of the phosphorescent reporter, wherein the phosphorescent reporter is bound to the target analyte via the at least one molecular recognition moiety if the target analyte is present in the sample; and determining the presence or absence of the analyte in the sample based on detecting an increase or a decrease in the luminescence signal of the phosphorescent reporter or no change in the luminescence signal of the phosphorescent reporter after the contacting step.

2. The method of claim 1, further comprising the step of pretreating the sample if the analyte is present in the sample.

3. The method of claim 2, wherein the step of pretreating the sample involves amplification of the analyte, wherein the analyte comprises a nucleic acid.

4. The method of claim 2, wherein the step of pretreating the sample involves partial purification of the analyte.

5. The method of claim 1, wherein the step of detecting the luminescence signal comprises application of electromagnetic radiation to the phosphorescent reporters.

6. A method for in vitro detecting a presence or absence of an analyte in a sample, comprising steps of:

providing a porous material loaded with a phosphorescent reporter, wherein the phosphorescent reporter comprises an inorganic phosphorescent particle core comprising strontium aluminate, a shell encapsulating the inorganic phosphorescent particle core, and at least one molecular recognition moiety disposed on the shell, wherein the at least one molecular recognition moiety specifically binds to the target analyte, and wherein the phosphorescent reporter particle has a diameter from 10 nm to 1000 nm;

forming a mixture by contacting the sample with the porous material loaded with the phosphorescent reporter;

flowing the mixture through a porous membrane, wherein the porous membrane comprise a molecular recognition moiety which can interact with the analyte; and detecting the analyte in the sample by detecting a luminescence signal of the phosphorescent reporter on the membrane, wherein the presence of the luminescence signal of the phosphorescent reporter at an area on the membrane indicates that the analyte is present in the sample.

* * * * *